(12) United States Patent
Zaher

(10) Patent No.: US 9,682,908 B2
(45) Date of Patent: *Jun. 20, 2017

(54) METHOD FOR PRODUCING BUTANOL USING EXTRACTIVE FERMENTATION

(71) Applicant: BUTAMAX ADVANCED BIOFUELS LLC, Wilmington, DE (US)

(72) Inventor: Joseph J Zaher, Newark, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/842,876

(22) Filed: Sep. 2, 2015

(65) Prior Publication Data

US 2016/0002132 A1   Jan. 7, 2016

Related U.S. Application Data

(63) Continuation of application No. 14/211,342, filed on Mar. 14, 2014, now Pat. No. 9,156,760.

(60) Provisional application No. 61/790,828, filed on Mar. 15, 2013.

(51) Int. Cl.
C07C 29/86 (2006.01)
C12P 7/16 (2006.01)

(52) U.S. Cl.
CPC ............... *C07C 29/86* (2013.01); *C12P 7/16* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 2,461,938 A | 2/1949 | Strohmaier et al. | |
| 4,399,000 A | 8/1983 | Tedder | |
| 4,865,973 A | 9/1989 | Kollerup et al. | |
| 4,909,939 A | 3/1990 | Rickelton et al. | |
| 5,625,109 A | 4/1997 | Gupta et al. | |
| 7,666,282 B2 | 2/2010 | Sylvester et al. | |
| 8,409,834 B2 | 4/2013 | Burlew et al. | |
| 8,426,173 B2 | 4/2013 | Bramucci et al. | |
| 8,426,174 B2 | 4/2013 | Bramucci et al. | |
| 8,460,439 B2 | 6/2013 | Parten | |
| 8,476,047 B2 | 7/2013 | Burlew et al. | |
| 8,557,540 B2 | 10/2013 | Burlew et al. | |
| 8,563,788 B2 | 10/2013 | Grady et al. | |
| 8,569,552 B2 | 10/2013 | Grady et al. | |
| 8,574,406 B2 | 11/2013 | Grady et al. | |
| 8,614,077 B2 | 12/2013 | Evanko et al. | |
| 8,617,861 B2 | 12/2013 | Grady et al. | |
| 8,628,643 B2 | 1/2014 | Grady et al. | |
| 8,697,404 B2 | 4/2014 | Anton et al. | |
| 8,759,044 B2 | 6/2014 | Dicosimo et al. | |
| 8,765,425 B2 | 7/2014 | Dicosimo et al. | |
| 8,828,695 B2 | 9/2014 | Grady et al. | |
| 9,156,760 B2 * | 10/2015 | Zaher ...................... C07C 29/86 |
| 2007/0092957 A1 | 4/2007 | Donaldson et al. | |
| 2007/0292927 A1 | 12/2007 | Donaldson et al. | |
| 2008/0182308 A1 | 7/2008 | Donaldson et al. | |
| 2008/0274526 A1 | 11/2008 | Bramucci et al. | |
| 2009/0305370 A1 | 12/2009 | Grady et al. | |
| 2010/0143995 A1 | 6/2010 | Erdner-Tindall et al. | |
| 2011/0097773 A1 | 4/2011 | Grady et al. | |
| 2011/0136193 A1 | 6/2011 | Grady et al. | |
| 2011/0162953 A1 | 7/2011 | Xu et al. | |
| 2011/0162954 A1 | 7/2011 | Xu et al. | |
| 2011/0294179 A1 | 12/2011 | Grady et al. | |
| 2011/0306801 A1 | 12/2011 | Schucker | |
| 2011/0312044 A1 | 12/2011 | Anton et al. | |
| 2011/0312053 A1 | 12/2011 | Burlew et al. | |
| 2011/0315541 A1 | 12/2011 | Xu | |
| 2012/0064590 A1 | 3/2012 | Evanko et al. | |
| 2012/0156738 A1 | 6/2012 | Anton et al. | |
| 2012/0208246 A1 | 8/2012 | Anton et al. | |
| 2012/0323047 A1 | 12/2012 | Dauner et al. | |
| 2013/0164795 A1 | 6/2013 | Lowe et al. | |
| 2013/0217060 A1 | 8/2013 | Bramucci et al. | |
| 2013/0224728 A1 | 8/2013 | Bramucci et al. | |
| 2013/0236935 A1 | 9/2013 | Burlew et al. | |
| 2013/0252297 A1 | 9/2013 | Parten | |
| 2013/0295661 A1 | 11/2013 | Roesch et al. | |
| 2013/0309738 A1 | 11/2013 | Barr et al. | |
| 2014/0018581 A1 | 1/2014 | Grady et al. | |
| 2014/0024064 A1 | 1/2014 | Burlew et al. | |
| 2014/0073021 A1 | 3/2014 | Bazzana et al. | |

(Continued)

OTHER PUBLICATIONS

Cheng et al., "Computer-aided biocompatible solvent design for an integrated extractive fermentation-separation process", Chemical Engineering Journal, vol. 162, 2010, pp. 809-820, XP027190238.
Job et al., "Selection of Organic Solvents for In Situ Extraction of Fermentation Products from Clostridium Thermohydrosulfuricum Cultures", Biotechnology Techniques, vol. 3, 1989, pp. 315-320, XP002726205.
Jurgens et al., "Butanol Production From Lignocellulosics", Biotechnology Letters, vol. 34, 2012, pp. 1415-1434, XP035089776.
Kim et al., "Extractive Recovery of Products from Fermentation Broths". Biotechnology and Bioprocess Engineering, vol. 4, 1999, pp. 1-11, XP002725590.
Kraemer et al., "Separation of Butanol from Acetone-butanol-ethanol Fermentation by a Hybrid Extraction-distillation Process", Computers and Chemical Engineering, vol. 35, 2011, pp. 949-963, XP028192868.

(Continued)

*Primary Examiner* — Brian J Davis

(57) ABSTRACT

Provided herein are methods for recovering butanol from a fermentation medium. The methods comprise providing a fermentation medium comprising butanol, water, and a recombinant microorganism comprising a butanol biosynthetic pathway, wherein the recombinant microorganism produces butanol; contacting the fermentation medium with a water immiscible organic extractant composition comprising a dry solvent to form a butanol-containing organic phase and an aqueous phase; and recovering the butanol from the butanol-containing organic phase.

18 Claims, 17 Drawing Sheets

(56) References Cited

U.S. PATENT DOCUMENTS

| | | |
|---|---|---|
| 2014/0073820 A1 | 3/2014 | Bazzana et al. |
| 2014/0080189 A1 | 3/2014 | Grady et al. |
| 2014/0093931 A1 | 4/2014 | Dauner et al. |
| 2014/0094630 A1 | 4/2014 | Anton et al. |
| 2014/0099688 A1 | 4/2014 | Grady et al. |
| 2014/0106419 A1 | 4/2014 | Bazzana et al. |
| 2014/0142352 A1 | 5/2014 | Dauner et al. |
| 2014/0162344 A1 | 6/2014 | Dicosimo et al. |
| 2014/0178529 A1 | 6/2014 | Anton et al. |
| 2014/0234929 A1 | 8/2014 | Barr et al. |
| 2014/0256020 A1 | 9/2014 | Dicosimo et al. |
| 2014/0273127 A1 | 9/2014 | Fuchs et al. |
| 2014/0273130 A1 | 9/2014 | Anthony et al. |
| 2014/0311889 A1 | 10/2014 | Zaher et al. |
| 2014/0363865 A1 | 12/2014 | Burlew et al. |
| 2015/0010984 A1 | 1/2015 | Bhalla et al. |

OTHER PUBLICATIONS

Shimizu et al., "A Solvent Screening Criterion for Multicomponent Extractive Fermentation", Chemical Engineering Science, vol. 42, 1987, pp. 499-504, XP002726206.

International Search Report and Written Opinion, mailed on Jul. 7, 2014, in International Patent Application No. PCT/US2014/029260.

Roffler et al., "In situ extractive fermentation of acetone and butanol," Biotechnol. Bioeng. 31:135-43 (1988).

Roffler et al., "In situ recovery of butanol during fermentation," Bioprocess Engineering 2:1-12 (1987).

Evans et al., "Enhancement of butanol formation by Clostridium acetobutylicum in the presence of decanol-oleyl alcohol mixed extractants," Appl. Environ. Microbiol. 54:1662-7 (1988).

Alcantara et al., "Trimerization of isobutene over Amberlyst-15 catalyst," Reactive Funct. Polymers 45:19-27 (2000).

Ludwig et al., "Olefin hydrogenation on Pd model supported catalysts: new mechanistic insights," J. Catalysis 284:148-56 (2011).

Atsumi et al., "Non-fermentative pathways for synthesis of branched-chain higher alcohols as biofuels," Nature 451 (3):86-90 (2008).

Markovic et al., "Extremely branched alkanes," J. Molecular Structure 629:303-6 (2003).

Kim et al., "Extractive Recovery of Products from Fermentation Broths," Biotechnol. Bioprocess Eng. 4:1-11 (1999).

Evans et al., "Response of Clostridium Acetobutylicum to the presence of mixed extractants," Appl. Biochem. Biotechnol. 175-92 (1988).

Groot et al., "Butanol recovery from fermentations by liquid-liquid extraction and membrane solvent extraction," Bioprocess Engineering 5:203-16 (1990).

Malinowski, "Two-phase partitioning bioreactors in fermentation technology," Biotechnology Advances 19:525-38 (2001).

Kollerup et al., "Screening and identification of extractive fermentation 1 solvents using a database," Canadian Journal of Chemical Engineering 63:919-27 (1985).

Kollerup et al., "Ethanol production by extractive fermentation-Solvent identification and prototype development," Canadian Journal of Chemical Engineering 64:598-606 (1986).

Bennis et al., "Surfface alteration of *Saccharomyces cerevisiae* induced by thymol and eugenol," Letters in Applied Microbiology 38:454-458 (2004).

Reregistration Eligibility Decision FACTS Thymol Pesticide Reregistration; U.S. Environmental Protection Agency; 1993; EPA-738-F-93-010; 1-4.

DeLiang et al., "Reactive Extraction of o-Aminophenol using trialkylphosphine oxide," Chinese J. Chem. Eng. 14 (1):46-50 (2006).

* cited by examiner

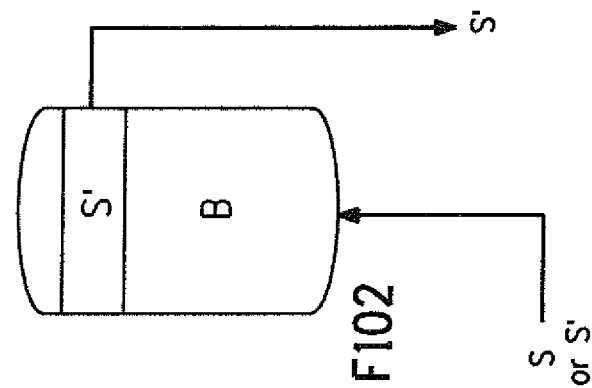
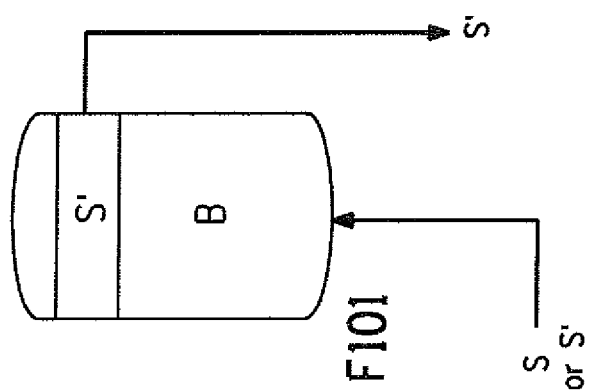
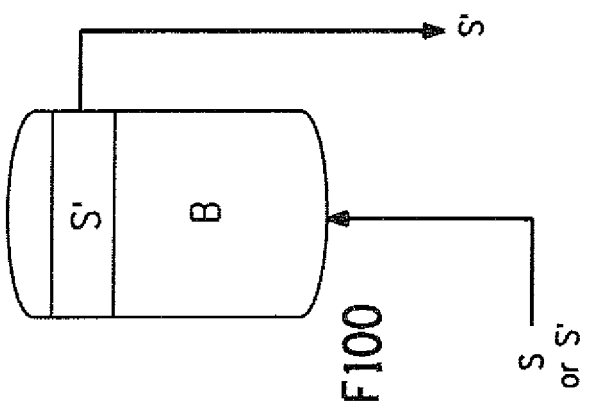
FIG. 7

METHOD FOR PRODUCING BUTANOL USING EXTRACTIVE FERMENTATION

CROSS-REFERENCE

This application is a continuation of and claims priority to U.S. patent application Ser. No. 14/211,342, filed on Mar. 14, 2014, which is related to and claims priority to U.S. Provisional Patent Application No. 61/790,828, filed on Mar. 15, 2013. Each application is hereby incorporated by reference in its entirety. Additionally, this application incorporates by reference in their entireties U.S. Provisional Patent Application No. 61/788,213, filed on 15 Mar. 2013, entitled Method for Production of Butanol Using Extractive Fermentation, and U.S. Provisional Patent Application Nos. 61/790,401, filed on 15 Mar. 2013, entitled Method for Production of Butanol Using Extractive Fermentation.

FIELD OF THE INVENTION

The invention relates to the field of industrial microbiology and the fermentative production of butanol and isomers thereof. More specifically, the invention relates to a method for producing butanol through microbial fermentation, in which the butanol product is removed by extraction into a water-immiscible extractant composition which comprises a dry solvent.

BACKGROUND

Butanol is an important industrial chemical, useful as a fuel additive, as a feedstock chemical in the plastics industry, and as a food grade extractant in the food and flavor industry. Each year 10 to 12 billion pounds of butanol are produced by petrochemical means and the need for this commodity chemical will likely increase in the future.

Several chemical synthetic methods are known; however, these methods of producing butanol use starting materials derived from petrochemicals and are generally expensive and are not environmentally friendly. Several methods of producing butanol by fermentation are also known, for example the ABE process which is the fermentive process producing a mixture of acetone, 1-butanol, and ethanol. Acetone-butanol-ethanol (ABE) fermentation by Clostridium acetobutylicum is one of the oldest known industrial fermentations; as are also the pathways and genes responsible for the production of these solvents. Production of 1-butanol by the ABE process is limited by the toxic effect of the 1-butanol on Clostridium acetobutylicum. In situ extractive fermentation methods using specific extractants which are nontoxic to the bacterium have been reported to enhance the production of 1-butanol by fermentation using Clostridium acetobutylicum (see, for example, Roffler et al., Biotechnol. Bioeng. 31:135-143, 1998; Roffler et al., Bioprocess Engineering 2:1-12, 1987; and Evans et al., Appl. Environ. Microbiol. 54:1662-1667, 1988).

In contrast to the native Clostridium acetobutylicum described above, recombinant microbial production hosts expressing 1-butanol, 2-butanol, and isobutanol biosynthetic pathways have also been described. These recombinant hosts have the potential of producing butanol in higher yields compared to the ABE process because they do not produce byproducts such as acetone and ethanol. With these recombinant hosts, the biological production of butanol appears to be limited by the butanol toxicity thresholds of the host microorganism used in the fermentation. U.S. Patent Publication No. 20090305370 discloses a method of making butanol from at least on fermentable carbon source that overcomes the issues of toxicity resulting in an increase in the effective titer, the effective rate, and the effective yield of butanol production by fermentation utilizing a recombinant microbial host wherein the butanol is extracted into specific organic extractants during fermentation.

Improved methods for producing and recovering butanol from a fermentation medium are continually sought. Lower cost processes and improvements to process operability are also desired. Identification of improved extractants for use with fermentation media, such as extractants exhibiting higher partition coefficients, lower viscosity, lower density, commercially useful boiling points, and sufficient microbial biocompatibility, is a continual need. Additionally, extractants that are selective for butanol over water provide certain advantages. By way of an example, an extractant that is selective for butanol over water can reduce the energy needs for a butanol fermentation process. The reduction in total energy needed to strip the butanol from the extractant can be due to the reduction in water associated with the extractant, as the energy required to strip butanol from the extractant is directly related to the amount of water present in the extractant.

The present invention satisfies the need to provide methods for recovering butanol from a fermentation medium by contacting the fermentation medium with an organic extractant composition comprising a dry solvent, wherein the dry solvent selectively extracts butanol from the fermentation medium.

BRIEF SUMMARY OF THE INVENTION

Provided herein are methods for recovering butanol from a fermentation medium. The methods comprise (a) providing a fermentation medium comprising butanol, water, and a recombinant microorganism comprising a butanol biosynthetic pathway, wherein the recombinant microorganism produces butanol; (b) contacting the fermentation medium with a water immiscible organic extractant composition comprising a dry solvent to form a butanol-containing organic phase and an aqueous phase; and (c) recovering the butanol from the butanol-containing organic phase.

In certain embodiments, the dry solvent is a saturated hydrocarbon. The saturated hydrocarbon can, for example, be a $C_7$ to $C_{22}$ alkane or a mixture thereof. The $C_7$ to $C_{22}$ alkane can be a branched $C_7$ to $C_{22}$ alkane. In some embodiments the alkane comprises up to a $C_{25}$ alkane. In further embodiments, the hydrocarbon is unsaturated or an aromatic hydrocarbon. The hydrocarbon can, for example, be a derivative of isobutanol. The derivative of isobutanol can, for example, be triisobutylene, diisobutylene, tetraisobutylene, isooctane, isohexadecane, 3,4,5,6,6-pentamethyl-2-heptanol, or isododecane.

In some embodiments, the organic extractant composition further comprises a second solvent. The second solvent can be, for example, a $C_4$ to $C_{22}$ fatty alcohol, a $C_4$ to $C_{28}$ fatty acid, an ester of a $C_4$ to $C_{28}$ fatty acid, a $C_4$ to $C_{22}$ fatty aldehyde, a $C_7$ to $C_{22}$ ether, amides, phosphate esters, ureas, phenols (phenolics), phosphinates, carbamates, phosphoramide, or mixtures thereof. The second solvent can be, for example, oleyl alcohol, phenyl alcohol, cetyl alcohol, lauryl alcohol, myristyl alcohol, stearyl alcohol, oleic acid, lauric acid, myristic acid, stearic acid, octanoic acid, decanoic acid, undecanoic acid, methyl myristate, methyl oleate, 1-nonanol, 1-decanol, 2-undecanol, 1-nonanal, 1-undecanol, undecanal, isododecanol, lauric aldehyde, 2-methylundecanal, oleamide, linoleamide, palmitamide, stearylamide, 2-ethyl- 1-hexanol, 2-hexyl-1-decanol, 2-octyl-1-dodecanol, or mixtures thereof. In embodiments, one or more of the solvents include one or more of phosphorous, nitrogen, sulfur, or oxygen. For example, at least one of the solvents is selected because it is polar or exhibits hydrogen bonding. The second solvent can increase the butanol partition coefficient of the organic extractant composition.

In some embodiments, the contacting of the organic extractant composition with the fermentation medium occurs in the fermentor. In other embodiments, the contacting of the organic extractant composition with the fermentation medium occurs outside the fermentor. In some embodiments, the butanol is recovered after transferring a portion of the fermentation medium from the fermentor to a vessel, wherein the contacting of the organic extractant composition with the fermentation medium occurs in the vessel. In some embodiments, the butanol is isobutanol.

In some embodiments, the recovered butanol has an effective titer from about 20 g per liter to about 50 g per liter of the fermentation medium. In some embodiments, the recovered butanol has an effective titer from about 22 g per liter to about 80 g per liter. In some embodiments, the recovered butanol has an effective titer from about 25 g per liter to about 50 g per liter. In embodiments, the recovered butanol has an effective titer of at least 25 g, at least 30 g, at least 46 g, at least 50 g, at least 60 g, or at least 70 g per liter of the fermentation medium.

In some embodiments, the recovered butanol has an effective titer from about 20 g per liter to about 80 g per liter of the fermentation medium. In some embodiments, the recovered butanol has an effective titer from about 25 g per liter to about 50 g per liter. In some embodiments, the recovered butanol has an effective titer from about 30 g per liter to about 80 g per liter. In embodiments, the recovered butanol has an effective titer of at least 25 g, at least 30 g, at least 35 g, at least 37 g, at least 40 g, or at least 45 g per liter of the fermentation medium.

Also provided are compositions comprising butanol in a water immiscible organic extractant compositions, wherein the organic extractant composition comprises a solvent, wherein the solvent is a dry solvent.

In certain embodiments, the dry solvent is a saturated hydrocarbon. The saturated hydrocarbon can, for example, be a $C_7$ to $C_{22}$ alkane or a mixture thereof. The $C_7$ to $C_{22}$ alkane can be a branched $C_7$ to $C_{22}$ alkane. The hydrocarbon can, for example, be a derivative of isobutanol. The derivative of isobutanol can, for example, be triisobutylene, diisobutylene, tetraisobutylene, isooctane, isohexadecane, 3,4,5,6,6-pentamethyl-2-heptanol, or isododecane.

In some embodiments, the organic extractant composition further comprises a second solvent. The second solvent can be, for example, a $C_4$ to $C_{22}$ fatty alcohol, a $C_4$ to $C_{28}$ fatty acid, an ester of a $C_4$ to $C_{28}$ fatty acid, a $C_4$ to $C_{22}$ fatty aldehyde, a $C_7$ to $C_{22}$ ether, or mixtures thereof. The second solvent can be, for example, oleyl alcohol, phenyl alcohol, cetyl alcohol, lauryl alcohol, myristyl alcohol, stearyl alcohol, oleic acid, lauric acid, myristic acid, stearic acid, octanoic acid, decanoic acid, undecanoic acid, methyl myristate, methyl oleate, 1-nonanol, 1-decanol, 2-undecanol, 1-nonanal, undecanol, undecanal, isododecanol, lauric aldehyde, 2-methylundecanal, oleamide, linoleamide, palmitamide, stearylamide, 2-ethyl-1-hexanol, 2-hexyl-1-decanol, 2-octyl-1-dodecanol, or mixtures thereof. Additional examples include, phosphine oxides, tetraalkyureas, alkylphenol, parabens, salicylates, and so forth. The second solvent can increase the butanol partition coefficient of the organic extractant composition.

In some embodiments, the butanol is isobutanol.

In some embodiments, a method of extracting alcohol from an aqueous solution comprises (A) selecting which solvents to be included in a solvent mixture by identifying a first solvent and a second solvent based on the first and second solvents' respective properties, wherein the first and second solvents have a similar chemical structure; (B) setting a limit for a ratio of the first and second solvents to be included in the solvent mixture based on the solvent mixture's hydrophobicity, where the hydrophobicity of the solvent mixture is not indicated by a linear combination of the first solvent's hydrophobicity and the second solvents hydrophobicity; (C) determining a ratio of the first solvent to the second solvent to be included in the solvent mixture within the limit to balance the solvent mixture's overall properties so the solvent mixture exhibits at least one synergistic property that is not indicated by a linear combination of the first and second solvents, respective, properties that correspond to the at least one synergistic property; and (D) contacting an aqueous solution including the alcohol with the solvent mixture to extract the alcohol. In examples, the hydrophobicity of the first solvent is the base ten log of the ratio of an amount first solvent in an organic phase divided by an amount of the first solvent in aqueous phase for a tertiary mixture of the first solvent and water in the presence of octanol; wherein the hydrophobicity of the second solvent is the base ten log of the ratio of an amount second solvent in an organic phase divided by an amount of the second solvent in aqueous phase for a tertiary mixture of the second solvent and water in the presence of octanol; and wherein the hydrophobicity of the solvent mixture is the base ten log of the ratio of an amount of solvent mixture in an organic phase divided by an amount of the solvent mixture in aqueous phase for a mixture of the solvent mixture and water in the presence of octanol. In additional examples, hydrophobicity comprises an indicator of biocompatibility. In further embodiments, the method includes interating steps A, B, and C for each solvent to be included in the solvent mixture to account for the solvent mixture's cumulative properties based on the first solvent's properties, the second solvent's properties, and the each solvent that is additionally included in the solvent mixture. In an example, the at least one synergistic property comprises hydrophobicity. In additional examples, hydrophobicity is expressed as log P. In embodiments, the at least one synergistic property comprises the solvent mixture's ability to solubilize water. In some examples, the at least one synergistic property comprises a partition coefficient of the solvent mixture in a mix with butanol and water (Kd). In some embodiments, the at least one synergistic property comprises biocompatibility with a microorganism that produces the alcohol. Additionally, in an example, the microorganism comprises a genetically modified microorganism. In further embodiments, the genetically modified microorganism comprises a butanologen. In some embodiments, at least one of the first or second solvents is substantially biocompatible with the butanologen. Additionally, in some embodiments, the first solvent is comparatively more bio-incompatible with the butanologen than the second solvent and exhibits greater alcohol selectivity than the second solvent. In some embodiments, at least one synergistic property comprises a low affinity to extract a nutrient from the aqueous solution. In examples, the nutrient comprise a nutrient that supports alcohol fermentation by a microorganism. In further examples, the butanologen comprises a butanologen with a biosynthetic pathway engineered to yield butanol in high amount in comparison to the ABE process. In some embodiments, the aqueous solution comprises fermentation broth including a microorganism genetically modified to produce the alcohol. In examples, the alcohol comprises a fusel. In some examples, the first solvent comprises a derivative of isobutanol. Further, in examples, the derivative of isobutanol comprises at least one of triisobutylene, diisobutylene, tetraisobutylene, isooctane, isohexadecane, 3,4,5,6,6-pentamethyl-2-heptanol, or isododecane. In embodiments in accordance with this disclosure, the first solvent comprises at least one of a C4 to C22 fatty alcohol, a C4 to C28 fatty acid, an ester of a C4 to C28 fatty acid, a C4 to C22 fatty aldehyde, a C7 to C22 ether, amides, phosphate esters, ureas, phenols (phenolics), phosphinates, carbamates, phosphoramide, or mixtures thereof. The first solvent comprises at least one of oleyl alcohol, phenyl alcohol, cetyl alcohol, lauryl alcohol, myristyl alcohol, stearyl alcohol, oleic acid, lauric acid, myristic acid, stearic acid, octanoic acid, decanoic acid, undecanoic acid, methyl myristate, methyl oleate, 1-nonanol, 1-decanol, 2-undecanol, 1-nonanal, 1-undecanol, undecanal, isododecanol, lauric aldehyde, 2-methylundecanal, oleamide, linoleamide, palmitamide, stearylamide, 2-ethyl-1-hexanol, 2-hexyl-1-decanol, 2-octyl-1-dodecanol, or mixtures thereof in embodiments of the present disclosure.

In some embodiments, a method of extracting alcohol from an aqueous solution comprises combining at least two solvents to form a solvent mixture that exhibits a synergistic alcohol extraction property that is not indicated by a linear combination of properties, where respective ones of the properties correspond to the at least two solvents, the at least two solvents being selected by identifying the at least two solvents based on the respective ones of the properties that correspond to the at least two solvents, wherein two of the at least two solvents have corresponding chemical structures; setting a limit for a ratio of the at least two solvents relative to each solvent in the solvent mixture based on each solvent's hydrophobicity, where the solvent mixture's hydrophobicity is not indicated by a linear combination of the hydrophobicities for each of the solvent included in the solvent mixture; and mixing the at least two solvents in a ratio within the limit to balance the solvent mixture's overall properties so the solvent mixture exhibits the synergistic alcohol extraction property. In embodiments, the method further comprises contacting an aqueous solution that includes the alcohol with the solvent mixture to extract the alcohol. In examples, the synergistic alcohol extraction property comprises the solvent mixture's ability to solubilize water. In additional examples, hydrophobicity comprises a partition coefficient of at least one solvent included in the at least two solvents or the solvent mixture in a mix with octanol, and water (log P). In further examples, the synergistic alcohol extraction property comprises a partition coefficient of the solvent mixture in a mix with butanol, and water (Kd). In an example, at least one solvent in the solvent mixture comprises a dry solvent that exhibits good biocompatibility with a microorganism capable of producing the alcohol and at least one solvent in the solvent mixture comprises a solvent that exhibits high affinity to the alcohol. In additional examples, the alcohol comprises a fusel. In examples, the fusel comprises butanol. Further examples include where the butanol comprises isobutanol. In embodiments, the aqueous solution comprises a broth that includes an isobutanolgen that is genetically modified to yield more isobutanol in comparison to the ABE process. In some embodiments, the synergistic alcohol extraction property comprises a poor extraction efficiency to a nutrient consumed by a microorganism to produce the alcohol. Further examples exist where hydrophobicity comprises an indicator of biocompatibility. In embodiments, the limit is approximate a log P of six (6). In some examples, the limit corresponds to a concentration of solvent mixture in the aqueous solution that is insufficient to appreciably impact integrity of a microorganism's cell membrane.

In some embodiments, a method of drying an extractant comprises contacting, with a first solvent, a fermentation broth that includes a recombinant microorganism comprising a butanol biosynthetic pathway and butanol produced via that butanol biosynthetic pathway to extract at least a portion of the butanol into the first solvent; and contacting the first solvent that includes at least a portion of the butanol and at least some water from the fermentation broth with a second solvent to extract the water from the first solvent into the second solvent to dry the first solvent including the butanol. In methods in accordance with these embodiments contacting the first and second solvents is performed out of the fermentation broth's presence. In further examples, the first solvent comprises a solvent mixture that is prepared by: combining at least two solvents to form the solvent mixture that exhibits a synergistic alcohol extraction property that is not indicated by a linear combination of properties, where respective ones of the properties correspond to the at least two solvents, the at least two solvents being selected by: identifying the at least two solvents based on the respective ones of the properties that correspond to the at least two solvents, wherein two of the at least two solvents have corresponding chemical structures; setting a limit for a ratio of the at least two solvents relative to each solvent in the solvent mixture based on each solvent's hydrophobicity, where the solvent mixture's hydrophobicity is not indicated by a linear combination of the hydrophobicities for each of the solvent included in the solvent mixture; and mixing the at least two solvents in a ratio within the limit to balance the solvent mixture's overall properties so the solvent mixture exhibits the synergistic alcohol extraction property. In some examples, the synergistic alcohol extraction property comprises the solvent mixture's ability to reject water. In some embodiments, hydrophobicity comprises a partition coefficient of at least one solvent included in the at least two solvents or the solvent mixture in a mix with octanol, and water (log P). Additionally, examples exist where the synergistic alcohol extraction property comprises a partition coefficient of the solvent mixture in a mix with butanol, and water (Kd). Further in an example, at least one solvent in the solvent mixture comprises a dry solvent that exhibits good biocompatibility with a microorganism capable of producing the alcohol and at least one solvent in the solvent mixture comprises a solvent that exhibits high affinity to the alcohol. In further embodiments, the alcohol comprises a fusel. Moreover, in some examples, the fusel comprises butanol. In further examples, the butanol comprises isobutanol. In some examples, the synergistic alcohol extraction property comprises a poor extraction efficiency to a nutrient consumed by a microorganism to produce the alcohol. In additional embodiments, hydrophobicity comprises an indicator of biocompatibility. In some embodiments in accordance with this disclosure, the limit is approximately log P of six (6). The method can also include where the limit corresponds to a concentration of solvent mixture in the aqueous solution that is insufficient to appreciably impact integrity of a microorganism's cell membrane. In examples, the second solvent comprises glycerol. Additionally, in examples contacting the first and second solvents is performed as a countercurrent extraction that is performed after the first solvent is contacted with the fermentation broth. In embodiments in accordance with the present disclosure the first solvent comprises a dry solvent.

BRIEF DESCRIPTION OF THE DRAWINGS/FIGURES

FIG. 1 schematically illustrates one embodiment of the methods of the invention, in which the first water immiscible extractant and the optional second water immiscible extractant are combined in a vessel prior to contacting the fermentation medium with the extractant in a fermentation vessel.

FIG. 2 schematically illustrates one embodiment of the methods of the invention, in which the first water immiscible extractant and the optional second water immiscible extractant are added separately to a fermentation vessel in which the fermentation medium is contacted with the extractant.

FIG. 3 schematically illustrates one embodiment of the methods of the invention, in which the first water immiscible extractant and the optional second water immiscible extractant are added separately to different fermentation vessels for contacting of the fermentation medium with the extractant.

FIG. 4 schematically illustrates one embodiment of the methods of the invention, in which extraction of the product occurs downstream of the fermentor and the first water immiscible extractant and the optional second water immiscible extractant are combined in a vessel prior to contacting the fermentation medium with the extractant in a different vessel.

FIG. 5 schematically illustrates one embodiment of the methods of the invention, in which extraction of the product occurs downstream of the fermentor and the first water immiscible extractant and the optional second water immiscible extractant are added separately to a vessel in which the fermentation medium is contacted with the extractant.

FIG. 6 schematically illustrates one embodiment of the methods of the invention, in which extraction of the product occurs downstream of the fermentor and the first water immiscible extractant and the optional second water immiscible extractant are added separately to different vessels for contacting of the fermentation medium with the extractant.

FIG. 7 schematically illustrates one embodiment of the methods of the invention, in which extraction of the product occurs in at least on-batch fermentor via co-current flow of a water-immiscible extractant comprising a first solvent and an optional second solvent at or near the bottom of a fermentation mash to fill the fermentor with extractant which flows out of the fermentor at a point at or near the top of the fermentor.

Figure 11A:
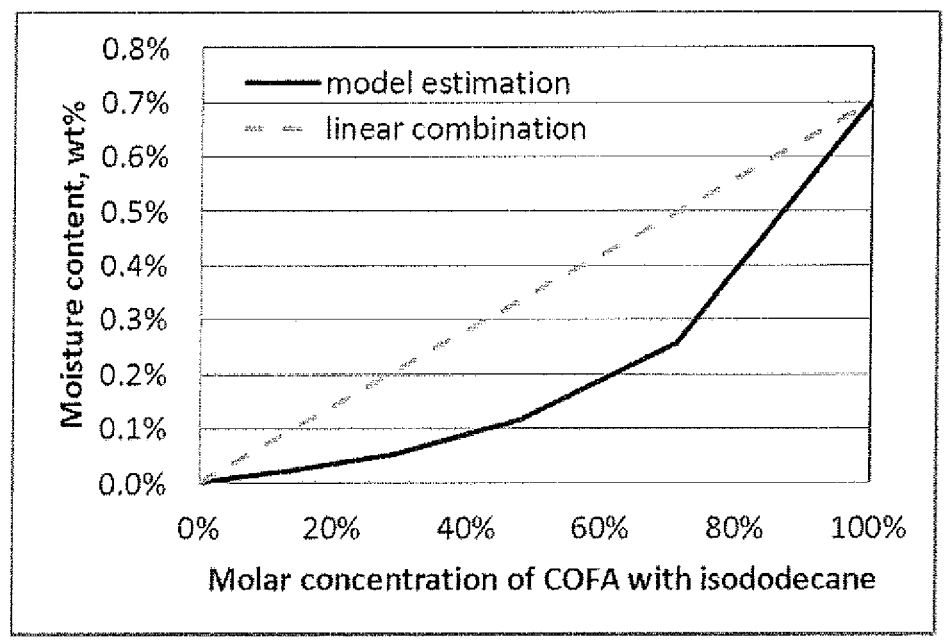
FIG. 11A is a graphical illustration of model estimations for COFA and isododecane in comparison to a linear combination model of COFA and isododecane.
Figure 11B:
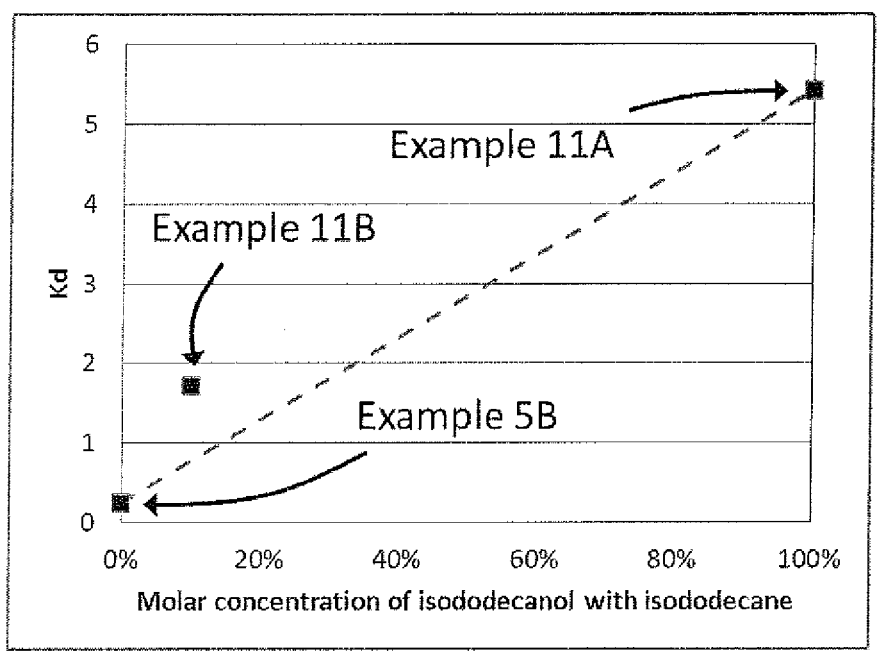

FIG. 11B graphically illustrates how various molar concentrations of isododecane/isododecanol impact Kd for the solvent mixture.

Figure 11C:
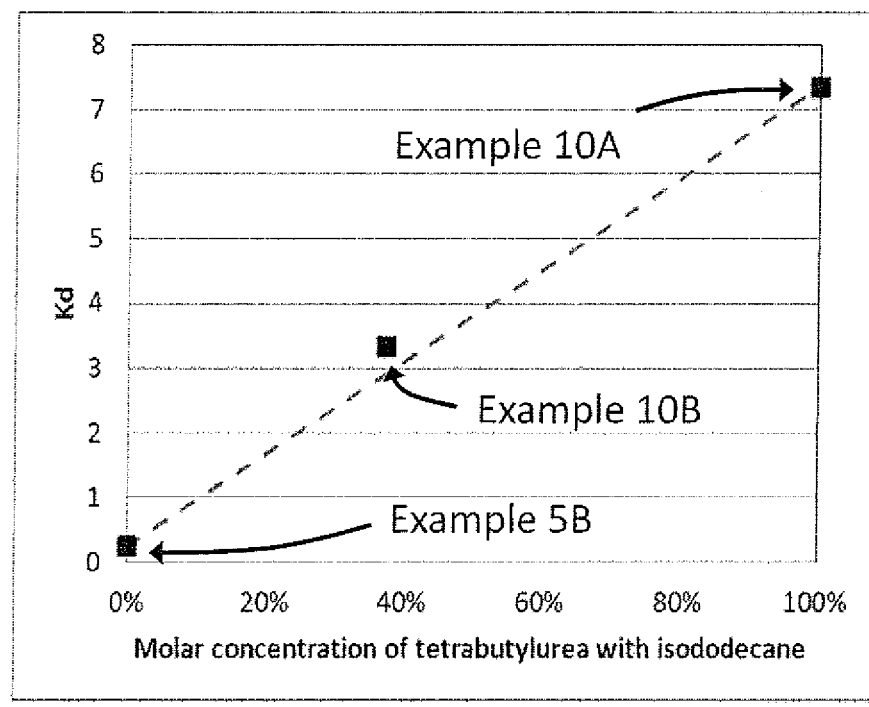

FIG. 11C graphically illustrates how various molar concentrations of tetrabutylurea with isododecane impact Kd for the solvent mixture.

Figure 12:
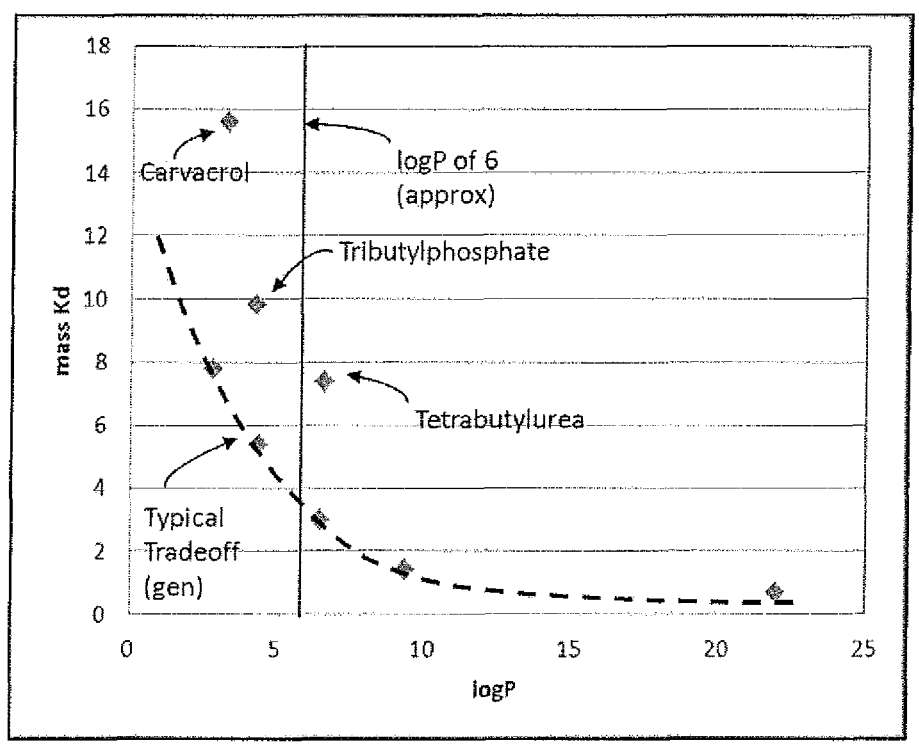

FIG. 12 is a graphical illustration of the Kd properties (partition coefficient for butanol) of several alkyphenol solvents relative to log P (hydrophobicity) for the solvents.

Figure 13:
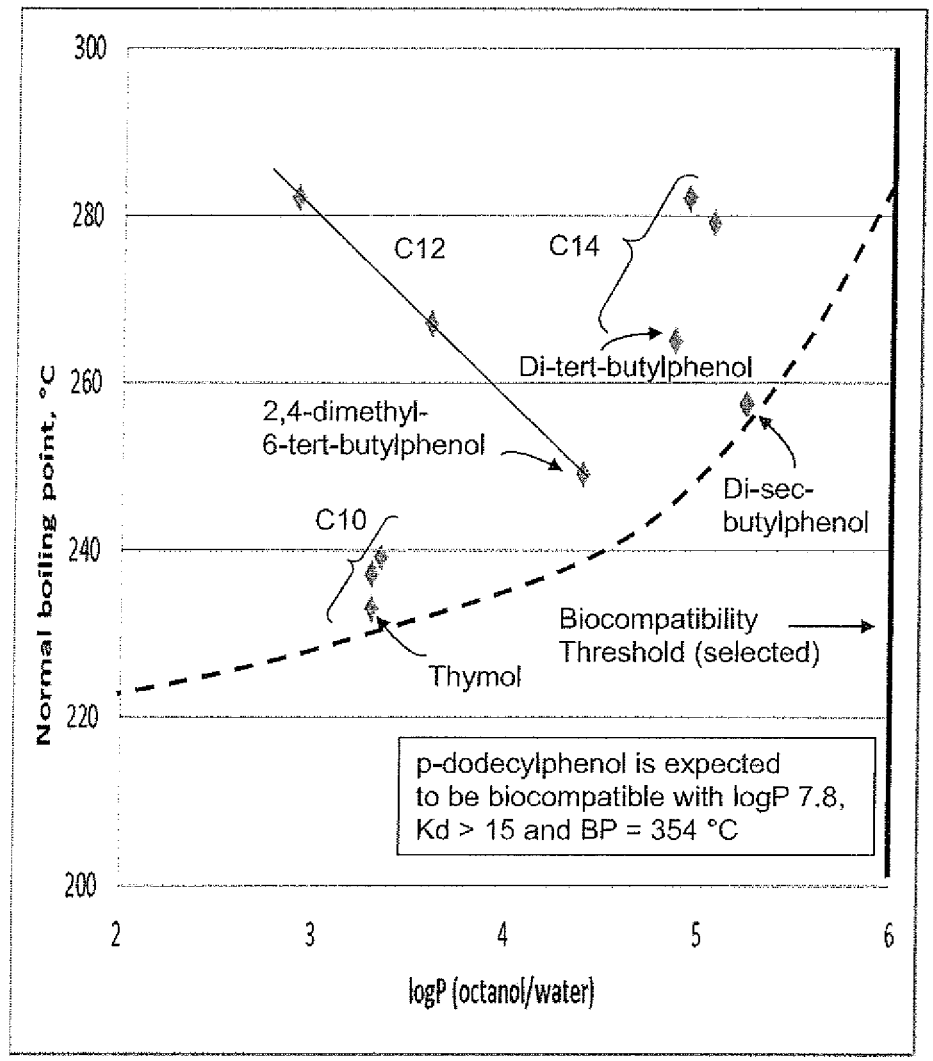

FIG. 13 is a graphical illustration of boiling points relative to log P (hydrophobicity) of several solvents including notations relating to the number of carbon atoms in the solvents.

Figure 14:
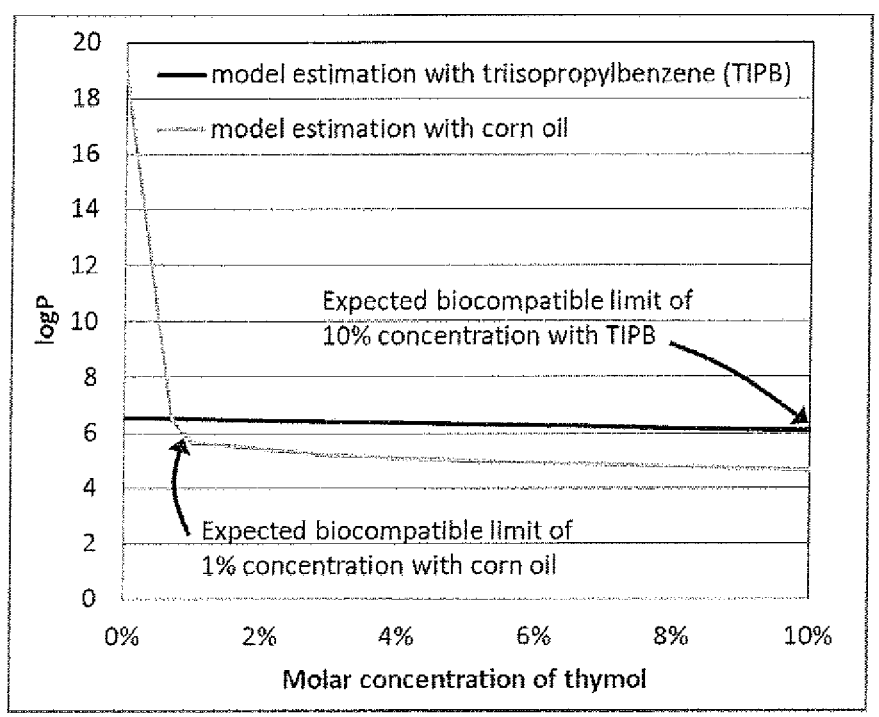

FIG. 14, is a graphical illustration of log P versus molar concentrations for solvent mixtures of corn oil and thymol and mixtures of triisopropylbenzene and thymol.

Figure 15:
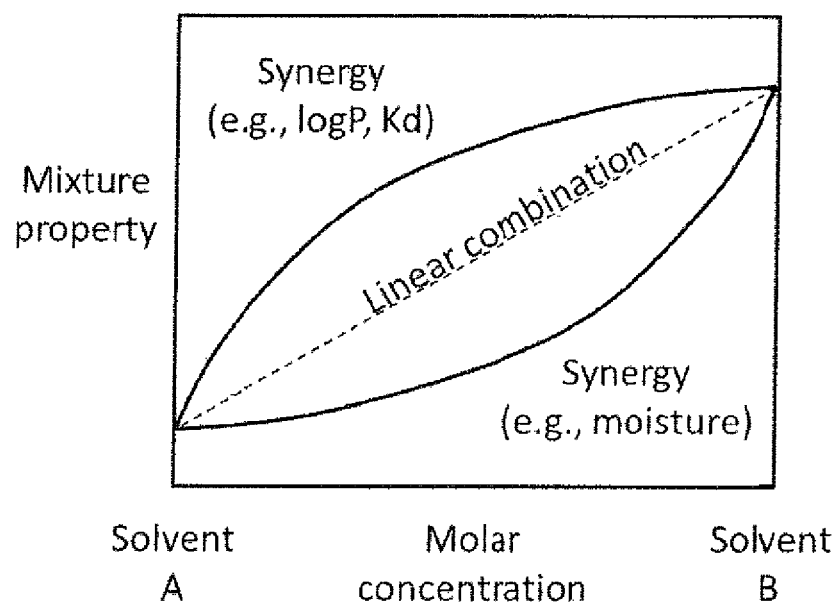

FIG. 15, is a graphical illustration of expected versus Potential Observed Properties.

DETAILED DESCRIPTION OF THE INVENTION

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference. Headings are implemented throughout this document to aid the reader's understanding of the disclosed subject matter. These headings are provided solely for the reader's convenience and should not be considered as limiting or dividing this disclosure into parts. And, the techniques, approaches, methodologies, systems and devices described in conjunction with one portion are generally applicable to other portions of this disclosure.

In order to further define this invention, the following terms, abbreviations and definitions are provided.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. §2111.03.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the claims as presented or as later amended and supplemented, or in the specification.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, or within 5% of the reported numerical value.

The term "butanol biosynthetic pathway" as used herein refers to the enzymatic pathway to produce 1-butanol, 2-butanol, or isobutanol.

The term "1-butanol biosynthetic pathway" refers to an enzymatic pathway to produce 1-butanol. A "1-butanol biosynthetic pathway" can refer to an enzyme pathway to produce 1-butanol from acetyl-coenzyme A (acetyl-CoA). For example, 1-butanol biosynthetic pathways are disclosed in U.S. Patent Application Publication No. 2008/0182308 and International Publication No. WO 2007/041269, which are herein incorporated by reference in their entireties.

The term "2-butanol biosynthetic pathway" refers to an enzymatic pathway to produce 2-butanol. A "2-butnaol biosynthetic pathway" can refer to an enzyme pathway to produce 2-butanol from pyruvate. For example, 2-butanol biosynthetic pathways are disclosed in U.S. Pat. No. 8,206,970, U.S. Patent Application Publication No. 2007/0292927, International Publication Nos. WO 2007/130518 and WO 2007/130521, which are herein incorporated by reference in their entireties.

The term "isobutanol biosynthetic pathway" refers to an enzymatic pathway to produce isobutanol. An "isobutanol biosynthetic pathway" can refer to an enzyme pathway to produce isobutanol from pyruvate. For example, isobutanol biosynthetic pathways are disclosed in U.S. Pat. No. 7,851,188, U.S. Application Publication No. 2007/0092957, and International Publication No. WO 2007/050671, which are herein incorporated by reference in their entireties. From time to time "isobutanol biosynthetic pathway" is used synonymously with "isobutanol production pathway."

The term "butanol" as used herein refers to the butanol isomers 1-butanol (1-BuOH), 2-butanol (2-BuOH), tert-butanol (t-BuOH), and/or isobutanol (iBuOH or i-BuOH, also known as 2-methyl-1-propanol), either individually or as mixtures thereof. From time to time, as used herein the terms "biobutanol" and "bio-produced butanol" may be used synonymously with "butanol."

Uses for butanol can include, but are not limited to, fuels (e.g., biofuels), a fuel additive, an alcohol used for the production of esters that can be used as diesel or biodiesel fuel, as a chemical in the plastics industry, an ingredient in formulated products such as cosmetics, and a chemical intermediate. Butanol may also be used as a solvent for paints, coatings, varnishes, resins, gums, dyes, fats, waxes, resins, shellac, rubbers, and alkaloids.

As used herein, the term "bio-produced" means that the molecule (e.g., butanol) is produced from a renewable source (e.g., the molecule can be produced during a fermentation process from a renewable feedstock). Thus, for example, bio-produced isobutanol can be isobutanol produced by a fermentation process from a renewable feedstock. Molecules produced from a renewable source can further be defined by the $^{14}C/^{12}C$ isotope ratio. A $^{14}C/^{12}C$ isotope ratio in range of from 1:0 to greater than 0:1 indicates a bio-produced molecule, whereas a ratio of 0:1 indicates that the molecule is fossil derived.

"Product alcohol" as used herein, refers to any alcohol that can be produced by a microorganism in a fermentation process that utilizes biomass as a source of fermentable carbon substrate. Product alcohols include, but are not limited to, $C_1$ to $C_8$ alkyl alcohols, and mixtures thereof. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, pentanol, and mixtures thereof. Likewise $C_2$ to $C_8$ alkyl alcohols include, but are not limited to, ethanol, propanol, butanol, and pentanol. "Alcohol" is also used herein with reference to a product alcohol.

A recombinant host cell comprising an "engineered alcohol production pathway" (such as an engineered butanol or isobutanol production pathway) refers to a host cell containing a modified pathway that produces alcohol in a manner different than that normally present in the host cell. Such differences include production of an alcohol not typically produced by the host cell, or increased or more efficient production.

The term "heterologous biosynthetic pathway" as used herein refers to an enzyme pathway to produce a product in which at least one of the enzymes is not endogenous to the host cell containing the biosynthetic pathway.

The term "extractant" as used herein refers to one or more organic solvents which can be used to extract a product alcohol. From time to time as used herein, the term "extractant" may be used synonymously with "solvent."

The term "dry solvent" as used herein refers to a solvent that selectively extracts the product alcohol (e.g., isobutanol) from an aqueous medium over water. By way of an example, a dry solvent can extract the product alcohol over water such that the equilibrium water content in the solvent is less than about 0.05%.

The term "effective isobutanol productivity" as used herein refers to the total amount in grams of isobutanol produced per gram of cells.

The term "effective titer" as used herein, refers to the total amount of a particular alcohol (e.g., butanol) produced by fermentation per liter of fermentation medium. The total amount of butanol includes: (i) the amount of butanol in the fermentation medium; (ii) the amount of butanol recovered from the organic extractant; and (iii) the amount of butanol recovered from the gas phase, if gas stripping is used.

The term "effective rate" as used herein, refers to the total amount of butanol produced by fermentation per liter of fermentation medium per hour of fermentation.

The term "effective yield" as used herein, refers to the amount of butanol produced per unit of fermentable carbon substrate consumed by the biocatalyst.

The term "separation" as used herein is synonymous with "recovery" and refers to removing a chemical compound from an initial mixture to obtain the compound in greater purity or at a higher concentration than the purity or concentration of the compound in the initial mixture.

The term "In Situ Product Removal" (ISPR) as used herein refers to the selective removal of a fermentation product from a biological process such as fermentation to control the product concentration as the product is produced.

The term "aqueous phase," as used herein, refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction, and the terms "solvent-poor phase" may be used synonymously with "aqueous phase" and "fermentation broth.".

The term "organic phase," as used herein, refers to the non-aqueous phase of a biphasic mixture obtained by contacting a fermentation broth with a water-immiscible organic extractant. From time to time, as used herein the terms "solvent-rich phase" may be used synonymously with "organic phase."

The term "aqueous phase titer" as used herein, refers to the concentration of product alcohol (e.g., butanol) in the fermentation broth.

The term "water-immiscible" as used herein refers to a chemical component such as an extractant or a solvent, which is incapable of mixing with an aqueous solution such as a fermentation broth, in such a manner as to form one liquid phase.

The term "moisture content" as used herein refers to the equilibrium saturation of water contained by the solvent, whether or not product alcohol, e.g., isobutanol is present. At times the term "equilibrium" is used in conjunction with "moisture content" to indicate "moisture content" is related to a particular set of conditions, e.g., temperature, pressure, and so on. As will, be apparent, moisture content commonly refers to a maximum amount of water that can be dissolve by the solvent/solvent mixture given a certain set of conditions.

The term "biphasic fermentation medium" as used herein refers to a two-phase growth medium comprising a fermentation medium (i.e., an aqueous phase) and a suitable amount of a water-immiscible organic extractant.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof. Non-limiting examples of carbon substrates are provided herein and include, but are not limited to, monosaccharides, disaccharides, oligosaccharides, polysaccharides, ethanol, lactate, succinate, glycerol, carbon dioxide, methanol, glucose, fructose, lactose, sucrose, xylose, arabinose, dextrose, cellulose, methane, amino acids, or mixtures thereof.

"Fermentation broth" as used herein means the mixture of water, sugars (fermentable carbon sources), dissolved solids (if present), microorganisms producing alcohol, product alcohol and all other constituents of the material in which product alcohol is being made by the reaction of sugars to alcohol, water and carbon dioxide ($CO_2$) by the microorganisms present. From time to time, as used herein the term "fermentation medium" and "fermented mixture" can be used synonymously with "fermentation broth."

As used herein a "fermentor" refers to any container, containers, or apparatus that are used to ferment a substrate. A fermentor can contain a fermentation medium and microorganism capable of fermentation. The term "fermentation vessel" refers to the vessel in which the fermentation reaction is carried out whereby alcohol such as butanol is made from sugars. "Fermentor" can be used herein interchangeable with "fermentation vessel."

The term "fermentation product" includes any desired product of interest, including, but not limited to 1-butanol, 2-butanol, isobutanol, etc.

The term "sugar" as used herein, refers to oligosaccharides, disaccharides, monosaccharides, and/or mixtures thereof. The term "saccharide" also includes carbohydrates including starches, dextrans, glycogens, cellulose, pentosans, as well as sugars.

The term "fermentable sugar" as used herein, refers to one or more sugars capable of being metabolized by the microorganisms disclosed herein for the production of fermentative alcohol.

The term "undissolved solids" as used herein, means non-fermentable portions of feedstock, for example, germ, fiber, and gluten. For example, the non-fermentable portions of feedstock include the portion of feedstock that remains as solids and can absorb liquid from the fermentation broth.

"Biomass" as used herein refers to a natural product containing a hydrolysable starch that provides a fermentable sugar, including any cellulosic or lignocellulosic material and materials comprising cellulose, and optionally further comprising hemicellulose, lignin, starch, oligosaccharides, disaccharides, and/or monosaccharides. Biomass can also comprise additional components, such as protein and/or lipids. Biomass can be derived from a single source, or biomass can comprise a mixture derived from more than one source. For example, biomass can comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood, and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

"Feedstock" as used herein means a product containing a fermentable carbon source. Suitable feedstock include, but are not limited to, rye, wheat, corn, corn mash, cane, cane mash, sugar cane, barley, cellulosic material, lignocellulosic material, and mixtures thereof.

The term "aerobic conditions" as used herein means growth conditions in the presence of oxygen.

The term "microaerobic conditions" as used herein means growth conditions with low levels of oxygen (i.e., below normal atmospheric oxygen levels).

The term "anaerobic conditions" as used herein means growth conditions in the absence of oxygen.

The term "minimal media" as used herein refers to growth media that contain the minimum nutrients possible for growth, generally without the presence of amino acids. A minimal medium typically contains a fermentable carbon source and various salts, which may vary among microorganisms and growing conditions; these salts generally provide essential elements such as magnesium, nitrogen, phosphorous, and sulfur to allow the microorganism to synthesize proteins and nucleic acids.

The term "defined media" as used herein refers to growth media that have known quantities of all ingredients, e.g., a defined carbon source and nitrogen source, and trace elements and vitamins required by the microorganism.

The term "biocompatibility" as used herein refers to the measure of the ability of a microorganism to utilize glucose in the presence of an extractant. A biocompatible extractant permits the microorganism to utilize glucose. A non-biocompatible (i.e., a biotoxic) extractant does not permit the microorganism to utilize glucose, for example, at a rate greater than about 25% of the rate when the extractant is not present.

The term "toxicity" of solvent as used herein refers to the percentage of butanol-producing microorganisms killed after exposure to the solvent for a prolonged time, for example 24 hours.

The term "free volume" as used herein refers to the proportion of a volume of bulk solvent that is not occupied by solvent molecules.

The term "fatty acid" as used herein, refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

The term "fatty alcohol" as used herein, refers to an alcohol having an aliphatic chain of $C_4$ to $C_{22}$ carbon atoms, which is either saturated or unsaturated.

The term "fatty aldehyde" as used herein, refers to an aldehyde having an aliphatic chain of $C_4$ to $C_{22}$ carbon atoms, which is either saturated or unsaturated.

The term "fatty amide" as used herein, refers to an amide having a long, aliphatic chain of $C_4$ to $C_{22}$ carbon atoms, which is either saturated or unsaturated.

The term "fatty ester" as used herein, refers to an ester having a long aliphatic chain of $C_4$ to $C_{22}$ carbon atoms, which is either saturated or unsaturated.

The term "carboxylic acid" as used herein, refers to any organic compound with the general chemical formula —COOH in which a carbon atom is bonded to an oxygen atom by a double bond to make a carbonyl group (—C═O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

The term "hydrocarbon" as used herein refers to a molecule that contains hydrogen and carbon atoms.

The term "alkane" as used herein refers to a saturated hydrocarbon.

The term "alkene" as used herein refers to an unsaturated hydrocarbon containing at least one carbon to carbon double bond.

The term "branched alkane" as used herein refers to an alkane with alkyl side groups.

The term "isododecane" as used herein refers to an alkane with the longest straight carbon chain of seven. "Isododecane" can also be referred to as "pentamethyl heptane."

"Portion" as used herein, includes a part of a whole or the whole. For example, a portion of fermentation broth includes a part of the fermentation broth as well as the whole (or all) the fermentation broth.

"Partition coefficient" refers to the ratio of the concentration of a compound in the two phases of a mixture of two immiscible solvents at equilibrium. A partition coefficient is a measure of the differential solubility of a compound between two immiscible solvents. Partition coefficient, as used herein, is synonymous with the term distribution coefficient.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene can comprise regulatory sequences and coding sequences that are derived from different sources, or regulatory sequences and coding sequences derived from the same source, but arranged in a manner different than that found in nature. "Endogenous gene" refers to a native gene in its natural location in the genome of a microorganism. A "foreign" gene refers to a gene not normally found in the host microorganism, but that is introduced into the host microorganism by gene transfer. Foreign genes can comprise native genes inserted into a non-native microorganism, or chimeric genes. A "transgene" is a gene that has been introduced into the genome by a transformation procedure.

As used herein, "native" refers to the form of a polynucleotide, gene, or polypeptide as found in nature with its own regulatory sequences, if present.

As used herein the term "coding sequence" or "coding region" refers to a DNA sequence that encodes for a specific amino acid sequence.

As used herein, "endogenous" refers to the native form of a polynucleotide, gene or polypeptide in its natural location in the organism or in the genome of an organism. "Endogenous polynucleotide" includes a native polynucleotide in its natural location in the genome of an organism. "Endogenous gene" includes a native gene in its natural location in the genome of an organism. "Endogenous polypeptide" includes a native polypeptide in its natural location in the organism transcribed and translated from a native polynucleotide or gene in its natural location in the genome of an organism.

The term "heterologous" when used in reference to a polynucleotide, a gene, or a polypeptide refers to a polynucleotide, gene, or polypeptide not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene can be introduced into the host organism by, e.g., gene transfer. A heterologous gene can include a native coding region with non-native regulatory regions that is reintroduced into the native host. For example, a heterologous gene can include a native coding region that is a portion of a chimeric gene including non-native regulatory regions that is reintroduced into the native host. "Heterologous polypeptide" includes a native polypeptide that is reintroduced into the source organism in a form that is different from the corresponding native polypeptide. A "heterologous" polypeptide or polynucleotide can also include an engineered polypeptide or polynucleotide that comprises a difference from the "native" polypeptide or polynucleotide, e.g., a point mutation within the endogenous polynucleotide can result in the production of a "heterologous" polypeptide. As used herein a "chimeric gene," a "foreign gene," and a "transgene," can all be examples of "heterologous" genes.

A "transgene" is a gene that has been introduced into the genome by a transformation procedure.

Organic Extractants

A product alcohol may be recovered from fermentation broth using a number of methods including liquid-liquid extraction. In some embodiments of the processes and systems described herein, an extractant may be used to recover product alcohol from fermentation broth. Extractants used herein may be have, for example, one or more of the following properties and/or characteristics: (i) biocompatible with the microorganisms, (ii) immiscible with the fermentation medium, (iii) a high partition coefficient ($K_d$) for the extraction of product alcohol, (iv) a low partition coefficient for the extraction of nutrients and other side products, (v) a low spreading coefficient, (vi) a high interfacial tension with water, (vii) low viscosity ($\mu$), (viii) high selectivity for product alcohol as compared to, for example, water, (ix) low density ($\rho$) relative to the fermentation medium, (x) boiling point suitable for downstream processing of the extractant and product alcohol, (xi) melting point lower than ambient temperature, (xii) minimal solubility in solids, (xiii) a low tendency to form emulsions with the fermentation medium, (xiv) stability over the fermentation process, (xv) low cost, (xvi) commercial availability, and (xvii) nonhazardous.

In some embodiments, the extractant may be selected based upon certain properties and/or characteristics as described above. For example, viscosity of the extractant can influence the mass transfer properties of the system, i.e., the efficiency with which the product alcohol may be extracted from the aqueous phase to the extractant phase (i.e., organic phase). The density of the extractant can affect phase separation. In some embodiments, the extractant may be liquid at the temperatures of the fermentation process. In some embodiments, selectivity refers to the relative amounts of product alcohol to water taken up by the extractant. The boiling point can affect the cost and method of product alcohol recovery. For example, in the case where butanol is recovered from the extractant phase by distillation, the boiling point of the extractant should be sufficiently low as to enable separation of butanol using available steam while minimizing any thermal degradation or side reactions of the extractant, or the need for vacuum in the distillation process.

The extractant can be biocompatible with the microorganism, that is, nontoxic to the microorganism or toxic only to such an extent that the microorganism is impaired to an acceptable level. In some embodiments, biocompatible refers to the measure of the ability of a microorganism to utilize fermentable carbon sources in the presence of an extractant. The extent of biocompatibility of an extractant may be determined, for example, by the glucose utilization rate of the microorganism in the presence of the extractant and product alcohol. In some embodiments, a non-biocompatible extractant refers to an extractant that interferes with the ability of a microorganism to utilize fermentable carbon sources. For example, a non-biocompatible extractant does not permit the microorganism to utilize glucose at a rate greater than about 25%, greater than about 30%, greater than about 35%, greater than about 40%, greater than about 45%, or greater than about 50% of the rate when the extractant is not present.

One skilled in the art may select an extractant to maximize the desired properties and/or characteristics as described above and to optimize recovery of a product alcohol. One of skill in the art can also appreciate that it may be advantageous to use a mixture of extractants. For example, extractant mixtures may be used to increase the partition coefficient for the product alcohol. Additionally, extractant mixtures may be used to adjust and optimize physical characteristics of the extractant, such as the density, boiling point, and viscosity. For example, the appropriate combination may provide an extractant which has a sufficient affinity for the product alcohol (Kd for butanol), hydrophobicity (log P), sufficient biocompatibility to enable its economical use for removing product alcohol from a fermentative broth (hydrophobicity expressed as log P can indicate biocompatibility), moisture content (tendency to solubilize water) and sufficient selectivity to enable the selective removal of the product alcohol over, for example, water.

In some embodiments, extractants useful in the processes and systems described herein may be organic solvents. In some embodiments, the extractants useful in the processes and systems described herein may be dry solvents. Dry solvents can, for example, be advantageous by attracting butanol and for providing little or no affinity to water. A dry solvent that offers no hydrogen bonding to water, for example, can absorb the alcohol selectively. In some embodiments, the dry solvents may comprise $C_7$ to $C_{22}$ hydrocarbons. In some embodiments, the dry solvents may comprise $C_7$ to $C_{22}$ alkanes or mixtures thereof. In some embodiments, the dry solvents may comprise $C_7$ to $C_{22}$ alkenes or mixtures thereof. The $C_7$ to $C_{22}$ alkanes or alkenes can, for example, be branched alkanes or alkenes (e.g., the alkanes or alkenes may comprise alkyl side groups such as a methyl, an ethyl, a propyl, a butyl, a pentyl, or a hexyl side group). In some embodiments the hydrocarbons can be derivatives of isobutanol. The derivatives of isobutanol can, for example, be selected from triisobutylene, isododecane, diisobutylene, tetraisobutylene, isooctane, 3,4,5,6,6-pentamethyl-2-heptanol, or isohexadecane.

Another advantage of dry solvents is the lower viscosity, higher interfacial tension, and higher thermal and chemical stability that aids in the phase separability and long term reuse. In some embodiments, a dry solvent that accommodates the alkyl portion of butanol may be combined with another extractant that offers affinity in the form of hydrogen bonding, for example, to the hydroxyl portion of butanol such that the mixture provides an optimal balance between selectivity and partitioning over water. Advantages of saturated alkanes include a high interfacial tension, higher thermal and chemical stability, good biocompatibility, a lower melting point, a lower boiling point, a low density, a low viscosity, and a low tendency to form emulsions. Another advantage with regard to higher partition coefficients, without intending to be limited by theory, some examples indicate that solvents with hydrogen bonding characteristics and/or high free volume have a high butanol partition coefficient ($K_d$). Increased hydrogen bonding characteristics can be achieved by having a greater number of hydrogen bonding sites per molecule. In some embodiments, compounds including nitrogen, oxygen, phosphorus, and sulfur are used to provide hydrogen bonding sites. Free volume in the organic phase can be achieved using solvents whose molecules have a high degree of branching and do not pack closely.

In some embodiments, the organic extractant composition further comprises a second solvent. The second solvent can, for example, be an organic solvent selected from the group consisting of saturated, mono-unsaturated, polyunsaturated, branched (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, $C_7$ to $C_{22}$ ethers, and mixtures thereof. The second solvent may also be an organic solvent selected from the group consisting of saturated, mono-unsaturated, poly-unsaturated, branched (and mixtures thereof) $C_4$ to $C_{22}$ fatty alcohols, $C_4$ to $C_{28}$ fatty acids, esters of $C_4$ to $C_{28}$ fatty acids, $C_4$ to $C_{22}$ fatty aldehydes, and mixtures thereof. In some embodiments, the extractant may include a first dry solvent and a second solvent selected from $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, $C_7$ to $C_{22}$ ethers, $C_7$ to $C_{11}$ fatty alcohols, $C_7$ to $C_{11}$ fatty acids, esters of $C_7$ to $C_{11}$ fatty acids, $C_7$ to $C_{11}$ fatty aldehydes, and mixtures thereof. In some embodiments, the second solvent may be carboxylic acids. In some embodiments, the second solvent may be an organic solvent such as oleyl alcohol, phenyl alcohol, Docosanol (behenyl alcohol), cetyl alcohol, lauryl alcohol (also referred to as 1-dodecanol), myristyl alcohol, stearyl alcohol, oleic acid, lauric acid, myristic acid, stearic acid, octanoic acid, decanoic acid, undecanoic acid, methyl myristate, methyl oleate, 1-nonanol, 1-decanol, 2-undecanol, 1-nonanal, 1-undecanol, undecanal, isododecanol, lauric aldehyde, 2-methylundecanal, oleamide, linoleamide, palmitamide, stearylamide, 2-ethyl-1-hexanol, 2-hexyl-1-decanol, 2-octyl-1-dodecanol, or mixtures thereof. Other examples include, but are not limited to phosphates, phosphines, phosphinates, amides, alkylphenols, salicylates, and parabens.

In some embodiments, the extractant may be a mixture of biocompatible and non-biocompatible extractants. Examples of mixtures of biocompatible and non-biocompatible extractants include, but are not limited to, isododecane and 2-ethyl-1-hexanol, isododecane and butyl octanol, isododecane and nonanol, isododecane and 1-undecanol, isododecane, and 2-undecanol, isododecane, and 1-nonanal, isododecane and decanol, isododecane and dodecanol, oleyl alcohol and nonanol, oleyl alcohol and 1-undecanol, oleyl alcohol and 2-undecanol, oleyl alcohol and 1-nonanal, oleyl alcohol and decanol, and oleyl alcohol and dodecanol. Additional examples of biocompatible and non-biocompatible extractants are described in U.S. Patent Application Publication No. 2009/0305370 and U.S. Patent Application Publication No. 2011/0097773; the entire contents of each herein incorporated by reference. In some embodiments, biocompatible extractants may have high atmospheric boiling points. For example, biocompatible extractants may have atmospheric boiling points greater than the atmospheric boiling point of water.

In some embodiments, a hydrophilic solute may be added to fermentation broth that is contacted with an extractant. The presence of a hydrophilic solute in the aqueous broth phase may improve phase separation and may increase the fraction of product alcohol that partitions into the organic extractant phase. Examples of a hydrophilic solute may include, but are not limited to, polyhydroxylated, polycarboxylic, polyol compounds and dissociating ionic salts. Sugars such as glucose, fructose, sucrose, maltose, and oligosaccharides may serve as a hydrophilic solute. Other polyhydroxylated compounds may include glycerol, ethylene glycol, propanediol, polyglycerol, and hydroxylated fullerene. Polycarboxylic compounds may include citric acid, tartaric acid, maleic acid, succinic acid, polyacrylic acid, and sodium, potassium, ammonium salts thereof. Ionic salts that may be used as a hydrophilic solute in fermentation broth comprise cations that include sodium, potassium, ammonium, magnesium, calcium, zinc, and anions that include sulfate, phosphate, chloride, nitrate. The level of hydrophilic solute in fermentation broth may be selected by one skilled in the art to maximize the transfer of product alcohol out of the fermentation broth phase and into a contacting organic extractant phase while not negatively impacting the growth and/or productivity of the product alcohol-producing microorganisms. High levels of hydrophilic solute may impose osmotic stress and/or toxicity to microorganisms in fermentation broth. One skilled in the art may use any number of known methods to determine an optimal level of hydrophilic solute to minimize the effects of osmotic stress and/or toxicity on microorganisms.

In some embodiments, the hydrophobic solute may be contacted with the extractant after the extractant is contacted with and separated from the fermentation broth as will be described in further detail in the section captioned "discussion of sample solvent mixture preparation and extraction" below. Embodiment such as these may be considered two step processes as two different extractions are performed.

In some embodiments, the extractant may comprise an aromatic compound. In some embodiments, the extractant may comprise alkyl substituted benzenes including, but not limited to, cumene, para-cymene, meta-cumene, meta-diisopropylbenzene, para-diisopropylbenzene, triisopropylbenzene, tri-sec-butyl-benzene, triethylbenzene, ethyl butyl benzene, tert-butylstyrene. An advantage of using an alkyl substituted benzene is the comparatively higher butanol affinity relative to most other hydrocarbons. In addition, isopropyl, or sec-butyl or isobutyl substituted benzenes may offer a particular advantage in butanol affinity over other substituted benzenes. Another advantage is the lower viscosity, higher interfacial tension, and lower density and higher thermal and chemical stability that aids in the phase separability and long term reuse.

In embodiments in accordance with the present disclosure, a solvent mixture is used to extract alcohol, such as butanol or other fusels from an aqueous solution, such as a fermentation broth. For example, a solvent mixture comprises one or more solvents, such as a first and second solvent. The first and second solvents, as well as any additional solvents, can be selected to tailor the solvent mixture's properties, although the solvents included in the solvent mixture do not behave ideally. In examples, characteristics such as hydrophobicity, moisture content, alcohol affinity, toxicity to a microorganism are considered when selecting which solvents to combine. In implementations, a solvent mixture may exhibit properties that are not indicated by the properties of the individual solvents (e.g., hydrophobicity, moisture content, alcohol affinity, toxicity) and the mole fraction of the individual solvents in the solvent mixture. For example, combining a first solvent with a high hydrophobicity with a second solvent that is, in comparison to the first solvent, less hydrophobic can result in a solvent mixture that exhibits synergistic alcohol extraction capability beyond that expected for the solvent mixture based on the first solvent's properties and mole fraction in the solvent mixture and the second solvent's properties and its (the second solvent's) mole fraction in the solvent mixture. For example, a solvent mixture of corn oil fatty acid (COFA) and isododecane exhibits lower equilibrium moisture content than that expected based on the properties of COFA and isododecane on an individual basis. In embodiments, such as this the aqueous solution that includes the alcohol is contacted with the solvent mixture to extract the alcohol into the solvent mixture.

Distillation of Dry Solvents

An extractant containing butanol (e.g., isobutanol) and water can be stripped to form an extractant that is lean in butanol. In this ternary system, there may not exist a method to selectively strip butanol over water because the two components form what is known as a minimum boiling azeotrope. Therefore, the minimum energy associated with stripping the extractant will include the latent heat of vaporizing the butanol along with the latent heat of co-vaporizing water vapor. Because the latent heat of water vapor is greater than (e.g., almost 4 times as much) the latent heat of butanol on a mass basis, water co-vaporization can result in an increased energy demand to remove the butanol from the extractant. The overhead vapor generated in stripping the extractant may therefore contain a mixture of butanol and water and may require condensation, decantation and further distillation to isolate a purified butanol product that is suitable for biofuel applications. In the case of a dry extractant, the water content is significantly reduced and so is the co-vaporization energy contribution to the total stripping energy needed to remove butanol. Furthermore, the overhead vapor generated from stripping butanol from a dry extractant may upon condensation form a butanol product with a water content that is within some specified range for biofuel application and in that instance, no further distillation of the stream may be required.

In some embodiments, an extractant containing butanol may be phase separated from fermentation broth and distilled in a column operating under vacuum. This distillation may operate with reflux in order to maintain a distillate of high purity butanol that contains very little extractant. The bottoms may comprise a portion of the butanol contained in the distillation feed such that the reboiling temperature under vacuum is suitable for delivering heat indirectly from available steam. Distillation may be carried out with a partial condenser where only reflux liquid is condensed, and a vapor distillate of substantially butanol composition may be directed into the bottom of a rectification column that is simultaneously fed a butanol stream decanted from condensed beer column overhead vapor. An advantage of this type of distillation is that the need for a reboiler to purify the decanted butanol stream is eliminated by heat integrating the vapor generated from stripping butanol out of the extractant.

Conversion of Isobutanol to Isododecane

In some embodiments, a stream of high purity butanol (e.g., isobutanol) produced can be utilized to produce a derivative of isobutanol. The derivative of isobutanol can, for example, be tri-isobutylene or isododecane. The stream of high purity butanol can be taken after distillation into a vessel. In the vessel, the isobutanol can be catalytically converted to tri-isobutylene and/or isododecane.

Figure 8:
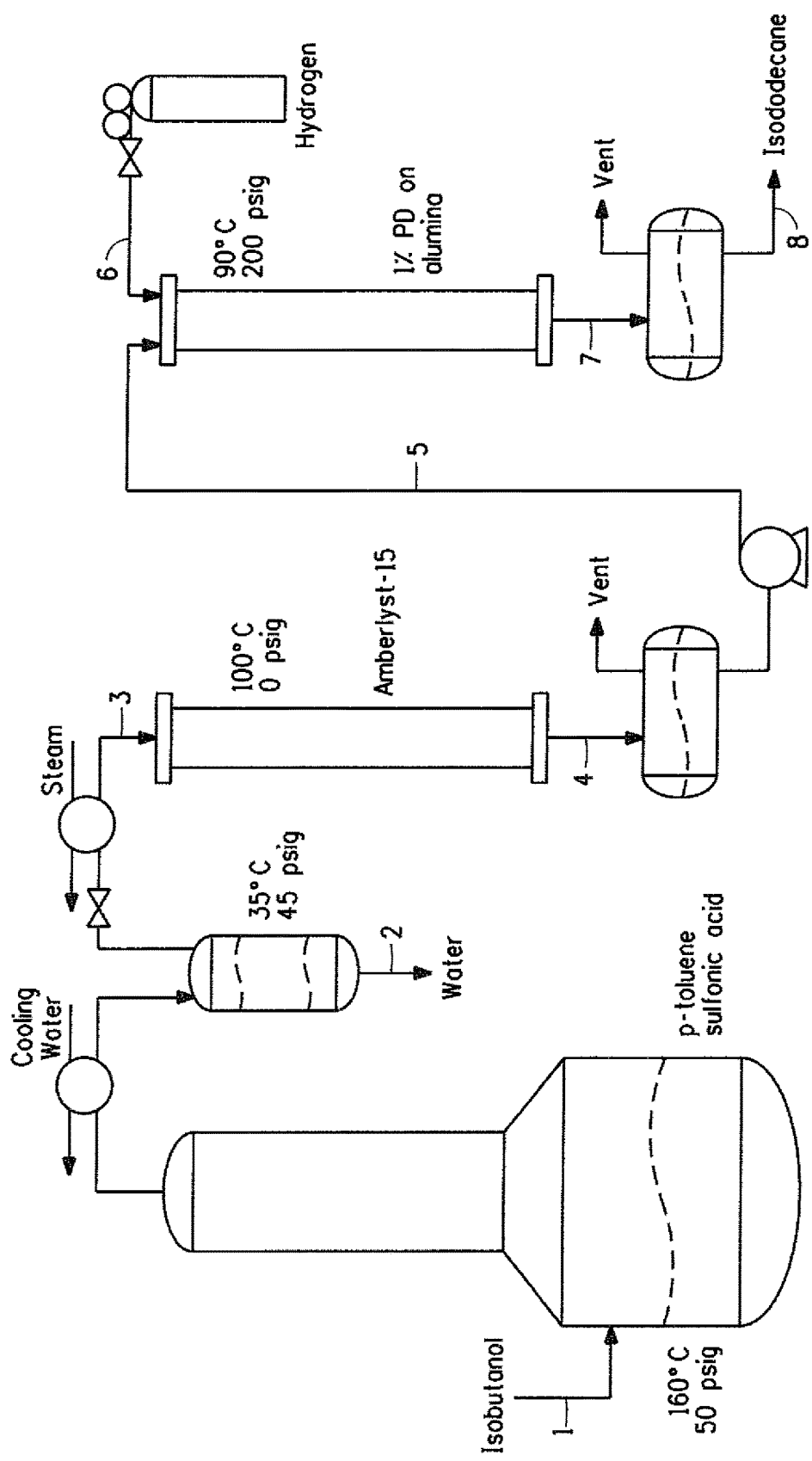
FIG. 8 shows a schematic of a process for converting isobutanol to derivatives of isobutanol, e.g., triisobutylene, diisobutylene, tetraisobutylene, and isododecane.

Isobutanol can be converted to triisobutylene and/or isododecane as illustrated in FIG. 8. FIG. 8 depicts a typical process configuration for converting isobutanol to a higher alkane comprising predominantly 2,2,4,6,6-pentamethylheptane. Isobutanol is preheated and fed via stream 1 to a reaction vessel that contains 2.5% para toluene sulfonic acid operating at 160° C. and 50 psig. A vapor stream is generated and is passed up through a rectification column before being partially condensed and decanted into two liquid phases at 35° C. and 45 psig. The upper phase is organic comprising mostly isobutylene and is returned to the top of the column as reflux while the lower aqueous phase is removed as stream 2. Uncondensed vapors are let down in pressure across a valve and reheated by a steam exchanger to form isobutylene vapor stream 3 that is fed into a tubular oligomerization reactor packed with Amberlyst-15 catalyst in the form of 0.5 mm beads operating at 100° C. and near atmospheric pressure. At a weight hourly space velocity of 1 g isobutylene per g catalyst per hour, 8.6% of the isobutylene is converted to diisobutylene, 81.6% to triisobutylene and 5.8% to tetraisobutylene, while 4% remains unconverted. The reactor effluent stream 4 is flashed in a drum to safely vent off the unreacted isobutylene and the mixed isomers of isobutylene oligomers is pumped via stream 5 to a trickle bed hydrogenation reactor along with an excess feed of hydrogen gas stream 6 sourced from cylinder storage. The conversion of olefins is quantitative and the hydrogenation reactor effluent stream 7 is flashed in a drum to safely vent off unreacted hydrogen gas and produce a liquid product steam 8 comprising predominantly 2,2,4,6,6-pentamethylheptane. Steps for the conversion of isobutanol to triisobutylene and isododecane (2,2,4,6,6-pentamethylheptane) are known in the art, see, for e.g., Alcantara et al., Reactive Funct. Polymers 45:19-27 (2000); Ludwig et al., J. Catalysis 284:148-56 (2011); and U.S. Pat. No. 5,625,109.

Recombinant Microorganisms

While not wishing to be bound by theory, it is believed that the processes described herein are useful in conjunction with any alcohol producing microorganism, particularly recombinant microorganisms which produce alcohol.

Recombinant microorganisms which produce alcohol are also known in the art (e.g., Ohta et al., *Appl. Environ. Microbiol.* 57:893-900 (1991); Underwood et al., *Appl. Environ. Microbiol.* 68:1071-81 (2002); Shen and Liao, *Metab. Eng.* 10:312-20 (2008); Hahnai et al., *Appl. Environ.* 73:7814-8 (2007); U.S. Pat. No. 5,514,583; U.S. Pat. No. 5,712,133; International Publication No. WO 1995/028476; Feldmann et al., *Appl. Microbiol. Biotechnol.* 38:354-61 (1992); Zhang et al., *Science* 267:240-3 (1995); U.S. Patent Publication No. 2007/0031918A1; U.S. Pat. No. 7,223,575; U.S. Pat. No. 7,741,119; U.S. Patent Publication No. 2009/0203099A1; U.S. Patent Publication No. 2009/0246846A1; and International Publication No. WO 2010/075241, which are herein incorporated by reference).

For example, the metabolic pathways of microorganisms may be genetically modified to produce butanol. These pathways may also be modified to reduce or eliminate undesired metabolites, and thereby improve yield of the product alcohol. The production of butanol by a microorganism is disclosed, for example, in U.S. Pat. Nos. 7,851,188; 7,993,889; 8,178,328, 8,206,970; U.S. Patent Application Publication Nos. 2007/0292927; 2008/0182308; 2008/0274525; 2009/0305363; 2009/0305370; 2011/0250610; 2011/0313206; 2011/0111472; 2012/0258873; and U.S. patent application Ser. No. 13/428,585, the entire contents of each are herein incorporated by reference. In some embodiments, microorganisms comprise a butanol biosynthetic pathway or a biosynthetic pathway for a butanol isomer such as 1-butanol, 2-butanol, or isobutanol. In some embodiments, the biosynthetic pathway converts pyruvate to a fermentative product. In some embodiments, the biosynthetic pathway converts pyruvate as well as amino acids to a fermentative product. In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism.

In some embodiments, the microorganism may be bacteria, cyanobacteria, filamentous fungi, or yeasts. Suitable microorganisms capable of producing product alcohol (e.g., butanol) via a biosynthetic pathway include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma,* or *Saccharomyces*. In one embodiment, recombinant microorganisms may be selected from the group consisting of *Escherichia coli, Alcaligenes eutrophus, Bacillus licheniformis, Paenibacillus macerans, Rhodocuccus erythropolis, Pseudomonas putida, Lactobacillus plantarum, Enterococcus faecium, Enterococcus gallinarium, Enterococcus faecalis, Bacillus subtilis, Candida sonorensis, Candida methanosorbosa, Kluyveromyces lactis, Kluyveromyces marxianus, Kluveromyces thermotolerans, Issatchenkia orientalis, Debaryomyces hansenii,* and *Saccharomyces cerevisiae*. In one embodiment, the genetically modified microorganism is yeast. In one embodiment, the genetically modified microorganism is a crabtree-positive yeast selected from *Saccharomyces, Zygosaccharomyces, Schizosaccharomyces, Dekkera, Torulopsis, Brettanomyces,* and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Saccharomyces uvarum, Saccharomyces castelli, Zygosaccharomyces rouxii, Zygosaccharomyces bailli,* and *Candida glabrata.*

In some embodiments, the host cell is *Saccharomyces cerevisiae*. *Saccharomyces cerevisiae* are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

In some embodiments, the microorganism may be immobilized or encapsulated. For example, the microorganism may be immobilized or encapsulated using alginate, calcium alginate, or polyacrylamide gels, or through the induction of biofilm formation onto a variety of high surface area support matrices such as diatomite, celite, diatomaceous earth, silica gels, plastics, or resins. In some embodiments, ISPR may be used in combination with immobilized or encapsulated microorganisms. This combination may improve productivity such as specific volumetric productivity, metabolic rate, product alcohol yields, tolerance to product alcohol. In addition, immobilization and encapsulation may minimize the effects of the process conditions such as shearing on the microorganisms.

Biosynthetic pathways for the production of isobutanol that may be used include those as described by Donaldson et al. in U.S. Pat. No. 7,851,188; U.S. Pat. No. 7,993,388; and International Publication No. WO 2007/050671, which are incorporated herein by reference. In one embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by acetohydroxy acid reductoisomerase;

c) the 2,3-dihydroxyisovalerate from step b) to α-ketoisovalerate, which may be catalyzed, for example, by acetohydroxy acid dehydratase;

d) the α-ketoisovalerate from step c) to isobutyraldehyde, which may be catalyzed, for example, by a branched-chain α-keto acid decarboxylase; and, e) the isobutyraldehyde from step d) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by ketol-acid reductoisomerase;

c) the 2,3-dihydroxyisovalerate from step b) to α-ketoisovalerate, which may be catalyzed, for example, by dihydroxyacid dehydratase;

d) the α-ketoisovalerate from step c) to valine, which may be catalyzed, for example, by transaminase or valine dehydrogenase;

e) the valine from step d) to isobutylamine, which may be catalyzed, for example, by valine decarboxylase;

f) the isobutylamine from step e) to isobutyraldehyde, which may be catalyzed by, for example, omega transaminase; and, g) the isobutyraldehyde from step f) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by acetohydroxy acid reductoisomerase;

c) the 2,3-dihydroxyisovalerate from step b) to α-ketoisovalerate, which may be catalyzed, for example, by acetohydroxy acid dehydratase;

d) the α-ketoisovalerate from step c) to isobutyryl-CoA, which may be catalyzed, for example, by branched-chain keto acid dehydrogenase;

e) the isobutyryl-CoA from step d) to isobutyraldehyde, which may be catalyzed, for example, by acylating aldehyde dehydrogenase; and, f) the isobutyraldehyde from step e) to isobutanol, which may be catalyzed, for example, by a branched-chain alcohol dehydrogenase.

Biosynthetic pathways for the production of 1-butanol that may be used include those described in U.S. Patent Application Publication No. 2008/0182308 and WO2007/041269, which are incorporated herein by reference. In one embodiment, the 1-butanol biosynthetic pathway comprises the following substrate to product conversions:

a) acetyl-CoA to acetoacetyl-CoA, which may be catalyzed, for example, by acetyl-CoA acetyltransferase;

b) the acetoacetyl-CoA from step a) to 3-hydroxybutyryl-CoA, which may be catalyzed, for example, by 3-hydroxybutyryl-CoA dehydrogenase;

c) the 3-hydroxybutyryl-CoA from step b) to crotonyl-CoA, which may be catalyzed, for example, by crotonase;

d) the crotonyl-CoA from step c) to butyryl-CoA, which may be catalyzed, for example, by butyryl-CoA dehydrogenase;

e) the butyryl-CoA from step d) to butyraldehyde, which may be catalyzed, for example, by butyraldehyde dehydrogenase; and, f) the butyraldehyde from step e) to 1-butanol, which may be catalyzed, for example, by butanol dehydrogenase.

Biosynthetic pathways for the production of 2-butanol that may be used include those described by Donaldson et al. in U.S. Pat. No. 8,206,970; U.S. Patent Application Publication Nos. 2007/0292927 and 2009/0155870; International Publication Nos. WO 2007/130518 and WO 2007/130521, all of which are incorporated herein by reference. In one embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetonin aminase;

d) the 3-amino-2-butanol from step c) to 3-amino-2-butanol phosphate, which may be catalyzed, for example, by aminobutanol kinase;

e) the 3-amino-2-butanol phosphate from step d) to 2-butanone, which may be catalyzed, for example, by aminobutanol phosphate phosphorylase; and, f) the 2-butanone from step e) to 2-butanol, which may be catalyzed, for example, by butanol dehydrogenase.

In another embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin to 2,3-butanediol from step b), which may be catalyzed, for example, by butanediol dehydrogenase;

d) the 2,3-butanediol from step c) to 2-butanone, which may be catalyzed, for example, by dial dehydratase; and, e) the 2-butanone from step d) to 2-butanol, which may be catalyzed, for example, by butanol dehydrogenase.

Biosynthetic pathways for the production of 2-butanone that may be used include those described in U.S. Pat. No. 8,206,970 and U.S. Patent Application Publication Nos. 2007/0292927 and 2009/0155870, which are incorporated herein by reference. In one embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetonin aminase;

d) the 3-amino-2-butanol from step c) to 3-amino-2-butanol phosphate, which may be catalyzed, for example, by aminobutanol kinase; and, e) the 3-amino-2-butanol phosphate from step d) to 2-butanone, which may be catalyzed, for example, by aminobutanol phosphate phosphorylase.

In another embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin which may be catalyzed, for example, by acetolactate decarboxylase;

c) the acetoin from step b) to 2,3-butanediol, which may be catalyzed, for example, by butanediol dehydrogenase;

d) the 2,3-butanediol from step c) to 2-butanone, which may be catalyzed, for example, by diol dehydratase.

The terms "acetohydroxyacid synthase," "acetolactate synthase," and "acetolactate synthetase" (abbreviated "ALS") are used interchangeably herein to refer to an enzyme that catalyzes the conversion of pyruvate to acetolactate and $CO_2$. Example acetolactate synthases are known by the EC number 2.2.1.6 (Enzyme Nomenclature 1992, Academic Press, San Diego). These enzymes are available from a number of sources, including, but not limited to, *Bacillus subtilis* (GenBank Nos: CAB07802.1, Z99122, NCBI (National Center for Biotechnology Information) amino acid sequence, NCBI nucleotide sequence, respectively), CAB15618, *Klebsiella pneumoniae* (GenBank Nos: AAA25079, M73842), and *Lactococcus lactis* (GenBank Nos: AAA25161, L16975)

The term "ketol-acid reductoisomerase" ("KARI"), "acetohydroxy acid isomeroreductase," and "acetohydroxy acid reductoisomerase" will be used interchangeably and refer to enzymes capable of catalyzing the reaction of (S)-acetolactate to 2,3-dihydroxyisovalerate. Example KARI enzymes may be classified as EC number EC 1.1.1.86 (Enzyme Nomenclature 1992, Academic Press, San Diego), and are available from a vast array of microorganisms, including, but not limited to, *Escherichia coli* (GenBank Nos: NP_418222, NC_000913), *Saccharomyces cerevisiae* (GenBank Nos: NP_013459, NC_001144), *Methanococcus maripaludis* (GenBank Nos: CAF30210, BX957220), *Bacillus subtilis* (GenBank Nos: CAB14789, Z99118), and *Anaerostipes caccae*. Ketol-acid reductoisomerase (KARI) enzymes are described in U.S. Pat. Nos. 7,910,342 and 8,129,162; U.S. Patent Application Publication Nos. 2008/0261230, 2009/0163376, 2010/0197519, PCT Application Publication No. WO/2011/041415, PCT Application Publication No. WO2012/129555; and U.S. Provisional Application No. 61/705,977, filed on Sep. 26, 2012, all of which are incorporated herein by reference. Examples of KARIs disclosed therein are those from *Lactococcus lactis, Vibrio cholera, Pseudomonas aeruginosa* PAO1, and *Pseudomonas fluorescens* PF5 mutants. In some embodiments, the KARI utilizes NADH. In some embodiments, the KARI utilizes NADPH. In some embodiments, the KARI utilizes NADH or NADPH.

The term "acetohydroxy acid dehydratase" and "dihydroxyacid dehydratase" ("DHAD") refers to an enzyme that catalyzes the conversion of 2,3-dihydroxyisovalerate to α-ketoisovalerate. Example acetohydroxy acid dehydratases are known by the EC number 4.2.1.9. Such enzymes are available from a vast array of microorganisms, including, but not limited to, *E. coli* (GenBank Nos: YP_026248, NC000913), *Saccharomyces cerevisiae* (GenBank Nos: NP_012550, NC_001142), *M. maripaludis* (GenBank Nos: CAF29874, BX957219), *B. subtilis* (GenBank Nos: CAB14105, Z99115), *L. lactis*, and *N. crassa*. U.S. Patent Application Publication No. 2010/0081154, U.S. Pat. No. 7,851,188, and U.S. Pat. No. 8,241,878, which are incorporated herein by reference in their entireties, describe dihydroxyacid dehydratases (DHADs), including a DHAD from *Streptococcus mutans* and variants thereof.

The term "branched-chain α-keto acid decarboxylase," "α-ketoacid decarboxylase," "α-ketoisovalerate decarboxylase," or "2-ketoisovalerate decarboxylase" ("KIVD") refers to an enzyme that catalyzes the conversion of α-ketoisovalerate to isobutyraldehyde and $CO_2$. Example branched-chain α-keto acid decarboxylases are known by the EC number 4.1.1.72 and are available from a number of sources, including, but not limited to, *Lactococcus lactis* (GenBank Nos: AAS49166, AY548760; CAG34226, AJ746364), *Salmonella typhimurium* (GenBank Nos: NP_461346, NC_003197), *Clostridium acetobutylicum* (GenBank Nos: NP_149189, NC_001988), *M. caseolyticus*, and *L. grayi*.

The term "branched-chain alcohol dehydrogenase" ("ADH") refers to an enzyme that catalyzes the conversion of isobutyraldehyde to isobutanol. Example branched-chain alcohol dehydrogenases are known by the EC number 1.1.1.265, but may also be classified under other alcohol dehydrogenases (specifically, EC 1.1.1.1 or 1.1.1.2). Alcohol dehydrogenases may be NADPH dependent or NADH dependent. Such enzymes are available from a number of sources, including, but not limited to, *S. cerevisiae* (GenBank Nos: NP_010656, NC_001136, NP_014051, NC_001145), *E. coli* (GenBank Nos: NP_417484, NC_000913), *C. acetobutylicum* (GenBank Nos: NP_349892, NC_003030; NP_349891, NC_003030). U.S. Patent Application Publication No. 2009/0269823 describes SadB, an alcohol dehydrogenase (ADH) from *Achromobacter xylosoxidans*. Alcohol dehydrogenases can also include horse liver ADH and *Beijerinkia indica* ADH, as described by U.S. Patent Application Publication No. 2011/0269199, which is incorporated herein by reference in its entirety.

The term "butanol dehydrogenase" refers to a polypeptide (or polypeptides) having an enzyme activity that catalyzes the conversion of isobutyraldehyde to isobutanol or the conversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* (GenBank Nos: CAD36475, AJ491307). The NADP dependent enzymes are known as EC 1.1.1.2 and are available, for example, from *Pyrococcus furiosus* (GenBank Nos: AAC25556, AF013169). Additionally, a butanol dehydrogenase is available from *Escherichia coli* (GenBank Nos: NP_417484, NC_000913) and a cyclohexanol dehydrogenase is available from *Acinetobacter* sp. (GenBank Nos: AAG10026, AF282240). The term "butanol dehydrogenase" also refers to an enzyme that catalyzes the conversion of butyraldehyde to 1-butanol, using either NADH or NADPH as cofactor. Butanol dehydrogenases are available from, for example, *C. acetobutylicum* (GenBank NOs: NP_149325, NC_001988; note: this enzyme possesses both aldehyde and alcohol dehydrogenase activity); NP_349891, NC_003030; and NP_349892, NC_003030) and *E. coli* (GenBank NOs: NP_417484, NC_000913).

The term "branched-chain keto acid dehydrogenase" refers to an enzyme that catalyzes the conversion of α-ketoisovalerate to isobutyryl-CoA (isobutyryl-coenzyme A), typically using $NAD^+$ (nicotinamide adenine dinucleotide) as an electron acceptor. Example branched-chain keto acid dehydrogenases are known by the EC number 1.2.4.4. Such branched-chain keto acid dehydrogenases are comprised of four subunits and sequences from all subunits are available from a vast array of microorganisms, including, but not limited to, *B. subtilis* (GenBank Nos: CAB14336, Z99116; CAB14335, Z99116; CAB14334, Z99116; and CAB14337, Z99116) and *Pseudomonas putida* (GenBank Nos: AAA65614, M57613; AAA65615, M57613; AAA65617, M57613; and AAA65618, M57613).

The term "acylating aldehyde dehydrogenase" refers to an enzyme that catalyzes the conversion of isobutyryl-CoA to isobutyraldehyde, typically using either NADH or NADPH as an electron donor. Example acylating aldehyde dehydrogenases are known by the EC numbers 1.2.1.10 and 1.2.1.57. Such enzymes are available from multiple sources, including, but not limited to, *Clostridium beijerinckii* (GenBank Nos: AAD31841, AF157306), *C. acetobutylicum* (GenBank Nos: NP_149325, NC_001988; NP_149199, NC_001988), *P. putida* (GenBank Nos: AAA89106, U13232), and *Thermus thermophilus* (GenBank Nos: YP_145486, NC_006461).

The term "transaminase" refers to an enzyme that catalyzes the conversion of α-ketoisovalerate to L-valine, using either alanine or glutamate as an amine donor. Example transaminases are known by the EC numbers 2.6.1.42 and 2.6.1.66. Such enzymes are available from a number of sources. Examples of sources for alanine-dependent enzymes include, but are not limited to, *E. coli* (GenBank Nos: YP_026231, NC_000913) and *Bacillus licheniformis* (GenBank Nos: YP_093743, NC_006322). Examples of sources for glutamate-dependent enzymes include, but are not limited to, *E. coli* (GenBank Nos: YP_026247, NC_000913), *Saccharomyces cerevisiae* (GenBank Nos: NP_012682, NC_001142) and *Methanobacterium thermoautotrophicum* (GenBank Nos: NP_276546, NC_000916).

The term "valine dehydrogenase" refers to an enzyme that catalyzes the conversion of α-ketoisovalerate to L-valine, typically using NAD(P)H as an electron donor and ammonia as an amine donor. Example valine dehydrogenases are known by the EC numbers 1.4.1.8 and 1.4.1.9 and such enzymes are available from a number of sources, including, but not limited to, *Streptomyces coelicolor* (GenBank Nos: NP_628270, NC_003888) and *B. subtilis* (GenBank Nos: CAB14339, Z99116).

The term "valine decarboxylase" refers to an enzyme that catalyzes the conversion of L-valine to isobutylamine and $CO_2$. Example valine decarboxylases are known by the EC number 4.1.1.14. Such enzymes are found in *Streptomyces*, such as for example, *Streptomyces viridifaciens* (GenBank Nos: AAN10242, AY116644).

The term "omega transaminase" refers to an enzyme that catalyzes the conversion of isobutylamine to isobutyraldehyde using a suitable amino acid as an amine donor. Example omega transaminases are known by the EC number 2.6.1.18 and are available from a number of sources, including, but not limited to, *Alcaligenes denitrificans* (AAP92672, AY330220), *Ralstonia eutropha* (GenBank Nos: YP_294474, NC_007347), *Shewanella oneidensis* (GenBank Nos: NP_719046, NC_004347), and *P. putida* (GenBank Nos: AAN66223, AE016776).

The term "acetyl-CoA acetyltransferase" refers to an enzyme that catalyzes the conversion of two molecules of acetyl-CoA to acetoacetyl-CoA and coenzyme A (CoA). Example acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1, NC_003030; NP_149242, NC_001988, *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Example hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA. Examples may be classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314, NC_003030), *B. subtilis* (GenBank NOs: AAB09614, U29084), *Ralstonia eutropha* (GenBank NOs: YP_294481, NC_007347), and *Alcaligenes eutrophus* (GenBank NOs: AAA21973, J04987).

The term "crotonase" refers to an enzyme that catalyzes the conversion of 3-hydroxybutyryl-CoA to crotonyl-CoA and H$_2$O. Example crotonases may have a substrate preference for (S)-3-hydroxybutyryl-CoA or (R)-3-hydroxybutyryl-CoA and may be classified as E.C. 4.2.1.17 and E.C. 4.2.1.55, respectively. Crotonases are available from a number of sources, for example, *E. coli* (GenBank NOs: NP_415911, NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase" refers to an enzyme that catalyzes the conversion of crotonyl-CoA to butyryl-CoA. Example butyryl-CoA dehydrogenases may be NADH-dependent, NADPH-dependent, or flavin-dependent and may be classified as E.C. 1.3.1.44, E.C. 1.3.1.38, and E.C. 1.3.99.2, respectively. Butyryl-CoA dehydrogenases are available from a number of sources, for example, *C. acetobutylicum* (GenBank NOs: NP_347102, NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841, AF157306) and *C. acetobutylicum* (GenBank NOs: NP_149325, NC_001988).

The term "isobutyryl-CoA mutase" refers to an enzyme that catalyzes the conversion of butyryl-CoA to isobutyryl-CoA. This enzyme uses coenzyme B$_{12}$ as cofactor. Example isobutyryl-CoA mutases are known by the EC number 5.4.99.13. These enzymes are found in a number of *Streptomyces*, including, but not limited to, *Streptomyces cinnamonensis* (GenBank Nos: AAC08713, U67612; CAB59633, AJ246005), *S. coelicolor* (GenBank Nos: CAB70645, AL939123; CAB92663, AL939121), and *Streptomyces avermitilis* (GenBank Nos: NP_824008, NC_003155; NP_824637, NC_003155).

The term "acetolactate decarboxylase" refers to a polypeptide (or polypeptides) having an enzyme activity that catalyzes the conversion of alpha-acetolactate to acetoin. Example acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (GenBank Nos: AAU43774, AY722056).

The term "acetoin aminase" or "acetoin transaminase" refers to a polypeptide (or polypeptides) having an enzyme activity that catalyzes the conversion of acetoin to 3-amino-2-butanol. Acetoin aminase may utilize the cofactor pyridoxal 5'-phosphate or NADH (reduced nicotinamide adenine dinucleotide) or NADPH (reduced nicotinamide adenine dinucleotide phosphate). The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH dependent acetoin aminase, also known as amino alcohol dehydrogenase, is described by Ito, et al. (U.S. Pat. No. 6,432,688). An example of a pyridoxal-dependent acetoin aminase is the amine:pyruvate aminotransferase (also called amine:pyruvate transaminase) described by Shin and Kim (J. Org. Chem. 67:2848-2853, 2002).

The term "acetoin kinase" refers to a polypeptide (or polypeptides) having an enzyme activity that catalyzes the conversion of acetoin to phosphoacetoin. Acetoin kinase may utilize ATP (adenosine triphosphate) or phosphoenolpyruvate as the phosphate donor in the reaction. Enzymes that catalyze the analogous reaction on the similar substrate dihydroxyacetone, for example, include enzymes known as EC 2.7.1.29 (Garcia-Alles, et al., *Biochemistry* 43:13037-13046, 2004).

The term "acetoin phosphate aminase" refers to a polypeptide (or polypeptides) having an enzyme activity that catalyzes the conversion of phosphoacetoin to 3-amino-2-butanol O-phosphate. Acetoin phosphate aminase may use the cofactor pyridoxal 5'-phosphate, NADH or NADPH. The resulting product may have (R) or (S) stereochemistry at the 3-position. The pyridoxal phosphate-dependent enzyme may use an amino acid such as alanine or glutamate. The NADH and NADPH-dependent enzymes may use ammonia as a second substrate. Although there are no reports of enzymes catalyzing this reaction on phosphoacetoin, there is a pyridoxal phosphate-dependent enzyme that is proposed to carry out the analogous reaction on the similar substrate serinol phosphate (Yasuta, et al., *Appl. Environ. Microbial.* 67:4999-5009, 2001).

The term "aminobutanol phosphate phospholyase," also called "amino alcohol O-phosphate lyase," refers to a polypeptide (or polypeptides) having an enzyme activity that catalyzes the conversion of 3-amino-2-butanol O-phosphate to 2-butanone. Amino butanol phosphate phospho-lyase may utilize the cofactor pyridoxal 5'-phosphate. There are reports of enzymes that catalyze the analogous reaction on the similar substrate 1-amino-2-propanol phosphate (Jones, et al., *Biochem J.* 134:167-182, 1973). U.S. Patent Application Publication No. 2007/0259410 describes an aminobutanol phosphate phospho-lyase from the organism *Erwinia carotovora*.

The term "aminobutanol kinase" refers to a polypeptide (or polypeptides) having an enzyme activity that catalyzes the conversion of 3-amino-2-butanol to 3-amino-2-butanol O-phosphate. Amino butanol kinase may utilize ATP as the phosphate donor. Although there are no reports of enzymes catalyzing this reaction on 3-amino-2-butanol, there are reports of enzymes that catalyze the analogous reaction on the similar substrates ethanolamine and 1-amino-2-propanol (Jones, et al., supra). U.S. Patent Application Publication No. 2009/0155870 describes, in Example 14, an amino alcohol kinase of *Erwinia carotovora* subsp. *Atroseptica*.

The term "butanediol dehydrogenase" also known as "acetoin reductase" refers to a polypeptide (or polypeptides) having an enzyme activity that catalyzes the conversion of acetoin to 2,3-butanediol. Butanedial dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (GenBank Nos: BBA13085, D86412). (R)-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase," also known as "dial dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin (also known as coenzyme Bw or vitamin $B_{12}$; although vitamin B12 may refer also to other forms of cobalamin that are not coenzyme B12). Adenosyl cobalamin-dependent enzymes are known as EC 4.2.1.28 and are available, for example, from *Klebsiella oxytoca* (GenBank Nos: AA08099 (alpha subunit), D45071; BAA08100 (beta subunit), D45071; and BBA08101 (gamma subunit), D45071 (Note all three subunits are required for activity), and *Klebsiella pneumonia* (GenBank Nos: AAC98384 (alpha subunit), AF102064; GenBank Nos: AAC98385 (beta subunit), AF102064, GenBank Nos: AAC98386 (gamma subunit), AF102064). Other suitable dial dehydratases include, but are not limited to, B12-dependent dial dehydratases available from *Salmonella typhimurium* (GenBank Nos: AAB84102 (large subunit), AF026270; GenBank Nos: AAB84103 (medium subunit), AF026270; GenBank Nos: AAB84104 (small subunit), AF026270); and *Lactobacillus collinoides* (GenBank Nos: CAC82541 (large subunit), AJ297723; GenBank Nos: CAC82542 (medium subunit); AJ297723; GenBank Nos: CAD01091 (small subunit), AJ297723); and enzymes from *Lactobacillus brevis* (particularly strains CNRZ 734 and CNRZ 735, Speranza, et al., *J. Agric. Food Chem.* 45:3476-3480, 1997), and nucleotide sequences that encode the corresponding enzymes. Methods of diol dehydratase gene isolation are well known in the art (e.g., U.S. Pat. No. 5,686,276).

The term "pyruvate decarboxylase" refers to an enzyme that catalyzes the decarboxylation of pyruvic acid to acetaldehyde and carbon dioxide. Pyruvate dehydrogenases are known by the EC number 4.1.1.1. These enzymes are found in a number of yeast, including *Saccharomyces cerevisiae* (GenBank Nos: CAA97575, CAA97705, CAA97091).

It will be appreciated that host cells comprising an isobutanol biosynthetic pathway as provided herein may further comprise one or more additional modifications. U.S. Patent Application Publication No. 2009/0305363 (incorporated by reference) discloses increased conversion of pyruvate to acetolactate by engineering yeast for expression of a cytosol-localized acetolactate synthase and substantial elimination of pyruvate decarboxylase activity. In some embodiments, the host cells comprise modifications to reduce glycerol-3-phosphate dehydrogenase activity and/or disruption in at least one gene encoding a polypeptide having pyruvate decarboxylase activity or a disruption in at least one gene encoding a regulatory element controlling pyruvate decarboxylase gene expression as described in U.S. Patent Application Publication No. 2009/0305363 (incorporated herein by reference), modifications to a host cell that provide for increased carbon flux through an Entner-Doudoroff Pathway or reducing equivalents balance as described in U.S. Patent Application Publication No. 2010/0120105 (incorporated herein by reference). Other modifications include integration of at least one polynucleotide encoding a polypeptide that catalyzes a step in a pyruvate-utilizing biosynthetic pathway.

Other modifications include at least one deletion, mutation, and/or substitution in an endogenous polynucleotide encoding a polypeptide having acetolactate reductase activity. As used herein, "acetolactate reductase activity" refers to the activity of any polypeptide having the ability to catalyze the conversion of acetolactate to DHMB. Such polypeptides can be determined by methods well known in the art and disclosed herein. As used herein, "DHMB" refers to 2,3-dihydroxy-2-methyl butyrate. DHMB includes "fast DHMB," which has the 2S, 3S configuration, and "slow DHMB," which has the 2S, 3R configurate. See Kaneko et al., *Phytochemistry* 39: 115-120 (1995), which is herein incorporated by reference in its entirety and refers to fast DHMB as anglyceric acid and slow DHMB as tiglyceric acid. In embodiments, the polypeptide having acetolactate reductase activity is YMR226C of *Saccharomyces cerevisiae* or a homolog thereof.

Additional modifications include a deletion, mutation, and/or substitution in an endogenous polynucleotide encoding a polypeptide having aldehyde dehydrogenase and/or aldehyde oxidase activity. As used herein, "aldehyde dehydrogenase activity" refers to any polypeptide having a biological function of an aldehyde dehydrogenase. Such polypeptides include a polypeptide that catalyzes the oxidation (dehydrogenation) of aldehydes. Such polypeptides include a polypeptide that catalyzes the conversion of isobutyraldehyde to isobutyric acid. Such polypeptides also include a polypeptide that corresponds to Enzyme Commission Numbers EC 1.2.1.3, EC 1.2.1.4 or EC 1.2.1.5. Such polypeptides can be determined by methods well known in the art and disclosed herein. As used herein, "aldehyde oxidase activity" refers to any polypeptide having a biological function of an aldehyde oxidase. Such polypeptides include a polypeptide that catalyzes production of carboxylic acids from aldehydes. Such polypeptides include a polypeptide that catalyzes the conversion of isobutyraldehyde to isobutyric acid. Such polypeptides also include a polypeptide that corresponds to Enzyme Commission Number EC 1.2.3.1. Such polypeptides can be determined by methods well known in the art and disclosed herein. In some embodiments, the polypeptide having aldehyde dehydrogenase activity is ALD6 from *Saccharomyces cerevisiae* or a homolog thereof.

A genetic modification which has the effect of reducing glucose repression wherein the yeast production host cell is pdc- is described in U.S. Patent Application Publication No. 2011/0124060, incorporated herein by reference. In some embodiments, the pyruvate decarboxylase that is deleted or down-regulated is selected from the group consisting of: PDC1, PDC5, PDC6, and combinations thereof. In some embodiments, the pyruvate decarboxylase is selected from PDC1 pyruvate decarboxylase from *Saccharomyces cerevisiae*, PDC5 pyruvate decarboxylase from *Saccharomyces cerevisiae*, PDC6 pyruvate decarboxylase from *Saccharomyces cerevisiae*, pyruvate decarboxylase from *Candida glabrata*, PDC1 pyruvate decarboxylase from *Pichia stipites*, PDC2 pyruvate decarboxylase from *Pichia stipites*, pyruvate decarboxylase from *Kluveromyces lactis*, pyruvate decarboxylase from *Yarrowia lipolytica*, pyruvate decarboxylase from *Schizosaccharomyces pombe*, and pyruvate decarboxylase from *Zygosaccharomyces rouxii*. In some embodiments, host cells contain a deletion or down-regulation of a polynucleotide encoding a polypeptide that catalyzes the conversion of glyceraldehyde-3-phosphate to glycerate 1,3, bisphosphate. In some embodiments, the enzyme that catalyzes this reaction is glyceraldehyde-3-phosphate dehydrogenase.

In contrast, in an isobutanologen (PDC-) strain, PDC is deleted, the PDH pathway remains intact, and isobutanol production pathway enzymes are introduced. Often, the first enzyme to act in the isobutanol production pathway is acetolactate synthase (ALS). In isobutanologens, the carbon flux distribution for biomass growth and for the isobutanol pathway under aerobic conditions depends on the relative activity of ALS instead of the PDH enzyme. The physiological behavior of a recombinant isobutanologen is different from an unmodified *S. cerevisiae* due to the effect of the deletion of PDC genes and introduction of heterologous isobutanol pathway enzymes. To maximize biomass production in a recombinant isobutanologen in aerobic growth phase, the carbon flux has to channel through the PDH pathway efficiently to improve biomass yield and minimize carbon flux to isobutanol pathway leakages. Pathway leakage products can include isobutanol and isobutyric acid, which can adversely affect biomass growth rate and the final biomass achieved. In the production phase, the isobutanol yield and productivity can be adversely affected by accumulation of pathway intermediates (e.g., glycerol and isobutyric acid). Thus, the optimal operating regime (growth and production) for an ethanologen may not be the optimal operating regime for an isobutanologen.

WIPO publication number WO 2001/103300 discloses recombinant host cells comprising (a) at least one heterologous polynucleotide encoding a polypeptide having dihydroxy-acid dehydratase activity; and (b)(i) at least one deletion, mutation, and/or substitution in an endogenous gene encoding a polypeptide affecting Fe—S cluster biosynthesis; and/or (ii) at least one heterologous polynucleotide encoding a polypeptide affecting Fe—S cluster biosynthesis. In embodiments, the polypeptide affecting Fe—S cluster biosynthesis is encoded by AFT1, AFT2, FRA2, GRX3, or CCC1. In embodiments, the polypeptide affecting Fe—S cluster biosynthesis is constitutive mutant AFT1 L99A, AFT1 L102A, AFT1 C291F, or AFT1 C293F.

Additionally, host cells may comprise heterologous polynucleotides encoding a polypeptide with phosphoketolase activity and/or a heterologous polynucleotide encoding a polypeptide with phosphotransacetylase activity.

In some embodiments, any particular nucleic acid molecule or polypeptide may be at least 80%, 85%, 90%, 95%, 96%, 97%, 98%, or 99% identical to a nucleotide sequence or polypeptide sequence described herein. The term "percent identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) Computational Molecular Biology (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Standard recombinant DNA and molecular cloning techniques are well known in the art and are described by Sambrook, et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis) and by Ausubel, et al. (Ausubel, et al., *Current Protocols in Molecular Biology*, pub. by Greene Publishing Assoc. and Wiley-Interscience, 1987). Examples of methods to construct microorganisms that comprise a butanol biosynthetic pathway are disclosed, for example, in U.S. Pat. No. 7,851,188, and U.S. Patent Application Publication Nos. 2007/0092957; 2007/0259410; 2007/0292927; 2008/0182308; 2008/0274525; 2009/0155870; 2009/0305363; and 2009/0305370, the entire contents of each are herein incorporated by reference.

Growth for Production

Recombinant host cells disclosed herein are contacted with suitable carbon substrates, typically in fermentation media. Additional carbon substrates may include, but are not limited to, monosaccharides such as fructose, oligosaccharides such as lactose, maltose, galactose, or sucrose, polysaccharides such as starch or cellulose or mixtures thereof and unpurified mixtures from renewable feedstocks such as cheese whey permeate, cornsteep liquor, sugar beet molasses, and barley malt. Other carbon substrates can include ethanol, lactate, succinate, or glycerol.

Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth Cl Compd.*, [Int. Symp.], $7^{th}$ (1993), 415-32, Editors: Murrell, J. Collin, Kelly, Don P.; Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in U.S. Patent Application Publication No. 2007/0031918 A1, which is herein incorporated by reference. Biomass, when used in reference to carbon substrate, refers to any cellulosic or lignocellulosic material and includes materials comprising cellulose, and optionally further comprising hemicellulose, lignin, starch, oligosaccharides and/or monosaccharides. Biomass can also comprise additional components, such as protein and/or lipid. Biomass can be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of an enzymatic pathway described herein.

Culture Conditions

Typically cells are grown at a temperature in the range of about 20° C. to about 40° C. in an appropriate medium. Suitable growth media in the present invention are common commercially prepared media such as Luria Bertani (LB) broth, Sabouraud Dextrose (SD) broth or Yeast Medium (YM) broth or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media can also be used, and the appropriate medium for growth of the particular microorganism will be known by one skilled in the art of microbiology or fermentation science. The use of agents known to modulate catabolite repression directly or indirectly, e.g., cyclic adenosine 2',3'-monophosphate (cAMP), can also be incorporated into the fermentation medium.

Suitable pH ranges for the fermentation are between pH 5.0 to pH 9.0, where pH 6.0 to pH 8.0 is preferred for the initial condition. Suitable pH ranges for the fermentation of yeast are typically between about pH 3.0 to about pH 9.0. In one embodiment, about pH 5.0 to about pH 8.0 is used for the initial condition. Suitable pH ranges for the fermentation of other microorganisms are between about pH 3.0 to about pH 7.5. In one embodiment, about pH 4.5 to about pH 6.5 is used for the initial condition.

Fermentations can be performed under aerobic or anaerobic conditions. In one embodiment, anaerobic or microaerobic conditions are used for fermentation.

Industrial Batch and Continuous Fermentations

Butanol, or other products, can be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples can be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Butanol, or other products, may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol, or other products, can be practiced using batch, fed-batch or continuous processes and that any known mode of fermentation would be suitable. Additionally, it is contemplated that cells can be immobilized on a substrate as whole cell catalysts and subjected to fermentation conditions for butanol production.

Methods for Recovering Butanol using Extractive Fermentation

Bioproduced butanol may be recovered from a fermentation medium containing butanol, water, at least one fermentable carbon source, and a microorganism that has been genetically modified (that is, genetically engineered) to produce butanol via a biosynthetic pathway from at least one carbon source. The first step in the process is contacting the fermentation medium with a water immiscible organic extractant composition comprising a solvent, as described above, to form a two-phase mixture comprising an aqueous phase and a butanol-containing organic phase. "Contacting" means the fermentation medium and the organic extractant composition or its solvent component(s) are brought into physical contact at any time during the fermentation process. In one embodiment, the fermentation medium further comprises ethanol, and the butanol-containing organic phase can contain ethanol.

In certain embodiments where more than one solvent is used for the extraction, the contacting may be performed with the solvents of the extractant composition having been previously combined. For example, the first and second solvents may be combined in a vessel such as a mixing tank to form the extractant, which is then added to a vessel containing the fermentation medium. Alternatively, the contacting may be performed with the first and second solvents becoming combined during the contacting. For example, the first and second solvents may be added separately to a vessel which contains the fermentation medium. In one embodiment, contacting the fermentation medium with the organic extractant composition further comprises contacting the fermentation medium with the first solvent prior to contacting the fermentation medium and the first solvent with the second solvent. In one embodiment, the contacting with the second solvent occurs in the same vessel as the contacting with the first solvent. In one embodiment, the contacting with the second solvent occurs in a different vessel from the contacting with the first solvent. For example, the first solvent may be contacted with the fermentation medium in one vessel, and the contents transferred to another vessel in which contacting with the second solvent occurs.

The organic extractant composition may contact the fermentation medium at the start of the fermentation forming a biphasic fermentation medium. Alternatively, the organic extractant composition may contact the fermentation medium after the microorganism has achieved a desired amount of growth, which can be determined by measuring the optical density of the culture.

Further, the organic extractant composition may contact the fermentation medium at a time at which the butanol level in the fermentation medium reaches a preselected level, for example, before the butanol concentration reaches a toxic level. The butanol concentration may be monitored during the fermentation using methods known in the art, such as by gas chromatography or high performance liquid chromatography.

Fermentation may be run under aerobic conditions for a time sufficient for the culture to achieve a preselected level of growth, as determined by optical density measurement. An inducer may then be added to induce the expression of the butanol biosynthetic pathway in the modified microorganism, and fermentation conditions are switched to microaerobic or anaerobic conditions to stimulate butanol production, as described in detail in Example 6 of US Patent Application Publication No. 2009/0305370 A1. The extractant is added after the switch to microaerobic or anaerobic conditions.

Through contacting the fermentation medium with the organic extractant, the butanol product partitions into the organic extractant, decreasing the concentration in the aqueous phase containing the microorganism, thereby limiting the exposure of the production microorganism to the inhibitory butanol product. The volume of the organic extractant to be used depends on a number of factors, including the volume of the fermentation medium, the size of the fermentor, the partition coefficient of the extractant for the butanol product, and the fermentation mode chosen, as described below. The volume of the organic extractant may be about 3% to about 60% of the fermentor working volume. The ratio of the extractant to the fermentation medium is from about 1:20 to about 20:1 on a volume:volume basis, for example from about 1:15 to about 15:1, or from about 1:12 to about 12:1, or from about 1:10 to about 10:1, or from about 1:9 to about 9:1, or from about 1:8 to about 8:1.

The next step is separating the butanol-containing organic phase from the aqueous phase using methods known in the art, including but not limited to, siphoning, decantation, centrifugation, using a gravity settler, membrane-assisted phase splitting, and the like. Recovery of the butanol from the butanol-containing organic phase can be done using methods known in the art, including but not limited to, distillation, adsorption by resins, separation by molecular sieves, pervaporation, and the like. Specifically, distillation may be used to recover the butanol from the butanol-containing organic phase. The extractant or the solvents may be recycled to the butanol production and/or recovery process.

Gas stripping may be used concurrently with the solvents of the organic extractant composition to remove the butanol product from the fermentation medium. Gas stripping may be done by passing a gas such as air, nitrogen, or carbon dioxide through the fermentation medium, thereby forming a butanol-containing gas phase. The butanol product may be recovered from the butanol-containing gas phase using methods known in the art, such as using a chilled water trap to condense the butanol, or scrubbing the gas phase with a solvent.

Any butanol remaining in the fermentation medium after the fermentation run is completed may be recovered by continued extraction using fresh or recycled organic extractant. Alternatively, the butanol can be recovered from the fermentation medium using methods known in the art, including, but not limited to distillation, azeotropic distillation, liquid-liquid extraction, adsorption, gas stripping, membrane evaporation, pervaporation, and the like.

The two-phase extractive fermentation method may be carried out in a continuous mode in a stirred tank fermentor. In this mode, the mixture of the fermentation medium and the butanol-containing organic extractant composition is removed from the fermentor. The two phases are separated by means known in the art including, but not limited to, siphoning, decantation, centrifugation, using a gravity settler, membrane-assisted phase splitting, and the like, as described above. After separation, the fermentation medium may be recycled to the fermentor or may be replaced with fresh medium. Then, the extractant is treated to recover the butanol product as described above. The extractant may then be recycled back into the fermentor for further extraction of the product. Alternatively, fresh extractant may be continuously added to the fermentor to replace the removed extractant. This continuous mode of operation offers several advantages. Because the product is continually removed from the reactor, a smaller volume of organic extractant composition is required enabling a larger volume of the fermentation medium to be used. This results in higher production yields. The volume of the organic extractant composition may be about 3% to about 50% of the fermentor working volume; 3% to about 20% of the fermentor working volume; or 3% to about 10% of the fermentor working volume. It is beneficial to use the smallest amount of extractant in the fermentor as possible to maximize the volume of the aqueous phase, and therefore, the amount of cells in the fermentor. The process may be operated in an entirely continuous mode in which the extractant is continuously recycled between the fermentor and a separation apparatus and the fermentation medium is continuously removed from the fermentor and replenished with fresh medium. In this entirely continuous mode, the butanol product is not allowed to reach the critical toxic concentration and fresh nutrients are continuously provided so that the fermentation may be carried out for long periods of time. The apparatus that may be used to carryout these modes of two-phase extractive fermentations are well known in the art. Examples are described, for example, by Kollerup et al. in U.S. Pat. No. 4,865,973.

Batchwise fermentation mode may also be used. Batch fermentation, which is well known in the art, is a closed system in which the composition of the fermentation medium is set at the beginning of the fermentation and is not subjected to artificial alterations during the process. In this mode, a volume of organic extractant composition is added to the fermentor and the extractant is not removed during the process. The organic extractant composition may be formed in the fermentor by separate addition of the first and the second solvents, or the solvents may be combined to form the extractant composition prior to the addition of the extractant composition to the fermentor. Although this mode is simpler than the continuous or the entirely continuous modes described above, it requires a larger volume of organic extractant composition to minimize the concentration of the inhibitory butanol product in the fermentation medium. Consequently, the volume of the fermentation medium is less and the amount of product produced is less than that obtained using the continuous mode. The volume of the organic extractant composition in the batchwise mode may be 20% to about 60% of the fermentor working volume; or 30% to about 60% of the fermentor working volume. It is beneficial to use the smallest volume of extractant in the fermentor as possible, for the reason described above.

Fed-batch fermentation mode may also be used. Fed-batch fermentation is a variation of the standard batch system, in which the nutrients, for example glucose, are added in increments during the fermentation. The amount and the rate of addition of the nutrient may be determined by routine experimentation. For example, the concentration of critical nutrients in the fermentation medium may be monitored during the fermentation. Alternatively, more easily measured factors such as pH, dissolved oxygen, and the partial pressure of waste gases, such as carbon dioxide, may be monitored. From these measured parameters, the rate of nutrient addition may be determined. The amount of organic extractant composition used and its methods of addition in this mode is the same as that used in the batchwise mode, described above.

Extraction of the product may be done downstream of the fermentor, rather than in situ. In this external mode, the extraction of the butanol product into the organic extractant composition is carried out on the fermentation medium removed from the fermentor. The amount of organic solvent used is about 20% to about 60% of the fermentor working volume; or 30% to about 60% of the fermentor working volume. The fermentation medium may be removed from the fermentor continuously or periodically, and the extraction of the butanol product by the organic extractant composition may be done with or without the removal of the cells from the fermentation medium. The cells may be removed from the fermentation medium by means known in the art including, but not limited to, filtration or centrifugation. After separation of the fermentation medium from the extractant by means described above, the fermentation medium may be recycled into the fermentor, discarded, or treated for the removal of any remaining butanol product. Similarly, the isolated cells may also be recycled into the fermentor. After treatment to recover the butanol product, the extractant, the first solvent, and/or the second solvent may be recycled for use in the extraction process. Alternatively, fresh extractant may be used. In this mode the extractant is not present in the fermentor, so the toxicity of the extractant is much less of a problem. If the cells are separated from the fermentation medium before contacting with the extractant, the problem of extractant toxicity is further reduced. Furthermore, using this external mode there is less chance of forming an emulsion and evaporation of the extractant is minimized, alleviating environmental concerns. Methods for Production of Butanol using Extractive Fermentation with an Extractant Comprising a Dry Solvent An improved method for the production of butanol is provided, wherein a microorganism that has been genetically modified to produce butanol via a biosynthetic pathway from at least one carbon source, is grown in a biphasic fermentation medium. The biphasic fermentation medium comprises an aqueous phase and a water immiscible organic extractant composition comprising a dry solvent.

Isobutanol may be produced by extractive fermentation with the use of a modified *Escherichia coli* strain in combination with an oleyl alcohol as the organic extractant, as disclosed in US Patent Application Publication No. 2009/0305370 A1. The method yields a higher effective titer for isobutanol (i.e., 37 g/L) compared to using conventional fermentation techniques (see Example 6 of US Patent Application Publication No. 2009/0305370 A1). For example, Atsumi et al. (*Nature* 451(3):86-90, 2008) report isobutanol titers up to 22 g/L using fermentation with an *Escherichia coli* that was genetically modified to contain an isobutanol biosynthetic pathway. The higher butanol titer obtained with the extractive fermentation method disclosed in U.S. Patent Application Publication No. 2009/0305370 A1 results, in part, from the removal of the toxic butanol product from the fermentation medium, thereby keeping the level below that which is toxic to the microorganism. It is reasonable to assume that the present extractive fermentation method employing a water-immiscible organic extractant composition comprising a dry solvent as defined herein would be used in a similar way and provide similar results.

Butanol produced by the method disclosed herein may have an effective titer of greater than 22 g per liter of the fermentation medium. Alternatively, the butanol produced by methods disclosed may have an effective titer of at least 25 g per liter of the fermentation medium. Alternatively, the butanol produced by methods described herein may have an effective titer of at least 30 g per liter of the fermentation medium. Alternatively, the butanol produced by methods described herein may have an effective titer of at least 37 g per liter of the fermentation medium. Alternatively, the butanol produced by methods described herein may have an effective titer of at least 45 g per liter of the fermentation medium. Alternatively, the butanol produced by methods described herein may have an effective titer of at least 50 g per liter of the fermentation medium. Alternatively, the butanol produced by methods described herein may have an effective titer of at least 60 g per liter of the fermentation medium. In some embodiments, the recovered butanol has an effective titer from about 22 g per liter to about 50 g per liter, about 22 g per liter to 40 g per liter, about 22 g per liter to about 30 g per liter, about 25 g per liter to about 50 g per liter, about 25 g per liter to 40 g per liter, about 25 g per liter to about 30 g per liter, about 30 g per liter to about 50 g per liter, about 40 g per liter to about 50 g per liter, about 22 g per liter to about 60 g per liter, about 30 g per liter to about 60 g per liter, about 40 g per liter to about 60 g per liter, about 22 g per liter to about 80 g per liter, about 40 g per liter to about 80 g per liter, about 50 g per liter to about 80 g per liter, about 65 g per liter to about 80 g per liter. The present methods are generally described below with reference to a FIGS. 1 through 7.

Figure 1:
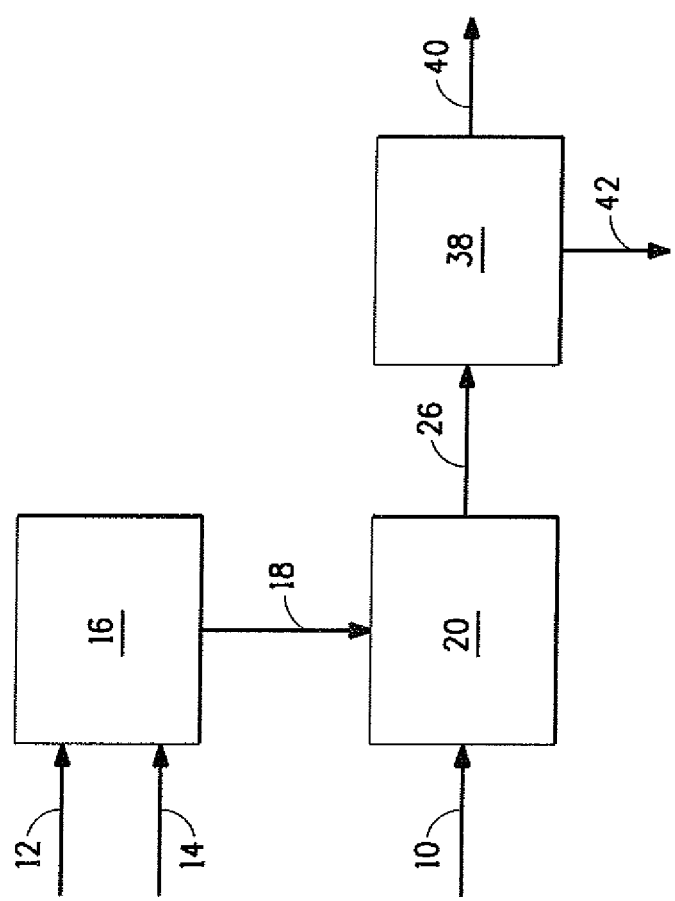

Referring now to FIG. 1, there is shown a schematic representation of one embodiment of processes for producing and recovering butanol using in situ extractive fermentation. An aqueous stream 10 of at least one fermentable carbon source is introduced into a fermentor 20, which contains at least one recombinant microorganism (not shown) capable of converting the at least one fermentable carbon source into butanol. A stream of a first dry solvent 12 and a stream of an optional second solvent 14 are introduced to a vessel 16, in which the solvents are combined to form the extractant 18. A stream of the extractant 18 is introduced into the fermentor 20, in which contacting of the fermentation medium with the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Figure 2:
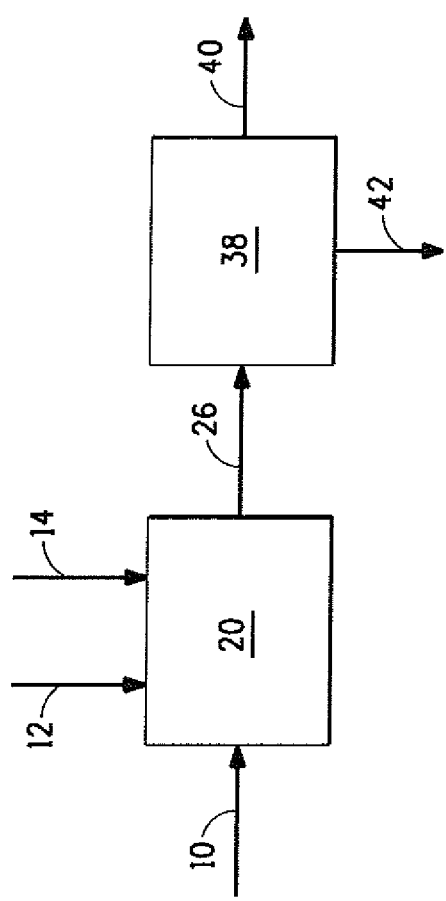

Referring now to FIG. 2, there is shown a schematic representation of one embodiment of processes for producing and recovering butanol using in situ extractive fermentation. An aqueous stream 10 of at least one fermentable carbon source is introduced into a fermentor 20, which contains at least one recombinant microorganism (not shown) capable of converting the at least one fermentable carbon source into butanol. A stream of the first dry solvent 12 and a stream of the optional second solvent 14 of which the extractant is comprised are introduced separately to the fermentor 20, in which contacting of the fermentation medium with the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Figure 3:
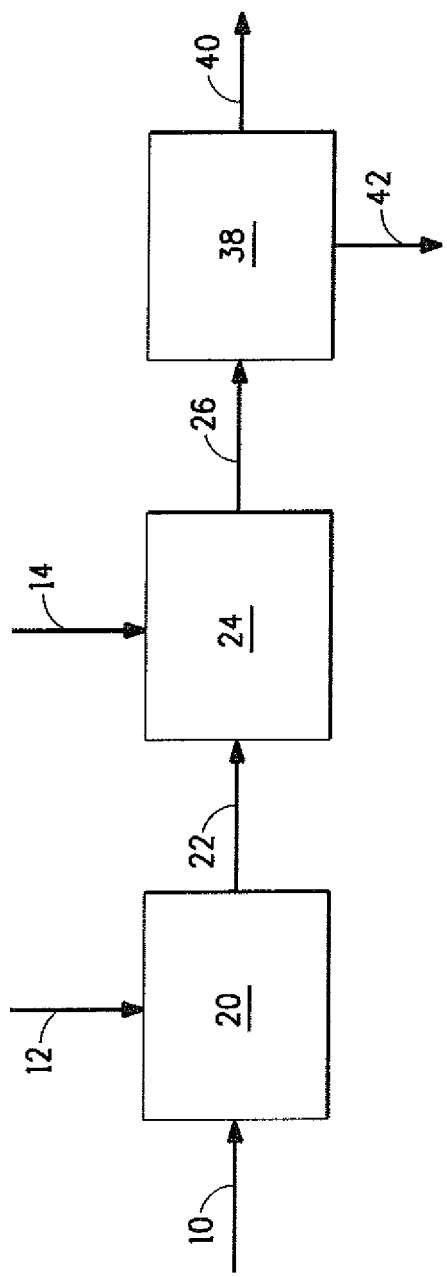

Referring now to FIG. 3, there is shown a schematic representation of one embodiment of processes for producing and recovering butanol using in situ extractive fermentation. An aqueous stream 10 of at least one fermentable carbon source is introduced into a first fermentor 20, which contains at least one recombinant microorganism (not shown) capable of converting the at least one fermentable carbon source into butanol. A stream of the first dry solvent 12 of which the extractant is comprised is introduced to the fermentor 20, and a stream 22 comprising a mixture of the first dry solvent and the contents of fermentor 20 is introduced into a second fermentor 24. A stream of the optional second solvent 14 of which the extractant is comprised is introduced into the second fermentor 24, in which contacting of the fermentation medium with the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Figure 4:
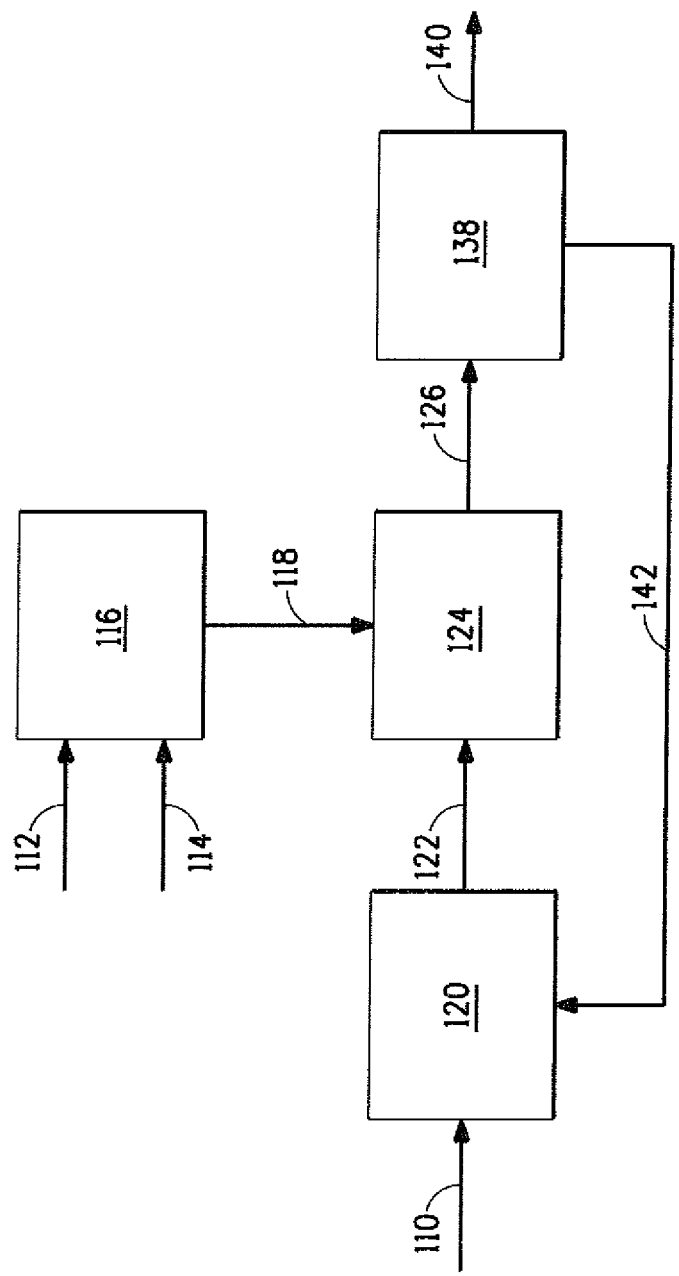

Referring now to FIG. 4, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one recombinant microorganism (not shown) capable of converting the at least one fermentable carbon source into butanol. A stream of the first dry solvent 112 and a stream of the optional second solvent 114 are introduced to a vessel 116, in which the solvents are combined to form the extractant 118. At least a portion, shown as stream 122, of the fermentation medium in fermentor 120 is introduced into vessel 124. A stream of the extractant 118 is also introduced into vessel 124, in which contacting of the fermentation medium with the extractant to form a two-phase mixture comprising an aqueous phase and a butanol-containing organic phase occurs. A stream 126 comprising both the aqueous and organic phases is introduced into a vessel 138, in which separation of the aqueous and organic phases is performed to produce a butanol-containing organic phase 140 and an aqueous phase 142 which may be returned to the fermentor 120.

Figure 5:
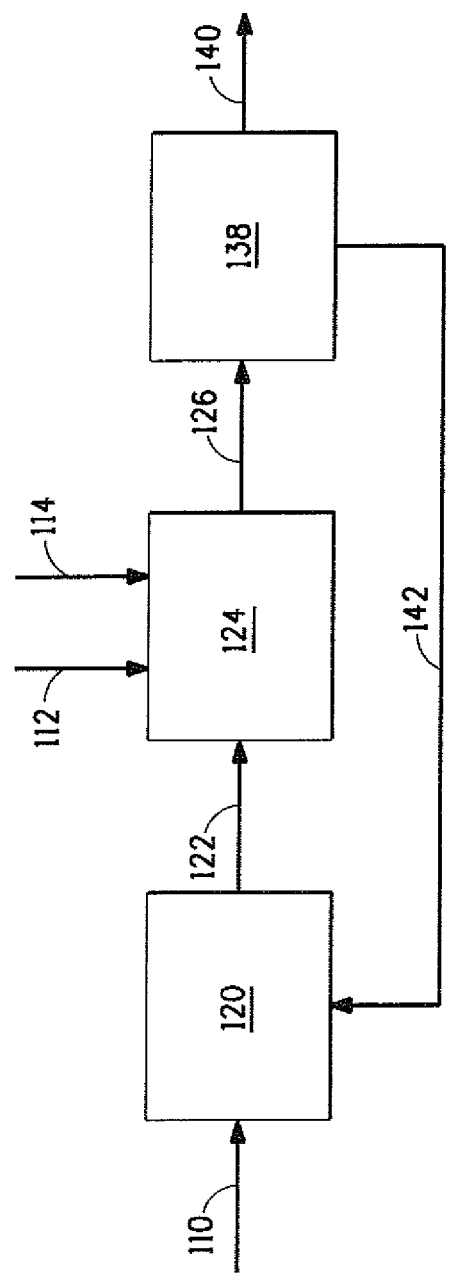

Referring now to FIG. 5, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one recombinant microorganism (not shown) capable of converting the at least one fermentable carbon source into butanol. A stream of the first dry solvent 112 and a stream of the optional second solvent 114 of which the extractant is comprised are introduced separately to a vessel 124, in which the solvents are combined to form the extractant. At least a portion, shown as stream 122, of the fermentation medium in fermentor 120 is also introduced into vessel 124, in which contacting of the fermentation medium with the extractant to form a two-phase mixture comprising an aqueous phase and a butanol-containing organic phase occurs. A stream 126 comprising both the aqueous and organic phases is introduced into a vessel 138, in which separation of the aqueous and organic phases is performed to produce a butanol-containing organic phase 140 and an aqueous phase 142 which may be returned to the fermentor 120.

Figure 6:
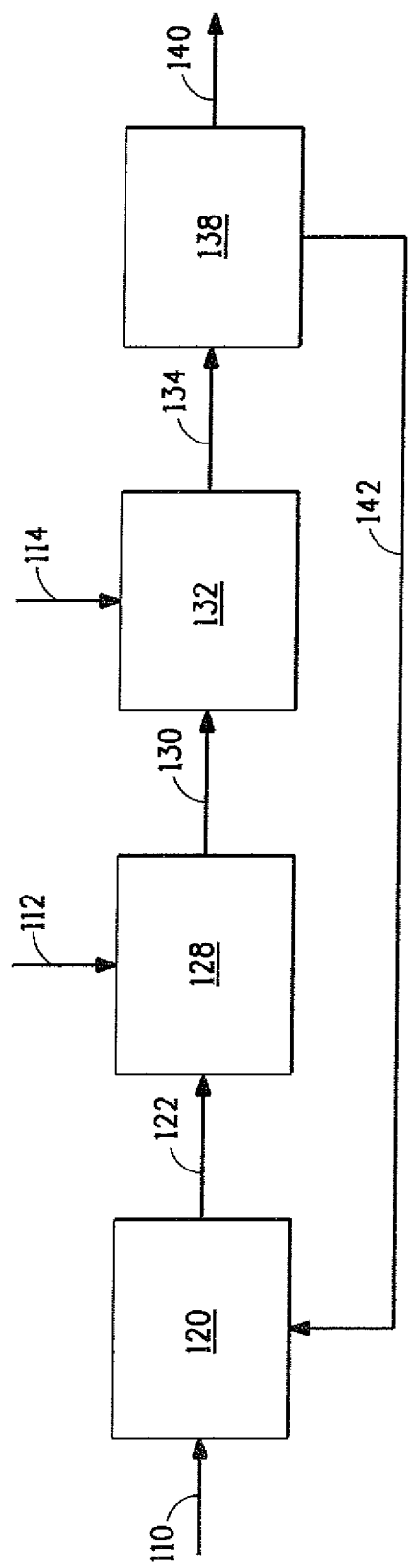

Referring now to FIG. 6, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one recombinant microorganism (not shown) capable of converting the at least one fermentable carbon source into butanol. A stream of the first dry solvent 112 of which the extractant is comprised is introduced to a vessel 128, and at least a portion, shown as stream 122, of the fermentation medium in fermentor 120 is also introduced into vessel 128. A stream 130 comprising a mixture of the first dry solvent and the contents of fermentor 120 is introduced into a second vessel 132. A stream of the optional second solvent 114 of which the extractant is comprised is introduced into the second vessel 132, in which contacting of the fermentation medium with the extractant to form a two-phase mixture comprising an aqueous phase and a butanol-containing organic phase occurs. A stream 134 comprising both the aqueous and organic phases is introduced into a vessel 138, in which separation of the aqueous and organic phases is performed to produce a butanol-containing organic phase 140 and an aqueous phase 142 which may be returned to the fermentor 120.

The extractive processes described herein can be run as batch processes or can be run in a continuous mode where fresh extractant is added and used extractant is pumped out such that the amount of extractant in the fermentor remains constant during the entire fermentation process. Such continuous extraction of products and byproducts from the fermentation can increase effective rate, titer and yield.

In yet another embodiment, it is also possible to operate the liquid-liquid extraction in a flexible co-current or, alternatively, counter-current way that accounts for the difference in batch operating profiles when a series of batch fermentors are used. In this scenario the fermentors are filled with fermentable mash which provides at least one fermentable carbon source and recombinant microorganism in a continuous fashion one after another for as long as the plant is operating. Referring to FIG. 7, once Fermentor F100 fills with mash and microorganism, the mash and microorganism feed may advance to Fermentor F101 and then to Fermentor F102 and then back to Fermentor F100 in a continuous loop. The fermentation in any one fermentor begins once mash and microorganism are present together and continues until the fermentation is complete. The mash and microorganism fill time may equal the number of fermentors divided by the total cycle time (fill, ferment, empty and clean). If the total cycle time is 60 hours and there are 3 fermentors then the fill time may be 20 hours. If the total cycle time is 60 hours and there are 4 fermentors then the fill time may be 15 hours.

Adaptive co-current extraction follows the fermentation profile assuming the fermentor operating at the higher broth phase titer can utilize the extracting solvent stream richest in butanol concentration and the fermentor operating at the lowest broth phase titer will benefit from the extracting solvent stream leanest in butanol concentration. For example, referring again to FIG. 7, consider the case where Fermentor F100 is at the start of a fermentation and operating at relatively low butanol broth phase (B) titer, Fermentor F101 is in the middle of a fermentation operating at relatively moderate butanol broth phase titer and Fermentor F102 is near the end of a fermentation operating at relatively high butanol broth phase titer. In this case, lean extracting solvent (S), with minimal or no extracted butanol, can be fed to Fermentor F100, the "solvent out" stream (S') from Fermentor F100 having an extracted butanol component can then be fed to Fermentor F101 as its "solvent in" stream and the solvent out stream from F101 can then be fed to Fermentor F102 as its solvent in stream. The solvent out stream from F102 can then be sent to be processed to recover the butanol present in the stream. The processed solvent stream from which most of the butanol is removed can be returned to the system as lean extracting solvent and would be the solvent in feed to Fermentor F100 above.

As the fermentations proceed in an orderly fashion the valves in the extracting solvent manifold can be repositioned to feed the leanest extracting solvent to the fermentor operating at the lowest butanol broth phase titer. For example, assume (a) Fermentor F102 completes its fermentation and has been reloaded and fermentation begins anew, (b) Fermentor F100 is in the middle of its fermentation operating at moderate butanol broth phase titer and (c) Fermentor F101 is near the end of its fermentation operating at relatively higher butanol broth phase titer. In this scenario the leanest extracting solvent would feed F102, the extracting solvent leaving F102 would feed Fermentor F100 and the extracting solvent leaving Fermentor F100 would feed Fermentor F101.

An advantage of operating this way can be to maintain the broth phase butanol titer as low as possible for as long as possible to realize improvements in productivity. Additionally, it can be possible to drop the temperature in the other fermentors that have progressed further into fermentation that are operating at higher butanol broth phase titers. The drop in temperature can allow for improved tolerance to the higher butanol broth phase titers.

Having described a variety of techniques, approaches, systems and so forth that can implement dry solvents, including multiple solvents, multiple solvent extraction techniques are now be described in additional detail. It should be apparent that the techniques, approaches, compositions, and so on described in conjunction with a solvent mixture, can implement the principles previously described and vice versa. Additionally, while multiple solvent systems including dry solvents are described, it is to be apparent that comparatively "wet" solvent systems can benefit from the principles of this disclosure.

Extraaction of Butanol using a Solvent Mixture

In embodiments, a solvent mixture is used to extract alcohol from an aqueous solution. For example, a solvent mixture and fermentation broth are contacted together to extract butanol, such as isobutanol from the broth. The contacting can be performed internally (internal to a fermentor) externally (e.g., via a cooling loop), or a combination thereof, and so forth as described above. As also is described above, a fermentation broth can include, but is not limited to, fermentation products, fermentation solids, unfermented carbon substrate (e.g., sugar), microorganisms (alive, dead, intended, unintended), nutrients (e.g., mineral nutrients use by a microorganism to produce alcohol), and so forth.

In examples, the solvent mixture includes a first solvent and a second solvent. Optionally, additional solvents (three or more), additives, and so forth to promote efficient extraction can be included in the solvent mixture as contemplated by one of ordinary skill in the art.

The individual solvents can be selected so the resulting mixture exhibits properties that increase extraction efficiency, improve extraction selectivity (e.g., preferentially extracting, for example, a target alcohol (isobutanol) in comparison to other compound such as water), or is an anti-solvent for nutrients. Additional examples include, but are not limited to, minimizes moisture content (tendency of the solvent to dissolve water, or wetness), exhibits good hydrophobicity, the ability to be separated from the target alcohol by distillation, it is a good solvent for inhibitory impurities or co-products, the solvents are economically viable, environmental considerations, and the like. In embodiments, hydrophobicity is expressed as log P, which is the log of the partition coefficient of the solvent or solvent mixture in a mix of solvent/octanol/water. Thus, log P can be expressed as the base ten logarithm of the ratio of the total molar concentration of the solvent(s) in the organic phase divided by the total molar concentration of the solvent(s) in the aqueous phase in the presence of octanol, e.g., the sum of all solvents.

Other relevant solvent mixture properties that can be tailored include, but are not limited to, low toxicity/biocompatibility to a microorganism that is capable of producing the alcohol, low tendency to extract nutrients (e.g., nutrients used by a microorganism to produce alcohol), boiling point, compatibility with other solvents to be included in the solvent mixture, thermal stability, low volatility, and so on. Example nutrients include minerals, and vitamins. A solvent's affinity to amino acids, proteins, peptides, and peptones also can be considered. In some embodiments, one or more of the solvents or the solvent mixture is used to transport nutrients to a fermentation broth. In examples such as this, the solvent mixture can contact nutrients prior to contacting the broth. Accordingly, the nutrients can be exchanged with the broth so the nutrients enter the broth and the alcohol enters the solvent mixture. Other relevant properties include a solvent's affinity to impurities that inhibit the microorganism. For example, a solvent mixture includes a solvent that has a high affinity to a compound that is produced during fermentation, but is toxic to a microorganism generating the product alcohol. The ability to separate the solvents one from another may be considered, if for example, a solvent is provided as an offtake after use. COFA can be purified to separate any co-solvents and provided as an off-take product.

A solvent can be selected because it is effective for removing a contaminate (e.g., butyric acid) that is toxic to the microorganism. While maximizing beneficial properties is preferred, trade-offs can be made to avoid or minimize non-preferred properties. For example, while some solvents have high butanol affinity (Kd) they can exhibit high moisture content (wetness), and/or are toxic to a microorganism. Other solvents are considered to be dry (low moisture), have good biocompatibility (high log P), but exhibit low or poor Kd.

In some implementations, the solvent mixture exhibits one or more properties that are not indicated by a linear molar combination of the first and second solvents. Some solvent mixtures, for example, exhibit properties that are not indicated based on the properties of the individual solvents and the mole factions of the individual solvents. For example, it may be expected that a fifty/fifty (50/50) ratio of a first and second solvent for a particular characteristic (e.g., hydrophobicity) would behave as if the solvent mixture's corresponding property or characteristic was fifty percent (50%) that of the first solvent and fifty percent (50%) that of the second solvent. In some instances, the solvent mixture exhibits a property that is influenced to a comparatively greater degree by one of the solvents in the mixture than the other solvent. The foregoing is also applicable to solvent mixtures including more than two solvents. In some instances, this departure from that indicated by a linear combination is due to intermolecular interactions between the solvents in the solvent mixture. Examples include, but are not limited to, polarity, existence of hydrogen bonding, van der Waals forces, e.g., London forces, and the like. This departure from predicted behavior can be graphically represented (generally and in a simplified fashion) by the diagram shown in FIG. 15.

As can be seen in FIG. 15, with respect to solvent properties, a binary solvent mixture can depart from that which is indicated by a linear combination of the first and second solvent. As illustrated, the property may depart from that which is expected (e.g., the "Linear combination") from the individual solvents based on their respective mole fractions as generally illustrated above. The property or characteristic can be beneficial (e.g., good selectivity in a butanol extraction, high affinity for butanol) or it may exhibit a negative property (e.g., exhibit poor hydrophobicity). Thus, a solvent mixture can depart from that indicated by the linear combination (generally) along the two curved lines. For example, mixing a first solvent that is dry (low moisture) and biocompatible (high log P) with a microorganism (butanologen) with a second wet solvent that has a high Kd can result in a solvent mixture that is efficient at extracting butanol from fermentation broth and exhibits good biocompatibility with butanalogens in the broth. In this way, a solvent mixture can be tailored to exhibit a synergistic effect, a favorable effect that is not indicated by a linear combination of the first and second solvents. For example, a solvent mixture of isohexadecane and isododecanol can exhibit good hydrophobicity and may be generally non-toxic (e.g., biocompatible) with a butanologen in comparison to a solvent mixture of thymol and COFA.

The properties of a solvent mixture are sometimes described by a complex function of the component mole fractions. For example, the natural logarithm of the activity coefficient of a component in a non-ideal liquid mixture can be expressed by an empirical model of solution behavior such as that provided by the Margules equation. In this instance, the natural logarithm of the activity coefficient of any one of the components is a third order polynomial function of the mole fractions of all of the components in the solvent mixture.

When distributing isobutanol, for example, between two contacting immiscible non-ideal liquid mixtures (e.g., an aqueous phase and an organic phase), an equilibrium molar partition coefficient can be equated to a ratio of the activity coefficient of isobutanol in one mixture (e.g., aqueous phase) to the activity coefficient of isobutanol in the other mixture (e.g., organic phase). The natural logarithm of the molar partition coefficient can therefore be equated to the difference between the natural logarithm of the two activity coefficients which will follow a third order polynomial function. One skilled in the art can expect that properties such as Kd and log P of a mixture can follow similarly if not more complex functions of the component mole fractions. Describing the equilibrium moisture content of a non-ideal liquid mixture as a function of the component mole fractions can be even more complex.

While the solvent mixture or portions thereof can be immiscible in water, e.g., on the order of $10^{-7}$, in some instances one or more of the solvents can be comparatively weakly miscible in water. It is also to be appreciated, that water can be miscible (e.g., somewhat miscible) in the solvent mixture and/or miscible in one or more solvents included in the solvent mixture. COFA in some examples can absorb moisture, or water, such that the COFA is "wet". A solvent's tendency to absorb moisture, e.g., act as a solvent, in some examples, can differ from that solvent's ability to solvate in water, e.g., its hydrophobicity. A table of various solvents and their respective characteristics is reproduced directly below.

TABLE 1

Example solvent properties

| Solvent | LogP | Kd | Moisture Content (wt %) |
|---|---|---|---|
| Corn oil | 19 | 0.25 | 0.70 |
| FABE | 9.4 | 1.4 | 0.18 |
| COFA | 6.5 | 3 | 0.70 |
| 2-ethylhexanol | 2.8 | 7.8 | 2 |
| Carvacrol | 3.3 | 15.6 | 2 |
| Tetrabutylurea | 6.6 | 7.4 | 0.9 |
| Isododecanol | 4.4 | 5.4 | 0.2 |
| Tributylphosphate | 4.3 | 9.8 | 6.7 |
| Isododecane | 6.2 | 0.25 | <0.01 |
| Isohexadecane | 8.0 | 0.2 | <0.01 |
| Triisopropylbenzene | 6.2 | 0.65 | <0.01 |

Confirmation of Isobutanol Production

The presence and/or concentration of isobutanol in the culture medium can be determined by a number of methods known in the art (see, for example, U.S. Pat. No. 7,851,188, incorporated by reference). For example, a specific high performance liquid chromatography (HPLC) method utilizes a Shodex SH-1011 column with a Shodex SHG guard column, both may be purchased from Waters Corporation (Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol has a retention time of 46.6 min under the conditions used.

Alternatively, gas chromatography (GC) methods are available. For example, a specific GC method utilizes an HP-INNOWax column (30 m×0.53 mm id, 1 μm film thickness, Agilent Technologies, Wilmington, Del.), with a flame ionization detector (FID). The carrier gas is helium at a flow rate of 4.5 mL/min, measured at 150° C. with constant head pressure; injector split is 1:25 at 200° C.; oven temperature is 45° C. for 1 min, 45 to 220° C. at 10° C./min, and 220° C. for 5 min; and FID detection is employed at 240° C. with 26 mL/min helium makeup gas. The retention time of isobutanol is 4.5 min.

While various embodiments of the present invention have been described herein, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of those skilled in the art to which this invention pertains, and are herein incorporated by reference to the same extent as if each individual publication, patent, or patent application was specifically and individually indicated to be incorporated by reference.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Some of the examples described herein are demonstrated using computational modeling such as Aspen modeling (see, e.g., U.S. Pat. No. 7,666,282). For example, the commercial modeling software Aspen Plus® (Aspen Technology, Inc., Burlington, Mass.) may be used in conjunction with physical property databases such as DIPPR and UNIFAC, available from American Institute of Chemical Engineers, Inc. (New York, N.Y.) to develop an Aspen model for an integrated butanol fermentation, extraction, purification, and water management process. This process modeling can perform many fundamental engineering calculations, for example, mass and energy balances, vapor/liquid equilibrium, and reaction rate computations. In order to generate an Aspen model, information input may include, for example, experimental data, water content and composition of feedstock, temperature for mash cooking and flashing, saccharification conditions (e.g., enzyme feed, starch conversion, temperature, pressure), fermentation conditions (e.g., microorganism feed, glucose conversion, temperature, pressure), degassing conditions, solvent columns, pre-flash columns, condensers, evaporators, centrifuges, and so forth.

Example 1A: Biocompatibility of Triisobutylene with Ethanologen

Into each of two 125 ml shake flasks, 20 ml of an aqueous culture medium containing glucose at a concentration of 21 g/liter and a 0.5 OD suspension of a naturally occurring ethanologen yeast strain was added. A volume of 10 ml of triisobutylene (Tokyo Chemical Industry Co., >90% mixture of isomers, with an estimated log P of 5.8) was added on top of the aqueous suspension of one of the flasks. These flasks were placed in an incubating oven controlled at 32° C. and continuously shaken. After 4 hours, the aqueous phases of both flasks were analyzed and found to contain less than 0.1 g/liter glucose. No significant difference in glucose uptake was observed between the two flasks.

Example 1B: Biocompatibility of Triisobutylene with Isobutanolagen

Two 125 ml flasks were individually prepared with twenty milliliters (20 ml) of an aqueous culture medium containing glucose at a concentration of twenty-eight grams per liter (28 g/L) to which a zero point five (0.5) OD suspension of a genetically modified isobutanolagen yeast strain (PNY2141) was added. Ten milliliters (10 ml) of triisobutylene (Tokyo Chemical Industry Co., >90% mixture of isomers, with an estimated log P of 5.8) was added on top of the aqueous suspension to one of the flasks. The flasks were placed in an incubating oven controlled at thirty-two degrees Celsius (32° C.) and continuously shaken. The glucose concentration and OD were monitored for each of the two flasks. Table 2, reproduced below indicates the results from the monitored flasks.

Growth was monitored by measuring OD and glucose concentration. Some impedance to growth was observed in the flask containing the triisobutylene.

TABLE 2

OD and glucose concentrations for isobutanol extraction with triisobutylene

| | No Solvent | | With solvent | |
|---|---|---|---|---|
| Time, hr | OD | Glucose, gpl Grams per Liter | OD | Glucose, gpl Grams per Liter |
| 0 | 0.5 | 28 | 0.5 | 28 |
| 6 | 0.7 | 26 | 0.6 | 27 |
| 10 | 1.0 | 24 | 0.8 | 26 |
| 19 | 3.7 | 12 | 1.6 | 22 |
| 23 | 4.5 | 2 | 2.1 | 21 |
| 30 | 4.4 | 0 | 2.8 | 14 |
| 35 | 4.3 | 0 | 3.4 | 10 |

Example 2: Biocompatibility of a Triisobutylene-COFA Mixture

Into each of two 125 ml flasks, 20 ml of an aqueous culture medium containing glucose at a concentration of 32 g/liter and a 0.5 OD suspension of a genetically modified isobutanologen yeast strain was added. A volume of 10 ml of a 50% mixture of triisobutylene (Tokyo Chemical Industry Co., >90% mixture of isomers, with an estimated log P of 5.8) and corn oil fatty acid was added on top of the aqueous suspension of one of the flasks. These flasks were placed in an incubating oven controlled at 32° C. and continuously shaken. Growth was monitored by measuring OD. No significant difference in growth was observed between the two flasks as shown in Table 3.

TABLE 3

OD values for an isobutanologen grown in the presence and absence of a 50:50 mixture of triisobutylene and corn oil fatty acid (COFA).

| Time (hr) | OD with No Solvent | OD with solvent |
|---|---|---|
| 0 | 0.5 | 0.5 |
| 7 | 0.9 | 0.9 |
| 13 | 1.5 | 1.6 |
| 23 | 3.7 | 3.1 |
| 29 | 4.1 | 4.0 |
| 37 | 4.3 | 4.3 |
| 50 | 5.0 | 5.0 |
| 60 | 5.4 | 5.5 |

Example 3: Biocompatibility of Isododecane

Into each of two 125 ml flasks, 20 ml of an aqueous culture medium containing glucose at a concentration of 32 g/liter and a 0.5 OD suspension of a genetically modified isobutanolagen yeast strain was added. A volume of 10 ml of isododecane (Alfa Aesar Technical grade mixture of isomers, with an estimated log P of six point two (6.2)) was added on top of the aqueous suspension of one of the flasks. These flasks were placed in an incubating oven controlled at 32° C. and continuously shaken. Growth was monitored by measuring glucose uptake and OD. No significant difference in growth was observed between the two flasks as shown in Table 3, directly below.

TABLE 3

OD and glucose values for an isobutanologen grown in the presence/absence of isododecane

| | No Solvent | | With Solvent | |
|---|---|---|---|---|
| Time (hr) | OD | Glucose (g/L) | OD | Glucose (g/L) |
| 0 | 0.5 | 32 | 0.5 | 32 |
| 7 | 0.9 | 32 | 0.9 | 32 |
| 13 | 1.5 | 25 | 1.6 | 25 |
| 23 | 4.8 | 5 | 4.9 | 5 |
| 29 | 4.1 | 0.1 | 5.0 | 0.1 |

Example 4: Isobutanol Partitioning Between Triisobutylene and Water

Into a small round bottom flask, 10 ml of an aqueous solution containing isobutanol at a concentration of 6 wt % and 1 ml of triisobutylene (Tokyo Chemical Industry Co., >90% mixture of isomers, with an estimated log P of 5.8) were combined. The liquids were mixed thoroughly and then centrifuged to separate into organic and aqueous layers. A sample of the organic layer was analyzed by gas chromatography and found to contain 9.03 wt % (or 18.39 mole %) isobutanol. A sample of the aqueous layer was analyzed by gas chromatography and found to contain 5.28 wt % (or 1.33 mole %) isobutanol. The mass partitioning coefficient is calculated to be 1.71 and the molar partitioning coefficient was calculated to be 13.8.

Example 5A: Isobutanol Partitioning Between Isododecane and Water (First Condition Set)

Into a small round bottom flask, 10 ml of an aqueous solution containing isobutanol (Sigma-Aldrich Co. LLC, St. Louis, Mo., USA, reagent grade) at a concentration of 6 wt % and 1 ml of isododecane (Alfa Aesar Technical grade mixture of isomers, with an estimated log P of six point two (6.2)) were combined. The liquids were mixed thoroughly and then centrifuged to separate into organic and aqueous layers. A sample of the organic layer was analyzed by gas chromatography and found to contain 8.31 wt % (or 17.24 mole %) isobutanol. A sample of the aqueous layer was analyzed by gas chromatography and found to contain 5.45 wt % (or 1.39 mole %) isobutanol. The mass partitioning coefficient is calculated to be 1.525 and the molar partitioning coefficient was calculated to be 12.4.

Example 5B: Isobutanol Partitioning Between Isododecane and Water (Second Condition Set)

Into a sample vial, three grams (3 g) of an aqueous solution containing isobutanol at a concentration of two point zero weight percent (2.0 wt %) and three (3 g) of isododecane were combined. The liquids were mixed thoroughly and then centrifuged to separate into organic and aqueous layers. A sample of the aqueous layer was analyzed by HPLC and found to contain one point six zero weight percent (1.60 wt %) isobutanol and the organic layer was calculated by mass balance to contain zero point four zero weight percent (0.40 wt %) isobutanol. The mass partitioning coefficient was calculated to be zero point two five (0.25).

Example 6A: Biocompatibility of 1,3-Diisopropylbenzene

Into a 125 ml flask, twenty milliliters (20 ml) of an aqueous culture medium containing glucose at a concentration of thirty grams per liter (30 g/liter) and a one point zero 1.0 OD suspension of a genetically modified isobutanolagen yeast strain (PNY2141) was added. A volume of 10 ml of 1,3-diisopropylbenzene (Sigma-Aldrich Co. LLC, St. Louis, Mo., USA, (Aldrich) reagent grade, with an estimated log P of four point nine (4.9)) was added on top of the aqueous suspension. The flask was placed in an incubating oven controlled at thirty-two degrees Celsius (32° C.) and continuously shaken. Growth was monitored by measuring glucose. No significant consumption of glucose was observed. Results of this analysis are reported in Table 4, directly below.

TABLE 4

Glucose Levels for 1,3-diisopropylbenzene

| Time (hours) | Glucose (grams per liter, gpl) |
|---|---|
| 0 | 30 |
| 6 | 30 |
| 11 | 30 |
| 16 | 28 |
| 24 | 29 |

Example 6B: Biocompatibility of 1,3,5-Triisopropylbenzene

In this example, a 1.0 OD suspension of a genetically modified isobutanolagen yeast strain PNY2310 is added to a 125 ml flask including 20 ml of an aqueous culture medium containing glucose at a concentration of 29 g/liter. Ten milliliters (10 ml) of 1,3,5-triisopropylbenzene (Sigma-Aldrich, reagent grade, with an estimated log P of 6.2) was added on top of the aqueous suspension. The flask including the sample was maintained at thirty-two degrees Celsius (32° C.) in an incubating oven with continuous shaking Glucose was measured to monitor its consumption. No significant inhibition in glucose consumption was observed with the inclusion of the triisopropylbenzene. Table 5, directly below, indicates the results. As can be observed, addition of an isopropyl group made a significant impact. This impact may be attributed to the presence of the propyl group.

TABLE 5

Glucose Levels for 1,3,5-Triisopropylbenzene

| Time (hours) | Glucose (grams per liter, gpl) |
|---|---|
| 0 | 29 |
| 6 | 25 |
| 11 | 20 |
| 16 | 12 |
| 24 | 1 |

Example 7: Isobutanol Partitioning Between 1,3,5-Triisopropylbenzene and Water

In an example, five point two grams (5.2 g) of triisopropylbenzene (Sigma-Aldrich, reagent grade) and an aqueous solution containing isobutanol at a concentration of two point four weight percent (2.4 wt %) were combined in a sample vial. The 1,3,5-triisopropylbenzene and aqueous solution were thoroughly mixed and centrifuged to separate the organic and aqueous layers from one another. Analysis of a sample obtained from the organic layer, e.g., the layer containing 1,3,5-triisopropylbenzene, was analyzed using gas chromatography as described in the section captioned "confirmation of isobutanol production." This analysis indicated the organic lay included one point one eight weight percent (1.18 wt %) isobutanol. A sample obtained from the aqueous layer was analyzed using high pressure liquid chromatography (HPLC) as described in the section captioned "confirmation of isobutanol production." This analysis indicated that the aqueous layer contained one point eight four weight percent (1.84 wt %) isobutanol. The mass partitioning coefficient was calculated from the weight percentages in the organic and aqueous layers, the mass partitioning coefficient was zero point six four (0.64).

Example 8: Isobutanol Partitioning Between 1,3,5-Triisopropylbenzene/Thymol Blend and Water In an example, zero point two five grams (0.25 g) of thymol (Sigma-Aldrich Co. LLC, St. Louis, Mo., USA, reagent grade) was combined with ten point two five grams (10.25 g) of aqueous solution that contained isobutanol at a concentration of two point four weight percentage (2.4 wt %) in a sample vial and four point seven five grams (4.75 g) of 1,3,5-triisopropylbenzene. The thymol, 1,3,5-triisopropylbenzene, and aqueous solutions were thoroughly mixed and centrifuged to form an organic layer and an aqueous layer. Gas chromatograph was used to analyze a sample obtained from the organic layer. The organic layer sample was determined to contain two point three zero weight percent (2.30 wt %) of isobutanol as described in the section captioned "confirmation of isobutanol production." A sample from the aqueous layer was analyzed using HPLC. The aqueous sample was determined to contain one point three seven weight percent (1.37 wt %) isobutanol as described in the section captioned "confirmation of isobutanol production." The mass partitioning coefficient was calculated from the weight percentages in the organic and aqueous layers, the mass partitioning coefficient was one point seven zero (1.70).

In embodiments, thymol exhibits fungicidal properties. Thymol can be used to break down yeast cells resulting in lysis of the cells, for example. In some embodiments, thymol exhibited in vitro antifungal properties to *Sacchromyces Cerevisiae* at 1.5 mM (MIC, minimum inhibitory concentration) concentration while the MFC (minimum fungal concentration) was 1.8 mM. Examples of thymol's fungicidal properties are reported in Bennis et al., *Surface Alteration of Sacchromyces Cerevisiae Induced by Thymol and Eugenol*, 38 Letters in Applied Microbiology 454-458 (2004), which is hereby incorporated by reference in its entirety.

Thymol may be of interest as its partition coefficient (Kd) for water/butanol/solvent (e.g., is calculated from an equilibrium ternary mixture of water/butanol/solvent) is greater than twenty-five (>25) and is, comparatively, much less hindered than BHT. Thymol is naturally occurring (main extract of thyme) and considered GRAS (generally recognized as safe). It is used as a nontoxic insect repellant. It can serve as an antioxidant. It also is antibacterial but was shown to be equally damaging to yeast. In embodiments a recombinate microorganism (such as genetically modified butanologen) can be evolved in the presence of thymol and/or a COFA thymol mixture so the microorganism can outgrow yeast or bacteria that naturally occur in the same environment. In embodiments such as this, the COFA thymol mixture can exhibit high Kd and be implemented as an extraction solvent that is oxidatively stable. The log P for thymol is 3.3. Accordingly, the biocompatibility of thymol is sufficient so in some embodiments thymol is included in the mixture with COFA at or approximately at or below ten percent (10%) by volume. In some examples, a ten percent thymol/COFA mix has a Kd of four point eight (4.8). For comparison, some thymol/COFA mixes under ten percent (10%) by volume exhibit a Kd of at or approximately at three (3). Accordingly, thymol/COFA exhibits greater synergy with respect to Kd in comparison to thymol/corn oil.

Example 9: Biocompatibility of Tetrabutylurea

Into each of two 125 ml flasks, twenty milliliter (20 ml) of an aqueous culture medium containing glucose at a concentration of twenty-eight grams per liter (28 g/L) and a 0.5 OD suspension of a genetically modified isobutanolagen yeast strain PNY2310 was added. A volume of ten milliliters (10 ml) of tetrabutylurea ((Tokyo Chemical Industry Co., estimated log P of six point six (6.6)) was added on top of the aqueous suspension of one of the flasks. These flasks were placed in an incubating oven controlled at thirty-two degrees Celsius (32° C.) and continuously shaken. Growth was monitored by measuring glucose concentration. No significant difference was observed between the two flasks. The results are shown in Table 6, directly below.

TABLE 6

Glucose concentration for an isobutanologen grown in the presence/absence of tetrabutylurea

| Time (hr) | No Solvent Glucose (g/L) | With Solvent Glucose (g/L) |
|---|---|---|
| 0 | 28 | 28 |
| 4 | 25 | 25 |
| 8 | 14 | 14 |
| 12 | 1 | 0 |

Example 10A: Isobutanol Partitioning Between Tetrabutylurea and Water

Into a sample vial, five grams (5 g) of an aqueous solution containing isobutanol (Sigma-Aldrich Co. LLC, St. Louis, Mo., USA, reagent grade) at a concentration of two point zero weight percent (2.0 wt %) and two point five (2.5 g) of tetrabutylurea ((Tokyo Chemical Industry Co., estimated log P of six point six (6.6)) were combined. The liquids were mixed thoroughly and then centrifuged to separate into organic and aqueous layers. A sample of the aqueous layer was analyzed by HPLC and found to contain zero point four one seven weight percent (0.417 wt %) isobutanol and the organic layer was calculated by mass balance to contain three point zero six weight percent (3.06 wt %) isobutanol. The mass partitioning coefficient was calculated to be seven point three five (7.35).

Example 10B: Isobutanol Partitioning Between an Isododecane/Tetrabutylurea Blend and Water Into a sample vial, three grams (3 g) of an aqueous solution containing isobutanol (Sigma-Aldrich Co. LLC, St. Louis, Mo., USA, reagent grade) at a concentration of two point zero weight percent (2.0 wt %), one point five grams (1.5 g) of isododecane (Alfa Aesar Technical grade mixture of isomers, with an estimated log P of six point two (6.2)) and one point five grams (1.5 g) of tetrabutylurea (Tokyo Chemical Industry Co., estimated log P of six point six (6.6)) were combined. The liquids were mixed thoroughly and then centrifuged to separate into organic and aqueous layers. A sample of the aqueous layer was analyzed by HPLC and found to contain zero point four six weight percent (0.46 wt %) isobutanol and the organic layer was calculated by mass balance to contain one point five three weight percent (1.53 wt %) isobutanol. The mass partitioning coefficient was calculated to be three point three three (3.33). See also Example 5B for isobutanol partitioning between isododecane and water.

Example 11A: Isobutanol Partitioning Between 2,6,8-Trimethyl-4-Nonanol (an Isododecanol) and Water Into a sample vial, five grams (5 g) of an aqueous solution containing isobutanol (Sigma-Aldrich Co. LLC, St. Louis, Mo., USA, reagent grade) at a concentration of two point zero weight percent (2.0 wt %) and two point five grams (2.5 g) of 2,6,8-trimethyl-4-nonanol (Pfaltz & Bauer, Inc., Waterbury, Conn.) were combined. The liquids were mixed thoroughly and then centrifuged to separate into organic and aqueous layers. A sample of the aqueous layer was analyzed by HPLC and found to contain zero point five three weight percent (0.53 wt %) isobutanol and the organic layer was calculated by mass balance to contain two point eight weight percent (2.87 wt %) isobutanol. The mass partitioning coefficient was calculated to be five point four two (5.42).

Example 11B: Isobutanol Partitioning Between an Isododecane/2,6,8-Trimethyl-4-Nonanol Blend and Water Into a sample vial, five grams (5 g) of an aqueous solution containing isobutanol (Sigma-Aldrich Co. LLC, St. Louis, Mo., USA, reagent grade) at a concentration of two point zero weight percent (2.0 wt %), four point five grams (4.5 g) of isododecane (Alfa Aesar Technical grade mixture of isomers, with an estimated log P of six point two (6.2)) and zero point five grams (0.5 g) of 2,6,8-trimethyl-4-nonanol (Pfaltz & Bauer, Inc., Waterbury, Conn.) were combined. The liquids were mixed thoroughly and then centrifuged to separate into organic and aqueous layers. A sample of the aqueous layer was analyzed by HPLC and found to contain one point three three weight percent (1.33 wt %) isobutanol and the organic layer was calculated by mass balance to contain two point two eight weight percent (2.28 wt %) isobutanol. The mass partitioning coefficient was calculated to be one point seven one (1.71). See also Example 5B for isobutanol partitioning between isododecane and water.

Example 12: Biocompatibility of Tris(2-Ethylhexyl) Phosphate

Into a 125 ml flask, twenty milliliters (20 ml) of an aqueous culture medium containing glucose at a concentration of seventeen grams per liter (17 g/L) and a one point one (1.1) OD suspension of an ethanol red yeast strain was added. A volume of ten milliliters (10 ml) of tris(2-ethylhexyl) phosphate (Sigma-Aldrich Co. LLC, St. Louis, Mo., USA, reagent grade, with an estimated log P of ten point one (10.1)) was added on top of the aqueous suspension. The flask was placed in an incubating oven controlled at thirty-two degrees Celsius (32° C.) and continuously shaken. Growth was monitored by measuring glucose. No significant inhibition in glucose consumption was observed. The results are reported in Table 7, reproduced directly below.

TABLE 7

| Glucose Levels for tris(2-Ethylhexyl) phosphate | |
|---|---|
| Time (hours) | Glucose (grams per liter, gpl) |
| 0 | 17 |
| 2.5 | 11.5 |
| 5 | 0 |

Example 13: Isobutanol Partitioning Between Triisobutylene and Water

Into a sample vial, five grams (5 g) of an aqueous solution containing isobutanol at a concentration of two point zero weight percent (2.0 wt %) and five grams (5 g) of triisobutylene (Tokyo Chemical Industry Co.) were combined. The liquids were mixed thoroughly and then centrifuged to separate into organic and aqueous layers. A sample of the aqueous layer was analyzed by HPLC and found to contain one point five three weight percent (1.53 wt %) isobutanol and the organic layer was calculated by mass balance to contain zero point four seven weight percent (0.47 wt %) isobutanol. The mass partitioning coefficient was calculated to be zero point three one (0.31). See also Example 4 for this system under different conditions.

Example 14: Isobutanol Partitioning Between Tributyl Phosphate and Water

Into a sample vial, five grams (5 g) of an aqueous solution containing isobutanol at a concentration of two point zero weight percent (2.0 wt %) and two point five grams (2.5 g) of tributyl phosphate (Sigma-Aldrich Co. LLC, St. Louis, Mo., USA, reagent grade) were combined. The liquids were mixed thoroughly and then centrifuged to separate into organic and aqueous layers. A sample of the aqueous layer was analyzed by HPLC and found to contain zero point three three weight percent (0.33 wt %) isobutanol and the organic layer was calculated by mass balance to contain three point two two weight percent (3.22 wt %) isobutanol. The mass partitioning coefficient was calculated to be nine point eight (9.8).

Example 15: Isobutanol Partitioning Between DEET and Water

Into a sample vial, one gram (1 g) of an aqueous solution containing isobutanol at a concentration of two point zero weight percent (2.0 wt %) and zero point five grams (0.5 g) of DEET (Sigma-Aldrich Co. LLC, St. Louis, Mo., USA, reagent grade) were combined. The liquids were mixed thoroughly and then centrifuged to separate into organic and aqueous layers. A sample of the aqueous layer was analyzed by HPLC and found to contain zero point three four weight percent (0.34 wt %) isobutanol and the organic layer was calculated by mass balance to contain three point one seven weight percent (3.17 wt %) isobutanol. The mass partitioning coefficient is calculated to be nine point two (9.2).

Example 16: Isobutanol Partitioning Between Carvacrol and Water

Into a sample vial, five grams (5 g) of an aqueous solution containing isobutanol at a concentration of two point zero weight percent (2.0 wt %) and two point five grams (2.5 g) of carvacrol (Sigma-Aldrich Co. LLC, St. Louis, Mo., USA, reagent grade) were combined. The liquids were mixed thoroughly and then centrifuged to separate into organic and aqueous layers. A sample of the aqueous layer was analyzed by HPLC and found to contain zero point two two weight percent (0.22 wt %) isobutanol and the organic layer was calculated by mass balance to contain three point four two weight percent (3.42 wt %) isobutanol. The mass partitioning coefficient is calculated to be fifteen point five (15.5).

Example 17: Solubility of Water in Solvents

By way of example, a study was conducted using Aspen Plus simulation software (Aspen Technology, Inc., Burlington, Mass., U.S.A.) to compare three solvents. The solvents studied were corn oil fatty acid (COFA), oleyl alcohol and isolauryl alcohol (ISOLAUR). Table 3 shows the equilibrium water content in the solvents in the presence of about two percent by weight (2 wt %) butanol at about thirty-two degrees Celsius (32° C.).

TABLE 8

Water content of different solvents

| Solvent | Water Content, wt % |
|---------|---------------------|
| COFA    | 0.84                |
| Oleyl   | 1.5                 |
| ISOLAUR | 2.0                 |

Figure 9:
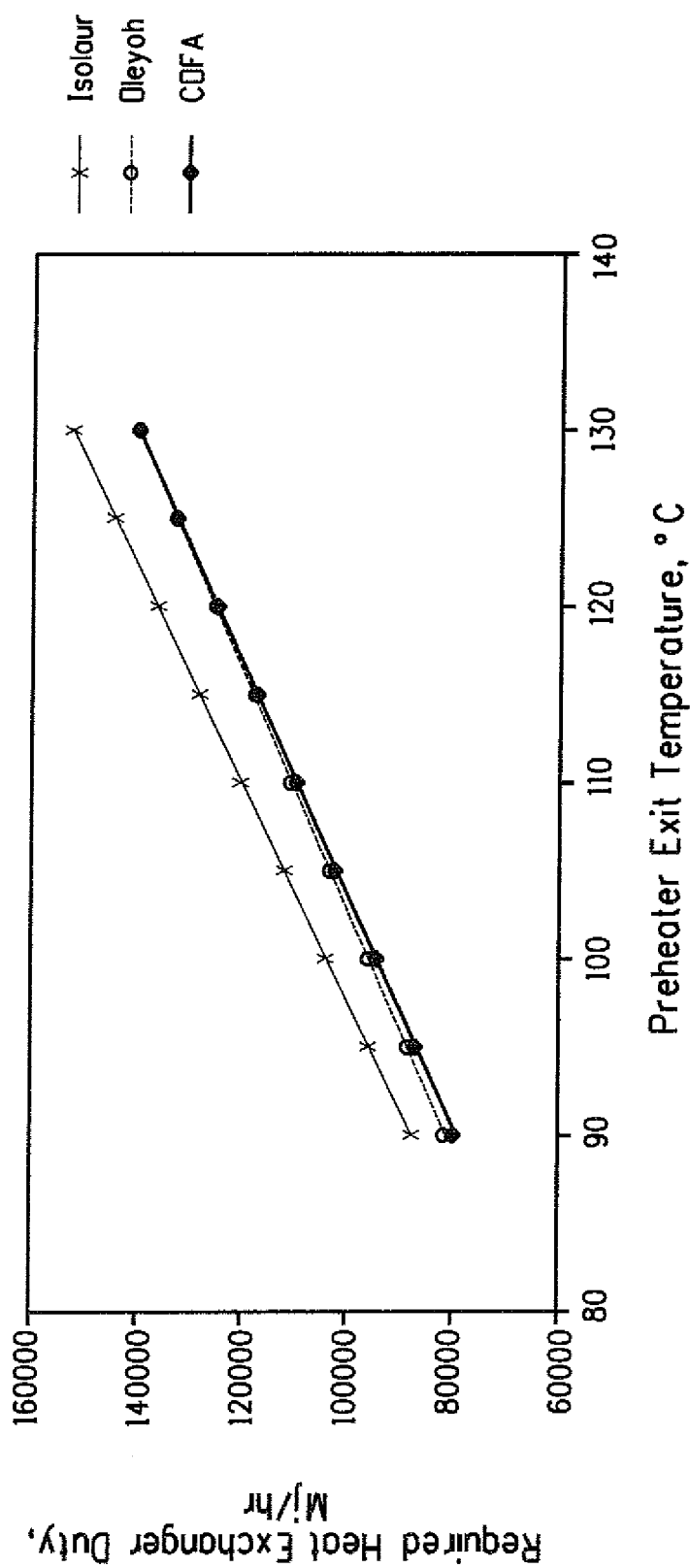
FIG. 9 is a graph showing the relationship between water content and heat requirement to reach a preheater exit temperature.

In this example a mixture of organic solvent, butanol and water was preheated under pressure before distilling to remove butanol from the solvent. In all cases, the butanol concentration in the solvent was about two percent by weight (2 wt %) and the feed temperature to the heat exchanger was about thirty-two degrees Celsius (32° C.). The temperature of the preheater was varied between ninety degrees Celsius (90° C.) and one hundred thirty degrees Celsius (130° C.) prior to entering the distillation unit. The variable of interest was the required heat duty to raise the mixture to the preheat temperature. Results as shown in FIG. 9, demonstrated that, from the selected solvents, a higher water content in the feed led to a greater heat requirement to reach a given temperature. For each composition the water content was fixed at its equilibrium value presented in the Table 8. In each mixture, the mass of butanol and solvent was identical.

Figure 10:
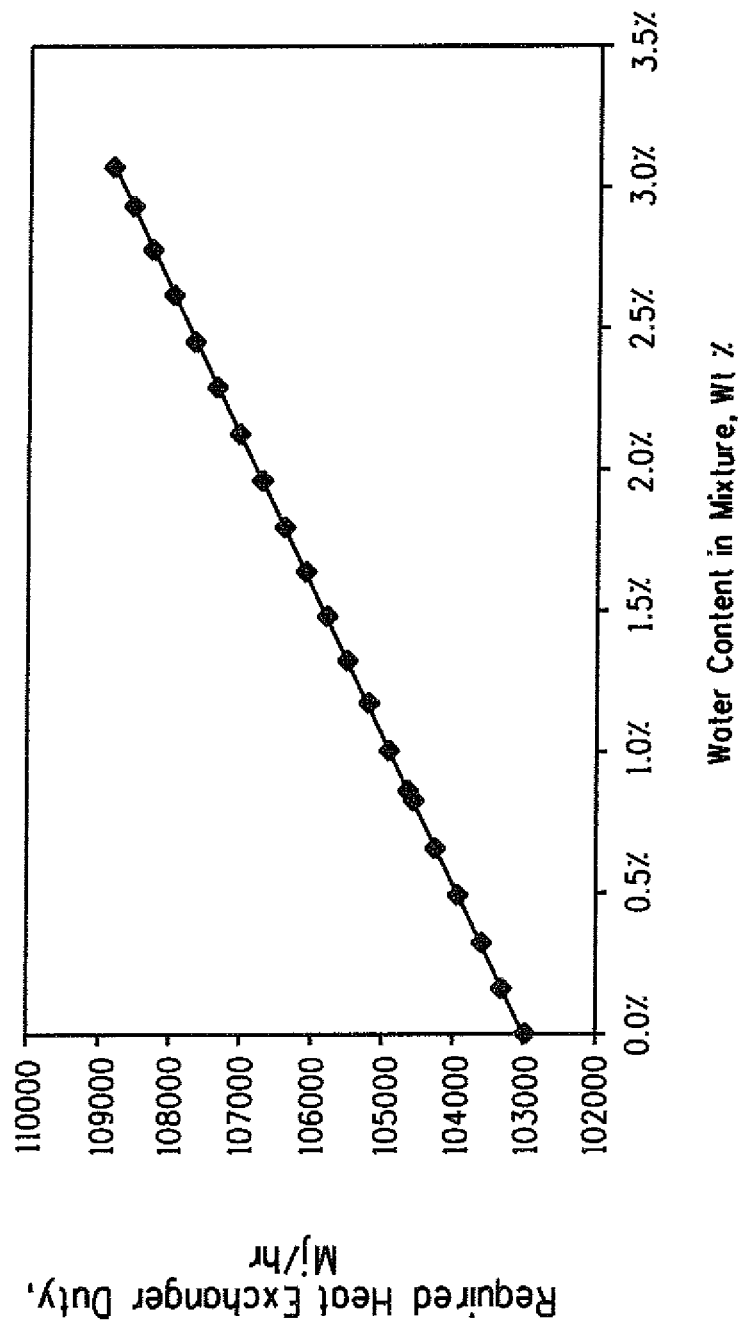
FIG. 10 is a graph showing the relationship between the water content and heat requirement to reach a heat exchanger temperature of 100° C.

For a given solvent in a mixture of solvent, water and butanol, the required heat duty to reach a given temperature is sensitive to the amount of water present. A separate study was conducted using Aspen Plus simulation software to show the required heat duty to reach a given temperature as a function of water content in a mixture of triisobutylene, butanol, and water. Water content was varied from zero percent (0%) to about three percent (3%) with a fixed heat exchanger temperature of one hundred degrees Celsius (100° C.). The additional water load in the stream led to an increase in required heat exchanger duty as demonstrated in FIG. 10.

Discussion of Examples

In embodiments, the base solvent is chosen to be dry, but it may not exhibit sufficient butanol affinity, e.g., isobutanol affinity. The base solvent in these embodiments can be chosen to have excess biocompatibility. A solvent's biocompatibility can be correlated to the solvent's log P value. In some embodiments, it is preferable to form a mix of solvents where one solvent (e.g., a base solvent or first solvent) exhibits high biocompatibility while the other solvent (e.g., a second solvent) exhibits other characteristics (e.g., high affinity to butanol, exhibit a synergistic effect in a solvent mix), but it may exhibit lower or poor biocompatibility. Solvents can be selected based on the mixture's properties that can differ from those of the solvents or those predicted from the properties of the solvents forming the mixture according to each solvent's molar ratio in the mixture. For some butanol-producing organisms, a maximum log P of six (6) or of approximately six (6) indicates biocompatible, such as biocompatibility for a butanologen (e.g., a microorganism genetically modified to produce butanol). This is to say that for some fermentation systems hydrophobicity is associated with biocompatibility or toxicity.

A log P of six (6) may correspond to an equilibrium, saturated concentration of solvent in the aqueous phase of zero point two parts per million (0.2 ppm) or approximately zero point two parts per million (0.2 ppm). At this concentration, the solvent may be sufficiently dispersed in the aqueous phase to avoid interfering with the microorganism's metabolism of sugar (glucose) to alcohol. Increasing the concentration of solvent in the aqueous phase, to for example zero point three parts per million (0.3 ppm) or approximately zero point three parts per million (0.3 ppm) can have a detrimental impact on a microorganism's ability to produce alcohol. Additionally, for example, a solvent can hinder fermentation if it has a high affinity for nutrients used by the microorganism in fermentation. A solvent may hinder a microorganism by interfering with the integrity of the microorganism's membrane (cell membrane). Increasing the concentration of solvent in the aqueous phase can impact the membrane's rigidity because the membrane is generally oleophillic and includes sterols. The presence of solvent adjacent to microorganism can increase the number of holes in the cell membrane and impact transport of one or more of sugar, glucose, product alcohol, nutrients, and so forth across the cell membrane. Some solvents if present in sufficient concentration in the aqueous phase can impact the cell membrane's rate of repair. For instance, examples 6A and 6B illustrate how an aromatic hydrocarbon can be made to be biocompatible with a proper amount of alkyl substitution. A diisopropyl benzene solvent with a log P below 6 was found not to be biocompatible. By adding an additional isopropyl group onto the aromatic ring, the resulting triisopropyl benzene solvent with a log P greater than 6 was found to be biocompatible, e.g., biocompatible with a butanologen.

In embodiments, log P of approximately six (6) comprise a log P of 5.5, 5.6, 5.7, 5.8, 5.9, 6.0, 6.1, 6.2, or 6.3. If log P is much greater than six (6), in embodiments, a second solvent that is not biocompatible is blended with the base solvent to form a biocompatible binary mixture. Although, a log P of six (6) is described, it is to be appreciated that different microorganism may have different sensitivities to the presence of solvent in the aqueous phase, which may also depend on the solvent's properties. For example, a second solvent is chosen that exhibits a high product alcohol affinity (e.g., a high butanol affinity) in comparison to the first solvent, but may exhibit low or poorer biocompatibility or hydrophobicity as an indicator of biocompatibility than the first solvent. It is to be apparent that multiple solvents can be implemented and/or the solvent mixture is tailored to balance biocompatibility with affinity towards the fermentation product, and so forth. Other properties impacting solvent selection include, but are not limited to, affinity to water, dryness, solubility, its distribution coefficient, reactivity, interfacial tension, viscosity, boiling point, or freezing point. Other factors include cost, density, flammability, selectivity to the fermentation product, thermal stability, and so forth. In examples, much greater than six (6) comprises 6.1, 6.2, 6.3, 6.4, 6.5, 6.6, 6.7, 6.8, 6.9. In some examples, the second solvent provides exceptionally high butanol affinity but may not be dry. Of interest, surprisingly the moisture content of some solvent mixtures can vary nonlinearly with composition and the equilibrium moisture content of any linear combination of solvents is usually less than the linear combination of individual equilibrium solvents moisture content. The log P of linear combination of solvents can be less or different than the linear combination of solvent log P values. The Kd of linear combination of solvents can be different than the linear combination of Kd values.

In embodiments, the log P for a solvent is calculated from an equilibrium ternary mixture of solvent, octanol, and water as the ratio of the molar concentration of the solvent in the organic phase to the molar concentration of the solvent in the aqueous phase under dilute conditions. In embodiments such as these, five milliliters (5 ml) of a zero point zero zero one (0.001) molar solution of the solvent (e.g., a first or second solvent or a solvent mixture) in octanol is mixed and brought to phase equilibrium with thirty milliliters (30 ml) of water, sampled and then analyzed.

The log P for a solvent can be determined experimentally or by property estimation. The log P of a binary mixture can be measured or calculated from the individual solvent log P values, the molar composition and a rigorous non-ideal thermodynamic properties mixing model. In an embodiment, an Aspen Model (Aspen Plus simulation software) was constructed that features pure component property estimation by DIPPR and a UNIFAC model for estimating multicomponent phase equilibrium of mixtures. It is to be understood that "pure component property" refers generally to a property of an individual solvent, not necessarily that the solvent/component lacks any impurities. For most or all solvents, the log P value calculated by the Aspen Model agrees well with experimentally determined log P values. Simulations were carried out that predict the equilibrium molar concentrations of solvent components introduced to the organic and aqueous phases formed from a mixture of octanol and water. In addition, the partitioning coefficient of isobutanol in various solvent mixtures can be estimated by replacing octanol with isobutanol. In these embodiments, a small amount of isobutanol is introduced to a mixture of the solvent components and water. The partitioning coefficient is calculated as the ratio of the mass concentration of isobutanol in the equilibrium organic phase to the mass concentration of isobutanol in the equilibrium aqueous phase.

Triisopropylbenzene was identified as a base solvent. It has an estimated log P of six point two (6.2). The triisopropylbenzene was tested, and was found to be biocompatible with a butanologen. Triisopropylbenzene has a normal boiling point of two-hundred thirty-six degrees Celsius (236° C.) and a density of zero point eight five grams per cubic centimeter (0.85 g/cm$^3$).

Further, isododecane (2,2,4,6,6-pentamethylheptane) was identified as a base solvent. Isododecane has an estimated log P of six point two (6.2). The isododecane tested was found to be biocompatible with a butanologen. Isododecane has a boiling point of one-hundred seventy-seven degrees Celsius (177° C.) and a density of zero point seven five grams per cubic centimeter (0.75 g/cm$^3$).

Additionally, isohexadecane (2,2,4,4,6,8,8-heptamethylnonane) was identified as a base solvent. Isohexadecane has an estimated log P of eight point zero (8.0) and is predicted to be biocompatible with a butanologen. Isohexadecane has a boiling point of two-hundred forty degrees Celsius (240° C.) and a density of zero point seven eight grams per cubic centimeter (0.78 g/cm$^3$).

In addition, corn oil triglyceride (COTG) was identified as a base solvent. COTG has an estimated log P of 22.0-24.0 and is predicted to be biocompatible. It has a density of 0.9 g/cm3.

Tetrabutylurea was also identified as a base solvent. Tetrabutylurea has an estimated log P of six point six (6.6). Tetrabutylurea was found to be biocompatible with a butanologen in testing. Tetrabutylurea has a boiling point of three-hundred eighty degrees Celsius (380° C.) and a density of zero point nine grams per cublic centimeter (0.9 g/cm3). Tetrabutylurea has a high partitioning coefficient for isobutanol. Other shorter chain tetraalkyl ureas that have a log P below six (6) but have a high partitioning coefficient for isobutanol are considered as a second solvent.

Further, Bisphenol A was identified as a second solvent. Bisphenol A has an estimated log P of three point four (3.4).

Additionally, DEET (diethyl m-toluamide) was identified as a second solvent. DEET has an estimated log P of two point zero (2.0).

In addition, Di-tert-amylphenol was identified as a second solvent. Di-tert-amylphenol has an estimated log P of five point nine (5.9). Other unhindered alkylated phenols can be used as a second solvent. For example, di-tert-butylphenol has an estimated log P of 4.9. Oil of thyme and oil of oregano, both isomers of methyl isopropyl phenol, can be used as a second solvent and are considered environmentally benign. Oil of thyme and oil of oregano have an estimated log P of three point three (3.3).

Discussion of Sample Solvent Mixture Preparation and Extraction

The following description provides sample techniques, approaches, methods, for selection, preparation, and use of solvent mixtures. As should be apparent, the techniques, approaches, methodologies described herein are applicable to solvents described throughout this disclosure. While the methodologies are described in conjunction with a binary solvent mixture, multiple solvent mixtures (ternary, quaternary, and so on) can benefit from the techniques described herein.

In embodiments, a method of extracting alcohol from an aqueous solution, such as fermentation broth, comprises selecting which solvents are to be included in the solvent mixture. This selection can be based on the individual solvent's properties (e.g., a property of that solvent). Example properties include, but are not limited to, hydrophobicity (log P), hydrophobicity/log P as an indicator of biocompatibility, Kd, moisture content, and so on. Although the solvents and their respective properties are considered on an individual basis, in some embodiments selecting includes identifying a solvent with a property that is beneficial in a particular aspect (relative to the extraction to be performed) in comparison to another solvent that exhibits that property, but to a lesser extent or exhibits that property negatively (e.g., an unfavorable property). An example of an unfavorable property is a solvent that is highly toxic to a butanologen when butanol is to be extracted from a fermentation broth that includes butanologens. In another example, a second solvent is identified that exhibits high biocompatibility to account for a first solvent that exhibits comparatively poorer biocompatibility, but also exhibits a beneficial property such as high Kd, low moisture, high selectivity to butanol, if the solvent mixture is used to extract butanol. Accordingly, the solvents can be selected so the resultant solvent mixture is generally balanced, e.g., so the solvent mixture overall exhibits good properties rather than exhibiting one beneficial property strongly while exhibiting other relevant properties weakly, poorly, or even negatively.

Moreover, while selection can include considering each solvent and/or each solvent's properties individually, this can be done within a framework of the other solvents to be included in the solvent mixture. The individual solvent's chemical structures can be considered when determining which solvents are to be selected. For example, the heuristic of "like-dissolves-like" can be applied to solvent selection from the solvents identified. Put another way, selection of which solvents to include in the solvent mixture can include considering the individual solvent's chemical structures. Other approaches can be used as well, e.g., including particular functional groups, chemical properties (e.g., para, ortho, meta substituents) and so on. For example, two solvents are selected because both have aromatics in their respective backbones. Additional examples include selecting two solvent as both are aliphatic and branched.

In some embodiments, chemical structure is a threshold criteria that is to be met before solvent properties are considered. In other embodiments, chemical structure can be considered in parallel with identifying the solvents and/or the solvent properties. For instance, two solvents are selected to be included in a binary solvent mixture because they have generally similar structures, and their respective properties when considered overall are substantially balanced or balanced. An example of a substantially balanced solvent mixture is two or more solvents that exhibit "beneficial" strongly or to an acceptable extent while avoiding or exhibiting unfavorable properties to a tolerable level. An example of a tolerable level may be a solvent mixture that exhibits high Kd, but solvates water (e.g., is moist) to a tolerable level for a predetermined set of conditions.

In some implementations, a computing system is configured to select solvents by identifying the solvents based on their respective features and/or chemical structures. In examples such as these, a computing system can be programmed to compare properties associated with various solvent on an individual basis to identify solvents that exhibit properties that benefit the solvent mixture.

The method can further include setting a limit for a ratio of the solvents to be included in the solvent mixture. For example, hydrophobicity can be used as a limit on a ratio of a first solvent to a second solvent to determine a ratio limit for a first and a second solvent. In the preceding example, hydrophobicity can be used as an indicator or "stand-in" for biocompatibility. Thus, in embodiments, the limit is set so the ratio of solvents in the solvent mix does not exceed the limit, thereby being toxic or bio-incompatible with a microorganism producing a fermentation product, e.g., a product alcohol to be extracted. In some instances, the limit is set so the solvent mixture is only slightly or minimally toxic, such as to accommodate solvents that exhibit beneficial features in other aspects. In some instances, the solvent mixture's hydrophobicity is not indicated by a linear combination of the hydrophobicities of the solvent mixture's component solvents, when taking into account each solvent's mole fraction in the solvent mixture.

In other words, the hydrophobicity of the solvent mixture (acting as an indicator of biocompatibility) can be used to set a ratio limit for the solvents to be included in the mixture. For example, a ratio limit of solvent A to solvent B is set at log P of six (6) or substantially six (6) so the mixture of solvents A and B is not toxic to butanologens present in a fermentation broth. The solvent mixture's hydrophobicity is used as the limit, in some embodiments, because the hydrophobicity of the solvent mixture can exhibit a synergistic effect. This is to say that, hydrophobicity is a property that exhibits a synergistic effect (e.g., an impact in a beneficial way) when solvents A and solvent B are mixed to form the solvent mixture. While a log P of six (6) is described herein those of skill in the art will appreciate that some strains of alcohol producing microorganisms exhibit different tolerance levels that can be accounted for.

In some embodiments, the method further includes determining a ratio of the solvents within the limit. For example, an actual ratio of a first and second solvent to be included in the solvent mixture is determined to balance the solvent mixture's overall properties so long as the determined ratio is within the limit, i.e., is not toxic to a microorganism in a fermentation broth. In this general way, the ratio of the solvents in the solvent mixture can be tailored to exhibit at least one synergistic effect so long as the determined ratio is not toxic to the microorganism. The property that is synergistic may not be indicated by a linear combination of the solvents that form the solvent mixture. In other words, the extent of a beneficial property of the solvent mixture is not indicated (for a two solvent mixture) by a linear combination of a first and second solvents' respective properties when considering their mole fraction in the solvent mixture. For example, a solvent mixture's Kd is different in a beneficial way than that which would be expected based on the Kd for a first and second solvent, respectively. The previous example, generally illustrates a situation in which one solvent exhibits a greater impact on the solvent mixture's Kd than the other solvent's Kd for a two solvent mixture. These principles can be applied to solvent mixtures with more than two solvents. In tertiary solvent mixtures, the Kd for the individual solvents (for clarity, solvents A, B, and C) can have different impacts. Thus, solvents A's Kd and solvent B's Kd can have a proportionally larger impact the solvent mixture's Kd than that of solvent C, i.e., solvent C's Kd. In other tertiary solvent mixtures, solvent A's moisture can have a greater impact on the solvent mixture's moisture, than that of solvents B and C, when considered individually. Additional examples included, but are not limited to, alcohol selectivity, hydrophobicity as an indicator of biocompatibility, toxicity/biocompatibility (indicated directly), and so on.

In embodiments, the selected solvents are combined by mixing the component solvents in the determined ratio so the solvent mixture that results is balanced and exhibits at least one synergistic alcohol extraction property that is not indicated by a linear combination of the solvents' properties and is beneficial for the extraction to be performed. In additional embodiments, a solvent mixture exhibits more than one synergistic property.

The solvent mix that results from combining the solvents can be contacted with the aqueous solution to extract alcohol present in the water into the solvent/organic phase. For example, the solvent mixture is contacted with fermentation broth that can include, among other constituents, water, butanol, butanologen microorganisms, nutrients and so forth.

Optionally, additives are incorporated into the solvent mixture. Example additives include, but are not limited to one or more of antioxidants, antimicrobial agents, additives included to vary the solvent mixture's properties (e.g., "salts") and so forth.

Optionally, in embodiments, the method further comprises maintaining the solvent mixture so it exhibits predetermined properties. For example, additional solvent mixture is added to adjust its concentration in a fermentation system, an additional amount of a component solvent is added, and so forth.

In embodiments, a method for drying an extractant includes contacting a first solvent with a fermentation broth to extract alcohol from the broth. For example, a dry solvent or a solvent mixture is contacted with fermentation broth pumped through an external loop from a fermentor to extract the alcohol. Generally, like that of the other solvents (including a solvent mixture) the first and/or second solvents can be implemented in a countercurrent extraction configuration. In addition to extracting alcohol, the first solvent can also solubilize at least some water from the broth before the lean broth is returned to the fermentor. The rich solvent, e.g., extractant including alcohol, now additionally includes water. In examples of the present embodiment, the water is removed by contacting the first solvent that includes the alcohol and water with a second solvent. This extraction can be performed outside the presence of the fermentation broth, as second solvent would likely be overwhelmed by the water in the fermentation broth. The second solvent in these embodiments is a dry solvent that exhibits a high affinity to water. The second solvent in the previous embodiment may be a hydrophilic solute, such as described above. Glycerol, for example, is used to extract the water from a solvent mixture before the solvent mixture including the alcohol is transferred for distillation. Extracting water from rich solvent can avoid drawbacks associated with distilling in-part water from the product alcohol and solvent. Example drawbacks include, but are not limited to increased volume, increased energy consumption, distillation/separation considerations, that can be experience when separating water/solvent/alcohol from one another. Removing water from rich solvent may be performed because the solvent is likely reused for subsequent extractions.

As will be appreciated by those of skill in the art, the solvent drying method, techniques and approaches can be implemented with a solvent mixture, this is to say that the first solvent comprises the solvent mixture as described throughout this document. While a variety of the first and second solvent's properties can be considered when determining which solvent to use as the drying or second solvent, these properties generally mirror those considered with respect to the first and second solvents in a solvent mixture.

Further Discussion of Examples and Individual Solvent's Impact on Solvent Mixture The following discussion is provided to further describe individual solvent characteristics. The individual solvent's properties can be used to tailoring solvent mixture by selecting solvents that exhibit properties that are beneficial for butanol extraction but are not indicated by a liner combination of the first and second solvent's, respective, properties relative to that solvent's mole fraction in the solvent mixture.

Referring now to FIG. 11A, a graphic representation illustrating how an individual solvent can exhibit a beneficial property is discussed. This graphical representation was generated using Aspen modeling software as is described at various locations in this document. In this embodiment, isododecane is added to COFA to improve the solvent mixture's dryness. For example, adding isododecane to COFA even in a small amount can reduce the moisture content of the solvent mixture. Accordingly, adjusting the molar concentration of COFA to isododecane impacts the moisture content of the resultant solvent mixture in a non-linear manner, e.g., synergistically in a favorable way for the extraction to be performed. As is illustrated, the dashed line illustrates how COFA and isododecane are anticipated to behave with respect to moisture content based on a linear combination of the two, while the solid (curved) line indicates how increasing the concentration of isododecane in the solvent mixture impacts moisture content of the solvent mixture, up to a solvent mixture that is one hundred percent (100%) isododecane on a molar basis. As can be seen, increasing the concentration of isododecane up to approximately seventy percent (70%) can improve the dryness of the solvent mixture (COFA and isododecane) over that of COFA alone for use in extracting alcohol from fermentation broth. While isododecane concentrations up to seventy percent (70%) by molar concentration show lower moisture content (non-linear behavior), it is to be appreciated that isododecane can be implemented at lower concentrations.

Referring now to FIGS. 11B and 11C, these figures illustrate Kd in comparison to different molar concentrations to illustrate the impact of two similar solvents (isododecane and isododecanol). The mixtures of example 11B exhibit a butanol affinity that is higher than what would be expected from a linear combination. Solvent mixtures of isododecane and isododecanol in some examples behave less like a linear combination that that of other solvent mixtures. For example, a solvent mixtures of tetrabutylurea with isododecane illustrated in 11 C can behave substantially like a linear combination while, comparatively, isododecane and isododecanol behave in a less or non-ideal manner with respect to Kd.

Referring to FIG. 12, in embodiments, some solvents do not exhibit expected tradeoffs between, for example, Kd and hydrobhobicity. For examples, alkylphenols and alkyl ureas do not follow an expected tradeoff between Kd and log P for butanol extraction. This is to say that these solvents do not exhibit a drop-off in butanol distribution equilibrium partitioning in comparison to that solvent's hydrophobicity as is generally expected for organic solvents. The line (e.g., the curve captioned "general tradeoff"), was graphically determined using standard techniques from data points of solvents that do exhibit this correlation between log P and the various solvent's butanol partition coefficient as can be observed. As also can be seen, thymol, tributylphosphate, and tetrabutylurea exhibit high butanol distribution equilibrium partitioning between the aqueous and solvent phases, while having higher log P than that which is expected. Accordingly, inclusion of one or more of these solvents in a solvent mixture, even at low concentration, can increase the mixture's butanol affinity beyond that indicated by a linear combination of one of these solvents and a co-solvent (second solvent). Similar examples exist for toxicity (biocompatibility) (please see FIG. 12), and so forth.

Referring now to FIG. 13, this figure is an illustration of boiling points in comparison to log P for a variety of solvents. As shown, different solvents exhibit different boiling points/hydrophobicities even though they have the same number of carbons atoms. These differences in log P to boiling point can be used to tailor solvent mixture properties to optimize beneficial properties while minimizing or eliminating unfavorable properties. The differences in boiling points and/or hydrophobicities may be attributable to the solvents' structure, including but not limited to, branched, aromatic, orientation of substituent groups, aliphatic, and so forth. Of note, thymol exhibits a low boiling point and low toxicity as indicated by its boiling point of approximately two-hundred thirty degrees Celsius (230° C.) and its log P of approximately three point three (3.3). In addition, thymol is generally considered environmentally benign and is readily available as it is prevalent in thyme.

Referring now to FIG. 14, this figure is a graphic illustration of different molar concentrations of thymol in respectively corn oil and 1,3,5-triisopropylbenzene. As can be observed, when mixed in a two solvent system with corn oil, the log P of corn oil/thymol decreases from a high log P of approximately eighteen (19) to a log P of approximately six (6) with the addition of approximately one molar percent thymol, indicating a non-linear relationship in a disfavorable manner. Although thymol exhibits high butanol distribution equilibrium partitioning while having a higher log P than that expected for its chemical structure, some experiments indicate a mixture of thymol/corn oil exhibit poor overall properties as the Kd for the thymol/corn oil mixture drops to approximately a log P of four (4). Some potential structural influences include, but are not limited to, differences in chemical structure between corn oil and and thymol (e.g., linear versus aromatic with ortho/para substituents) and the like. Generally, structurally dissimilar solvents are considered to be disadvantaged as they do not follow a like-like heuristic.

In contrast, a solvent mixture of 1,3,5-triisopropylbenzene and thymol although structurally similar (both include aromatics and propyl groups) showed relatively little change in log P when the molar concentration of thymol is increased (up to 10% thymol is illustrated). This is to say that 1,3,5-triisopropylbenzene and thymol behaved in a linear fashion, but in a favorable way. Thus, while exhibiting low log P individually, thymol when combined with triisopropylbenzene does not show marked log P change shown by the corn oil/thymol mixture that does not follow the like-dissolves-like rubric. The behavior of thymol and 1,3,5-triisopropylbenzene may be because both include aromatics and have a propyl group.

Further modifications and alternative embodiments of this disclosure will be apparent to those skilled in the art in view of this description. At times methods are described that can be implemented in conjunction with a computing system configured to perform the method or at least a portion of the method. In situations such as this, a computing system can be a general purpose computer that is programed to perform the method or step. It is to be apparent that the method can be implemented as a set of instructions embodied in computer readable media, e.g., tangible, non-transitory media. Further, computing systems in accordance with the present disclosure can provide output in a variety of ways including displaying information, being configured to control equipment (e.g., fermentation or extraction devices in a particular manner, and so on). It will be recognized, therefore, that the present invention is not limited by these example arrangements and/or hardware in the computing system. Accordingly, this description is to be construed as illustrative only and is for the purpose of teaching those skilled in the art the manner of carrying out the methods, approaches, devices, equipment, systems, and so forth. It is to be understood that the forms of the invention herein shown and described are to be taken as the presently preferred embodiments. Various changes may be made in the shape, size and arrangement of parts. For example, equivalent elements may be substituted for those illustrated and described herein, and certain features of the invention may be utilized independently of the use of other features, all as would be apparent to one skilled in the art after having the benefit of this description.

What is claimed is:

1. A method for recovering butanol from a fermentation medium, the method comprising:
   a) providing a fermentation medium comprising butanol, water, and a recombinant microorganism comprising a butanol biosynthetic pathway, wherein the recombinant microorganism produces butanol;
   b) contacting the fermentation medium with a water immiscible organic extractant composition comprising a dry solvent and a second solvent to form a butanol-containing organic phase and an aqueous phase, wherein the dry solvent is a saturated hydrocarbon that is a branched C7 to C22 alkane or a mixture thereof; and
   c) recovering the butanol from the butanol-containing organic phase.

2. The method of claim 1, wherein the C7 to C22 alkane is a derivative of isobutanol, wherein the derivative of isobutanol is triisobutylene, diisobutylene, tetraisobutylene, isooctane, isohexadecane, or isododecane.

3. The method of claim 2, wherein the derivative of isobutanol is isododecane.

4. The method of claim 1, wherein the contacting of the organic extractant composition with the fermentation media medium occurs in a fermentor.

5. The method of claim 1, further comprising transferring a portion of the fermentation medium from a fermentor to a vessel, wherein the contacting of the organic extractant composition with the fermentation medium occurs in the vessel.

6. The method of claim 1, wherein the second solvent is a C4 to C22 fatty alcohol, a C4 to C28 fatty acid, an ester of a C4 to C28 fatty acid, a C4 to C22 fatty aldehyde, a C7 to C22 ether, a phosphate, an amide, a urea, a phenol, a phosphinate, a carbamate, a phosphoramide, a phosphine oxide, a salicylate, a paraben, or mixtures thereof.

7. The method of claim 6, wherein the second solvent increases a butanol partition coefficient of the organic extractant composition.

8. The method of claim 1, wherein the second solvent is oleyl alcohol, behenyl alcohol, cetyl alcohol, lauryl alcohol, myristyl alcohol, stearyl alcohol, oleaic acid, lauric acid, myristic acid, stearic acid, octanoic acid, decanoic acid, undecanoic acid, methyl myristate, methyl oleate, 1-nonanol, 1-decanol, 2-undecanol, 1-nonanal, undecanol, undecanal, isododecanol, 2,6,8-trimethyl-4-nonanol, lauric aldehyde, 2-methylundecanal, oleamide, linoleamide, palmitamide, steaylamide, 2-ethyl-1-hexanol, 2-hexyl-1-decanol, 2-octyl-1-dodecanol, 3,4,5,6,6-pentamethyl-2-heptanol, or mixtures thereof.

9. The method of claim 8, wherein the second solvent increases a butanol partition coefficient of the organic extractant composition.

10. The method of claim 1, wherein the recovered butanol has an effective titer from about 30 grams per liter to about 80 grams per liter of the fermentation medium.

11. The method of claim 1, wherein the recovered butanol has an effective titer of at least 50 grams per liter of the fermentation medium.

12. The method of claim 1, wherein the butanol is isobutanol.

13. A composition comprising butanol in a water immiscible organic extractant composition, wherein the organic extractant composition comprises a dry solvent and a second solvent, wherein the dry solvent is a saturated hydrocarbon that is a branched C7 to C22 alkane or a mixture thereof.

14. The composition of claim 13, wherein the C7 to C22 alkane is a derivative of isobutanol, wherein the derivative of isobutanol is triisobutylene, diisobutylene, tetraisobutylene, isooctane, isohexadecane, or isododecane.

15. The composition of claim 13, wherein the derivative of isobutanol is isododecane.

16. The composition of claim 13, wherein the second solvent is a C4 to C22 fatty alcohol, a C4 to C28 fatty acid, an ester of a C4 to C28 fatty acid, a C4 to C22 fatty aldehyde, a C7 to C22 ether, a phosphate ester, an amide, a urea, a phenol, a phosphinate, a carbamate, a phosphoramide, a phosphine oxide, a salicylate, a paraben, or mixtures thereof.

17. The composition of claim 13, wherein the second solvent is oleyl alcohol, behenyl alcohol, cetyl alcohol, lauryl alcohol, myristyl alcohol, stearyl alcohol, oleaic acid, lauric acid, myristic acid, stearic acid, octanoic acid, decanoic acid, undecanoic acid, methyl myristate, methyl oleate, 1-nonanol, 1-decanol, 2-undecanol, 1-nonanal, undecanol, undecanal, isododecanol, 2,6,8-trimethyl-4-nonanol, lauric aldehyde, 2-methylundecanal, oleamide, linoleamide, palmitamide, steaylamide, 2-ethyl-1-hexanol, 2-hexyl-1-decanol, 2-octyl-1-dodecanol, 3,4,5,6,6-pentamethyl-2-heptanol, or mixtures thereof.

18. The composition of claim 13, wherein the butanol is isobutanol.

* * * * *